US007071300B2

(12) United States Patent
Deshayes et al.

(10) Patent No.: US 7,071,300 B2
(45) Date of Patent: Jul. 4, 2006

(54) IGF ANTAGONIST PEPTIDES

(75) Inventors: Kurt D. Deshayes, San Francisco, CA (US); Henry B. Lowman, El Granada, CA (US); Michelle L. Schaffer, Cambridge (GB); Sachdev S. Sidhu, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 417 days.

(21) Appl. No.: 10/098,093

(22) Filed: Mar. 13, 2002

(65) Prior Publication Data

US 2003/0092631 A1 May 15, 2003

Related U.S. Application Data

(60) Provisional application No. 60/275,904, filed on Mar. 14, 2001.

(51) Int. Cl.
*A61K 38/30* (2006.01)
*A61K 38/10* (2006.01)
*C07K 11/00* (2006.01)
*C07K 14/65* (2006.01)

(52) U.S. Cl. .......................... 530/326; 530/402; 514/13
(58) Field of Classification Search ................ 530/326, 530/300
See application file for complete search history.

(56) References Cited

U.S. PATENT DOCUMENTS

| 4,988,675 | A | 1/1991 | Froesch et al. |
| 5,077,276 | A | 12/1991 | Ballard et al. |
| 5,164,370 | A | 11/1992 | Ballard et al. |
| 5,342,763 | A | 8/1994 | Swartz |
| 5,470,828 | A | 11/1995 | Ballard et al. |
| 2002/0165155 | A1 | 11/2002 | Schaffer et al. |

FOREIGN PATENT DOCUMENTS

| EP | 0 294 021 | 4/1988 |
| EP | 0 369 943 | 11/1989 |
| EP | 0 375 438 | 12/1989 |
| EP | 742228 | 11/1996 |
| WO | WO 89/09792 | 6/1988 |
| WO | WO 89/08667 | 3/1989 |
| WO | WO 89/09268 | 3/1989 |
| WO | WO 91/03253 | 3/1991 |
| WO | WO 93/23067 | 11/1993 |
| WO | WO 93/23071 | 11/1993 |
| WO | WO 94/04569 | 3/1994 |
| WO | WO 96/33216 | 10/1996 |
| WO | WO 98/45427 | 10/1998 |
| WO | WO 99/38011 | 7/1999 |
| WO | WO 00/23469 | 4/2000 |
| WO | WO 01/25790 | 4/2001 |
| WO | WO 01/72771 | 10/2001 |

OTHER PUBLICATIONS

Vajdos et al., "Crystal Structure of Human Insulin-Like Growth Factor-1: Detergent Binding Inhibits Binding Protein Interactions." *Biochemistry* 40:11022-11029 (2001).
Bach and Rechler., "Insulin-Like Growth Factor Binding Proteins." *Diabetes Reviews*. 3(1):38-61 (1995).
Ballard et al., "Does IGF-I Ever Act Through the Insulin Receptor?" *The Insulin-Like Growth Factors and Their Regulatory Proteins.*, Baxter, eds., Amsterdam: Elsevier pp. 131-138 (1994).
Bar et al., "Tissue Localization of Perfused Endothelial Cell IGF Binding Protein is Markedly Altered by Association with IGF-I." *Endocrinology*, 127(6):3243-3245 (1990).
Baserga., "The Insulin-Like Growth Factor 1 Receptor: A Key to Tumor Growth?" *Cancer Research* 55:249-252 (Jan. 1995).
Baxter., "The Somatomedins: Insulin-Like Growth Factors." *Advances in Clinical Chemistry*. 25:49-115 (1986).
Bayne et al., "Structural Analogs of Human Insulin-Like Growth Factor I with Reduced Affinity for Serum Binding Proteins and the Type 2 Insulin-Like Growth Factor Receptor." *J. Bio. Chem*. 263:6233-6239 (1988).
Bayne et al., "The C Region of Human Insulin-Like Growth Factor (IGF) I is Required for High Affinity Binding to the Type 1 IGF Receptor." *J. Bio. Chem*. 264(19):11004-11008 (1988).
Bayne et al., "The Roles of Tyrosines 24, 31, and 60 in the High Affinity Binding of Insulin-Like Growth Factor-I to the Type I Insulin-Like Growth Factor Receptor." *J. Bio. Chem*. 265(26):15648-15652 (Sep. 15, 1990).
Binoux, M., "Recent Data on Somatomedins (Insulin-Like Growth Factors)." *Annales d'Endocrinologie* (English Abstract Included) 41:157-192 (1980).
Blundell et al., "Insulin-Like Growth Factor: A Model for Tertiary Structure Accounting for Immunoreactivity and Receptor Binding." *Proc. Natl. Acad. Sci. USA* 75(1):180-184 (Jan. 1978).
Blundell et al., "Tertiary Structures, Receptor Binding, and Antigenicity of Insulinlike Growth Factors." *Federation Proc*. 42:2592-2597 (1983).
Buckbinder et al., "Induction of the Growth Inhibitor IGF-Binding Protein 3 by p53." *Nature*. 377:646-649 (Oct. 1995).
Cascieri et al., "Mutants of Human Insulin-Like Growth Factor I with Reduced Affinity for the Type 1 Insulin-Like Growth Factor Receptor." *Biochemistry* 27(9):3229-3233 (May 3, 1988).

(Continued)

Primary Examiner—Christine J. Saoud
(74) *Attorney, Agent, or Firm*—Ginger R. Dreger; Janet E. Hasak; Heller Ehrman LLP

(57) ABSTRACT

Peptides are provided that antagonize the interaction of IGF-1 with its binding proteins, insulin receptor, and IGF receptor. These IGF antagonist peptides are useful in treating disorders involving IGF-1 as a causative agent, such as, for example, various cancers.

3 Claims, 1 Drawing Sheet

OTHER PUBLICATIONS

Figure 1:
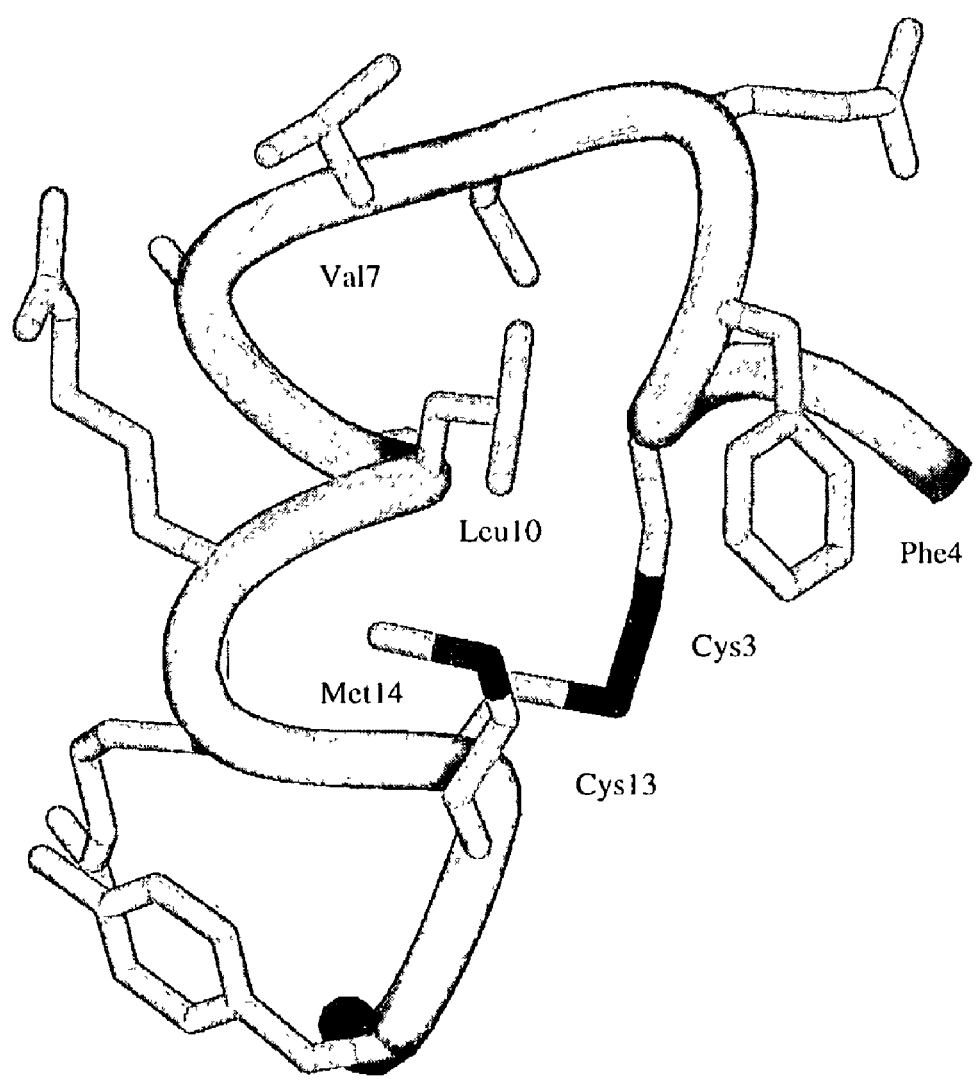

Cascieri et al., "Structural Analogs of Human Insulin-Like Growth Factor (IGF) I with Altered Affinity for Type 2 IGF Receptors." *J. Bio. Chem.* 264:2199-2202 (1989).

Clemmons and Van Wyk., "Somatomedin: Physiological Control and Effects on Cell Proliferation." *Handbook Exp. Pharmacol.* 57:161-208 (1981).

Clemmons et al., "Discrete Alterations of the Insulin-Like Growth Factor I Molecule Which Alter Its Affinity for Insulin-Like Growth Factor-Binding Proteins Result in Changes in Bioactivity." *J. Bio. Chem.* 265(21):12210-12216 (1990).

Clemmons et al., "The Role of Insulin-Like Growth Factor Binding Proteins in Modifying IGF Actions." *Anal. NY Acad. Sci. USA* 692:10-21 (1993).

Cohen and Ellwein., "Cell Proliferation in Carcinogenesis." *Science.* 249:1007-1011 (Aug. 1990).

Cohen and Ellwein., "Genetic Errors, Cell Proliferation, and Carcinogenesis." *Cancer Research.* 51:6493-6505 (Dec. 1991).

Cohen et al., "Biological Effects of Prostate Specific Antigen as an Insulin-Like Growth Factor Binding Protein-3 Protease." *J. Endocrinology.* 142:407-415 (1994).

Cohen et al., "Insulin-Like Growth Factors (IGFs), IGF Receptors, and IGF-Binding Proteins in Primary Cultures of Prostate Epithelial Cells." *J. Clin. Endocrin. & Metab.* 73:401-407 (1991).

Cohen et al., "The IGF Axis in the Prostate." *Horm. & Metab. Res.* 26:81-84 (1994).

Cooke et al., "Solution Structure of Human Insulin-Like Growth Factor 1: A Nuclear Magnetic Resonance and Restrained Molecular Dynamics Study" *Biochemistry* 30:5484-5491 (1991).

Culig et al., "Androgen Receptor Activation in Prostatic Tumor Cell Lines by Insulin-Like Growth Factor-I, Keratinocyte Growth Factor, and Epidermal Growth Factor." *Cancer Research.* 54:5474-5478 (1994).

Cullen et al., "Insulin-Like Growth Factor Receptor Expression and Function in Human Breast Cancer." *Cancer Research.* 50:48-53 (1990).

Daughaday and Rotwein., "Insulin-Like Growth Factors I and II. Peptide, Messenger Ribonucleic Acid and Gene Structures, Serum, and Tissue Concentrations." *Endocrin. Rev.* 10(1):68-91 (1989).

De Wolf et al., "Solution Structure of a Mini IGF-1." *Protein Sci.* 5:2193-2202 (1996).

Dubaquie and Lowman, "Total Alanine-Scanning Mutagenesis of Insulin-Like Growth Factor I (IGF-I) Identifies Differential Binding Epitopes for IGFBP-1 and IGFBP-3" *Biochemistry* 38(20):6386-6396 (1999).

Feyen et al., "Recombinant Human [Cys$^{281}$] Insulin-Like Growth Factor-Binding Protein 2 Inhibits Both Basal and Insulin-Like Growth Factor I-Stimulated Proliferation and Collagen Synthesis in Fetal Rat Calvariae." *J Bio. Chem,* 266:19469-19474 (1991).

Figueroa et al., "Recombinant Insulin-Like Growth Factor Binding Protein-1 Inhibits IGF-I, Serum, and Estrogen-Dependent Growth of MCF-7 Human Breast Cancer Cells." *J. Cell Phys.* 157:229-236 (1993).

Garrett et al., "Crystal Structure of the First Three Domains of the Type-1 Insulin-Like Growth Factor Receptor." *Nature.* 394(6691):395-399 (Jul. 23, 1998).

Hasegawa et al., "The Free Form of Insulin-Like Growth Factor I Increases in Circulation During Normal Human Pregnancy." *J. Clin. Endocrinol. Metabol.* 80:3284-3286 (1995).

Hizuka et al., "Measurement of Free Form of Insulin-Like Growth Factor I in Human Plasma." *Growth Regulation.* 1:51-55 (1991).

Horney et al., "Elevated Glucose Increases Mesangial Cell Sensitivity to Insulin-Like Growth Factor I." *Am. J. Physiol.* 274:F1045-F1053 (1998).

Hsing et al., "Regulation of Apoptosis Induced by Transforming Growth Factor-β1 in Nontumorigenic and Tumorigenic Rat Prostatic Epithelial Cell Lines." *Cancer Research.* 56:5146-5149 (1996).

Humbel., "Insulin-Like Growth Factors I and II." *European Journal of Biochemistry.* 190:445-462 (1990).

Huynh et al., "Estradiol and Antiestrogens Regulate a Growth Inhibitory Insulin-Like Growth Factor Binding Protein 3 Autocrine Loop in Human Breast Cancer Cells." *J. Bio. Chem.* 271(2):1016-1021 (1996).

"Insulin-Like Growth Factors and Cancer." *R & D Systems—Cytokine Bulletin* pp. 1-2 (Fall Issue 2000).

Iwamura et al., "Insulin-Like Growth Factor I: Action and Receptor Characterization in Human Prostate Cancer Cell Lines." *Prostate.* 22:243-252 (1993).

Jones and Clemmons., "Insulin-Like Growth Factors and Their Binding Proteins: Biological Actions." *Endocrine Rev.* 16(1):3-34 (1995).

Juul et al., "Serum Concentrations of Free and Total Insulin-Like Growth Factor-I, IGF Binding Proteins -1 and -3 and IGFBP-3 Protease Activity in Boys with Normal or Precocious Puberty." *Clin. Endocrin.* 44:515-523 (1996).

Juul et al., "Serum Insulin-Like Growth Factor-I in 1030 Healthy Children, Adolescents, and Adults: Relation to Age, Sex, Stage of Puberty, Testicular Size, and Body Mass Index." *J. Clin. Endocrin. & Metab.* 78(8):744-752 (1994).

Juul et al., "Serum Levels of Insulin-Like Growth Factor (IGF)-Binding Protein-3 (IGFBP-3) in Healthy Infants, Children, and Adolescents: The Relation to IGF-I, IGF-II, IGFBP-1, IGFBP-2, Age, Sex, Body Mass Index, and Pubertal Maturation." *J. Clin. Endocrin. & Metab.* 80:2534-2542 (1995).

Khandwala et al., "The Effects of Insulin-Like Growth Factors on Tumorigenesis and Neoplastic Growth." *Endocrine Rev.* 21(3):215-244 (2000).

Laajoki et al., "Solution Structure and Backbone Dynamics of Long-[Arg$^3$] Insulin-Like Growth Factor-I." *J. Bio. Chem.* 275(14):10009-10015 (2000).

Lee et al., "Activation of Estrogen Receptor-Mediated Gene Transcription by IGF-I in Human Breast Cancer Cells." *J. Endocrinol.* 152:39-47 (1997).

LeRoith et al., "Insulin-Like Growth Factors and Cancer." *Annals of Internal Medicine.* 122(1):54-59 (Jan. 1995).

Long et al., "Loss of the Metastatic Phenotype in Murine Carcinoma Cells Expressing an Antisense RNA to the Insulin-Like Growth Factor Receptor." *Cancer Research.* 55:1006-1009 (1995).

Lowman et al., "Molecular Mimics of Insulin-Like Growth Factor 1 (IGF-1) for Inhibiting IGF-1: IGF-Binding Protein Interactions." *Biochemistry* 37(25):8870-8878 (1998).

McGuire et al., "Regulation of Insulin-Like Growth Factor-Binding Protein (IGFBP) Expression by Breast Cancer Cells: Use of IGFBP-1 as an Inhibitor of Insulin-Like Growth Factor Action." *J. Natl. Cancer Institute* 84(17):1336-1341 (1992).

Oh et al., "Antiproliferative Actions of Insulin-Like Growth Factor Binding Protein (IGFBP)-3 in Human Breast Cancer Cells." *Prog. Growth Factor Res.* 6(2-4):503-512 (1995).

Oh et al., "Characterization of the Affinities of Insulin-Like Growth Factor (IGF)-Binding Proteins 1-4 for IGF-I, IGF-II, IGF-I/Insulin Hybrid, and IGF-I Analogs." *Endocrinology.* 132:1337-1344 (1993).

Oh et al., "Insulin-Like Growth Factor (IGF)-Independent Action of IGF-Binding Protein-3 in Hs578T Human Breast Cancer Cells." *J. Bio. Chem.* 268(20):14964-14971 (1993).

Peterkofsky et al., "Elevated Activity of Low Molecular Weight Insulin-Like Growth Factor-Binding Proteins in Sera of Vitamin C-Deficient and Fasted Guinea Pigs" *Endocrinology* 128(4):1769-1779 (1991).

Pietrzkowski et al., "Inhibition of Cellular Proliferation by Peptide Analogues of Insulin-Like Growth Factor 1." *Cancer Research.* 52:6447-6451 (1992).

Pratt and Pollak., "Insulin-Like Growth Factor Binding Protein 3 (IGF-BP3) Inhibits Estrogen-Stimulated Breast Cancer Cell Proliferation." *Biophys. Res. Comm.* 198(1):292-297 (1994).

Quinn et al., "Insulin-Like Growth Factor Expression in Human Cancer Cell Lines." *J. Bio. Chem.* 271(19):11477-11483 (1996).

Rajah et al., "Insulin-Like Growth Factor (IGF)-Binding Protein-3 Induces Apoptosis and Mediates the Effects of Transforming Growth Factor-β1 on Programmed Cell Death through a p53- and IGF-Independent Mechanism." *J. Bio. Chem.* 272(18):12181-12188 (1997).

Rinderknecht and Humbel, "Polypeptides with Nonsuppressible Insulin-Like and Cell-Growth Promoting Activities in Human Serum: Isolation, Chemical Characterization, and Some Biological Properties of Forms I and II." *Proc. Natl. Acad. Sci. USA.* 73(7):2365-2369 (1976).

Rinderknecht and Humbel., "The Amino Acid Sequence of Human Insulin-Like Growth Factor I and Its Structural Homology with Proinsulin." *Journal of Biological Chemistry* 253(8):2769-2776 (1978).

Rohlik et al., "An Antibody to the Receptor for Insulin-Like Growth Factor I Inhibits the Growth of MCF-7 Cells in Tissue Culture." *Biochem. & Biophys. Res. Comm.* 149(1):276-281 (Nov. 1987).

Sato et al., "Three-Dimensional Structure of Human Insulin-Like Growth Factor-I (IGF-I) Determined by $^1$H-NMR and Distance Geometry." *Int. J. Pep. Protein Res.* 41:433-440 (1993).

Smith et al., "Essential Role of Growth Hormone in Ischemia-Induced Retinal Neovascularization." *Science.* 276:1706-1709 (1997).

Steller et al., "Overexpression of the Insulin-Like Growth Factor-1 Receptor and Autocrine Stimulation in Human Cervical Cancer Cells." *Cancer Research.* 56:1761-1765 (1996).

Stracke et al., "The Type I Insulin-Like Growth Factor Receptor is a Motility Receptor in Human Melanoma Cells." *J. Bio. Chem.* 264(36):21544-21549 (Dec. 1989).

Torres et al., "Solution Structure of Human Insulin-Like Growth Factor II: Relationship to Receptor and Binding Protein Interactions." *J. Mol. Bio.* 248(2):385-401 (Apr. 28, 1995).

Trainer et al., "Treatment of Acromegaly with the Growth Hormone-Receptor Antagonist Pegvisomant." *New Engl. J. Med.* 342(16):1171-1177 (Apr. 2000).

Valentinis et al., "The Human Insulin-Like Growth Factor (IGF) Binding Protein-3 Inhibits the Growth of Fibroblasts with a Targeted Disruption of the IGF-I Receptor Gene." *Molecular Endocrinology.* 9:361-367 (1995).

Van Wyk et al., "The Somatomedins: A Family of Insulinlike Hormones Under Growth Hormone Control." *Recent Prog. Horm. Res.* 30:259-318 (1974).

Yee et al., "Insulin-Like Growth Factor Binding Protein 1 Expression Inhibits Insulin-Like Growth Factor I Action in MCF-7 Breast Cancer Cells." *Cell Growth & Diff.* 5:73-77 (1994).

Baxter, Robert C., "The Insulin-Like Factors and Their Binding Proteins", Comp. Biochem. Physiol., vol. 91B, pp. 229-235, 1988.

Baxter, Robert C., et al., "Binding Proteins for Insulin-Like Growth Factors in Adult Rat Serum Comparison with Other Human and Rat Binding Proteins", Biochemical and Biophysical Research Communication, vol. 147, pp. 408-415, 1987.

Binkert, C., et al., Cloning, Sequence Analysis and Expression of a cDNA Encoding a Novel Insulin-Like Growth Factor Binding Protein (IGFBP-2), EMBO J., vol. 8; pp. 2497-2502, 1989.

Brewer, Michael T., et al., "Cloning, Characterization and Expression of a Human Insulin-Like Growth Factor Binding Protein", Biochemical and Biophysical Research Communication, vol. 152, pp. 1289-1297, 1988.

Brinkman, A., et al., "Isolation and Characterization of a cDNA Encoding the Low Molecular Weight Insulin-Like Growth Factor Binding Protein (IBP-1)", The EMBO Journal, vol. 7, pp. 2417-2423, 1988.

Dennis, Mark S., et al., "Peptide Exosite Inhibitors of Factor VIIa as Anticoagulants", Nature, vol. 404, pp. 465-470, 2000.

Grupe, Andrew, et al., Inhibition of Insulin receptor Phosphorylation by PC-1 Is Not Mediated by the Hydrolysis of Adenosine Triphosphate or the Generation of Adenosine J. Biol. Chem., vol. 270, pp. 22085-22088, 1995.

Jin, Lei, et al., "High Resolution Functional Analysis of Antibody-Antigen Interactions", J. Mol. Biol., vol. 226, pp. 851-865, 1992.

Lassalle, Phillppe, et al., "ESM-1 Is a Novel Human Endothelial Cell-Specific Molecule Expressed in Lung and Regulated by Cytokines", J. Biol. Chem., vol. 271, pp. 20458-20464, 1996.

Lee, Yao-Ling, et al., "Insulin-Like Growth Factor (IGF) Binding Protein Complementary Deoxyribonucleic Acid from Human HEP G2 Hepatoma Cells: Predicted Protein Sequence Suggests and IGF Binding Domain Different from Those of the IGF-I and IGF-II Receptors", Mol. Endocrinal., vol. 2, pp. 404-411, 1988.

Leung, David, et al., "Growth Hormone Receptor and Serum Binding Protein: Purification, Cloning and Expression", Nature 330, pp. 537-543, 1987.

Martin, Janet L., et al., "Insulin-like Growth Factor-binding Protein from Human Plasma", J. Biol. Chem., vol. 261, pp. 8754-8760, 1986.

Oh, Youngman, et al., "Synthesis and Characterization of Insulin-like Growth Factor-Binding Protein (IGFBP)-7", J. Biol. Chem., vol. 271, pp. 30322-30325, 1996.

Sidhu, Sachdev S., et al., "Phage Display for Selection of Novel Binding Peptides", Methods in Enzymology, vol. 328, pp. 333-363, 2000.

Swisshelm, Karen, et al., "Enhanced Expression of an Insulin Growth Factor-like Binding Protein (mac25) in Senescent Human Mammary Epitherlial Cells and Induced Expression with Retinoic Acid", Proc. Nat. Sci. USA, vol. 92, pp. 4472-4476, 1995.

Wood, William I., et al., "Cloning and Expression of the Growth Hormone-Dependent Insulin-Like Growth Factor-Binding Protein", Molecular Endocrinology, vol. 2, pp. 1176-1185, 1988.

Yamauchi, Teruaki, et al., "Purification and Molecular Cloning of Prostacyclin-Stimulating Factor from Serum-free Conditioned Medium of Human Diploid Fibroblast Cells", Pro Biochemical Journal, vol. 303, pp. 591-598, 1994.

SEQUENCE LISTING

<160> NUMBER OF SEQ ID NOS: 122

<210> SEQ ID NO 1
<211> LENGTH: 15
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 1-2, 4-5, 8, 11, 12, 15
<223> OTHER INFORMATION: Unknown amino acid

<400> SEQUENCE: 1

Xaa Xaa Cys Xaa Xaa Ser Val Xaa Ala Leu Xaa Xaa Cys Met Xaa
 1               5                  10                  15

<210> SEQ ID NO 2
<211> LENGTH: 16
<212> TYPE: PRT
<213> ORGANISM: Artificial sequence
<220> FEATURE:
<223> OTHER INFORMATION: Sequence is synthesized

<400> SEQUENCE: 2

Arg Asn Cys Phe Glu Ser Val Ala Ala Leu Arg Arg Cys Met Tyr
 1               5                  10                  15

Gly

<210> SEQ ID NO 3
<211> LENGTH: 16
<212> TYPE: PRT
<213> ORGANISM: Artificial sequence
<220> FEATURE:
<223> OTHER INFORMATION: Sequence is synthesized

<400> SEQUENCE: 3

Met Asp Cys Leu Ala Ser Val Glu Ala Leu Lys Trp Cys Met Tyr
 1               5                  10                  15

Gly

<210> SEQ ID NO 4
<211> LENGTH: 16

<212> TYPE: PRT
<213> ORGANISM: Artificial sequence
<220> FEATURE:
<223> OTHER INFORMATION: Sequence is synthesized

<400> SEQUENCE: 4

Phe Glu Cys Leu Thr Ser Val Glu Ala Leu Arg Gly Cys Met Tyr
1               5                   10                  15

Gly

<210> SEQ ID NO 5
<211> LENGTH: 15
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 1,2, 4,5, 7, 8, 10-11, 15
<223> OTHER INFORMATION: Unknown amino acid

<400> SEQUENCE: 5

Xaa Xaa Cys Xaa Xaa Asp Xaa Xaa Gly Xaa Xaa Tyr Cys Trp Xaa
1               5                   10                  15

<210> SEQ ID NO 6
<211> LENGTH: 16
<212> TYPE: PRT
<213> ORGANISM: Artificial sequence
<220> FEATURE:
<223> OTHER INFORMATION: Sequence is synthesized

<400> SEQUENCE: 6

Leu Gly Cys Ala Ser Asp Leu Ala Gly Phe Trp Tyr Cys Trp Ala
1               5                   10                  15

Gly

<210> SEQ ID NO 7
<211> LENGTH: 16
<212> TYPE: PRT
<213> ORGANISM: Artificial sequence
<220> FEATURE:
<223> OTHER INFORMATION: Sequence is synthesized

<400> SEQUENCE: 7

Trp Arg Cys Val Asp Asp Leu Gly Gly Phe Gln Tyr Cys Trp Ala
1               5                   10                  15

Gly

<210> SEQ ID NO 8
<211> LENGTH: 23
<212> TYPE: PRT
<213> ORGANISM: Escherichia coli

<400> SEQUENCE: 8

Met Lys Lys Asn Ile Ala Phe Leu Leu Ala Ser Met Phe Val Phe
1               5                   10                  15

Ser Ile Ala Thr Asn Ala Tyr Ala
                20

<210> SEQ ID NO 9
<211> LENGTH: 7
<212> TYPE: PRT
<213> ORGANISM: Artificial sequence
<220> FEATURE:
<223> OTHER INFORMATION: Sequence is synthesized

```
<400> SEQUENCE: 9

Gly Gly Gly Ser Gly Gly Gly
 1               5

<210> SEQ ID NO 10
<211> LENGTH: 50
<212> TYPE: PRT
<213> ORGANISM: Unknown
<220> FEATURE:
<223> OTHER INFORMATION: Phage protein

<400> SEQUENCE: 10

Ala Glu Gly Asp Asp Pro Ala Lys Ala Ala Phe Asn Ser Leu Gln
 1               5                  10                  15

Ala Ser Ala Thr Glu Tyr Ile Gly Tyr Ala Trp Ala Met Val Val
                20                  25                  30

Val Ile Val Gly Ala Thr Ile Gly Ile Lys Leu Phe Lys Lys Phe
                35                  40                  45

Thr Ser Lys Ala Ser
                50

<210> SEQ ID NO 11
<211> LENGTH: 8
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 1-8
<223> OTHER INFORMATION: Unknown amino acid

<400> SEQUENCE: 11

Xaa Xaa Xaa Xaa Xaa Xaa Xaa Xaa
 1               5

<210> SEQ ID NO 12
<211> LENGTH: 20
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 1-20
<223> OTHER INFORMATION: Unknown amino acid

<400> SEQUENCE: 12

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa
                20

<210> SEQ ID NO 13
<211> LENGTH: 27
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 2-7, 9-14, 17-19, 21-26
<223> OTHER INFORMATION: Unknown amino acid

<400> SEQUENCE: 13

Cys Xaa Xaa Xaa Xaa Xaa Xaa Cys Xaa Xaa Xaa Xaa Xaa Xaa Cys
 1               5                  10                  15
```

```
Cys Xaa Xaa Xaa Cys Xaa Xaa Xaa Xaa Xaa Cys
            20                  25
```

<210> SEQ ID NO 14
<211> LENGTH: 13
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 3-5, 7-12
<223> OTHER INFORMATION: Unknown amino acid

<400> SEQUENCE: 14

```
Cys Cys Xaa Xaa Xaa Cys Xaa Xaa Xaa Xaa Xaa Xaa Cys
 1               5                  10
```

<210> SEQ ID NO 15
<211> LENGTH: 19
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 3-7, 9-12, 14-17
<223> OTHER INFORMATION: Unknown amino acid

<400> SEQUENCE: 15

```
Cys Cys Xaa Xaa Xaa Xaa Xaa Cys Xaa Xaa Xaa Xaa Cys Xaa Xaa
 1               5                  10                  15

Xaa Xaa Cys Cys
```

<210> SEQ ID NO 16
<211> LENGTH: 21
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 2, 4-10, 12-14, 16-21
<223> OTHER INFORMATION: Unknown amino acid

<400> SEQUENCE: 16

```
Cys Xaa Cys Xaa Xaa Xaa Xaa Xaa Xaa Xaa Cys Xaa Xaa Xaa Cys
 1               5                  10                  15

Xaa Xaa Xaa Xaa Xaa Xaa
            20
```

<210> SEQ ID NO 17
<211> LENGTH: 18
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 1-4, 6, 7, 10-13, 15-18
<223> OTHER INFORMATION: Unknown amino acid

<400> SEQUENCE: 17

```
Xaa Xaa Xaa Xaa Cys Xaa Xaa Gly Pro Xaa Xaa Xaa Xaa Cys Xaa
 1               5                  10                  15

Xaa Xaa Xaa
```

<210> SEQ ID NO 18
<211> LENGTH: 10
<212> TYPE: PRT
<213> ORGANISM: Artificial sequence -continued

```
<220> FEATURE:
<223> OTHER INFORMATION: Sequence is synthesized
<221> NAME/KEY: Xaa
<222> LOCATION: 2-3, 6-9
<223> OTHER INFORMATION: Unknown amino acid

<400> SEQUENCE: 18

Cys Xaa Xaa Gly Pro Xaa Xaa Xaa Xaa Cys
 1               5                  10

<210> SEQ ID NO 19
<211> LENGTH: 20
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 1-7, 9-12, 14-20
<223> OTHER INFORMATION: Unknown amino acid

<400> SEQUENCE: 19

Xaa Xaa Xaa Xaa Xaa Xaa Xaa Cys Xaa Xaa Xaa Xaa Cys Xaa Xaa
 1               5                  10                  15

Xaa Xaa Xaa Xaa Xaa
            20

<210> SEQ ID NO 20
<211> LENGTH: 20
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 1-7, 9-13, 15-20
<223> OTHER INFORMATION: Unknown amino acid

<400> SEQUENCE: 20

Xaa Xaa Xaa Xaa Xaa Xaa Xaa Cys Xaa Xaa Xaa Xaa Xaa Cys Xaa
 1               5                  10                  15

Xaa Xaa Xaa Xaa Xaa
            20

<210> SEQ ID NO 21
<211> LENGTH: 20
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 1-6, 8-13, 15-20
<223> OTHER INFORMATION: Unknown amino acid

<400> SEQUENCE: 21

Xaa Xaa Xaa Xaa Xaa Xaa Cys Xaa Xaa Xaa Xaa Xaa Xaa Cys Xaa
 1               5                  10                  15

Xaa Xaa Xaa Xaa Xaa
            20

<210> SEQ ID NO 22
<211> LENGTH: 20
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 1-6, 8-14, 16-20
<223> OTHER INFORMATION: Unknown amino acid
```

-continued

```
<400> SEQUENCE: 22

Xaa Xaa Xaa Xaa Xaa Xaa Cys Xaa Xaa Xaa Xaa Xaa Xaa Xaa Cys
 1               5                   10                  15

Xaa Xaa Xaa Xaa Xaa
            20

<210> SEQ ID NO 23
<211> LENGTH: 20
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 1-5, 7-14, 16-20
<223> OTHER INFORMATION: Unknown amino acid

<400> SEQUENCE: 23

Xaa Xaa Xaa Xaa Xaa Cys Xaa Xaa Xaa Xaa Xaa Xaa Xaa Xaa Cys
 1               5                   10                  15

Xaa Xaa Xaa Xaa Xaa
            20

<210> SEQ ID NO 24
<211> LENGTH: 20
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 1-5, 7-15, 17-20
<223> OTHER INFORMATION: Unknown amino acid

<400> SEQUENCE: 24

Xaa Xaa Xaa Xaa Xaa Cys Xaa Xaa Xaa Xaa Xaa Xaa Xaa Xaa Xaa
 1               5                   10                  15

Cys Xaa Xaa Xaa Xaa
            20

<210> SEQ ID NO 25
<211> LENGTH: 20
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 1-4, 6-15, 17-20
<223> OTHER INFORMATION: Unknown amino acid

<400> SEQUENCE: 25

Xaa Xaa Xaa Xaa Cys Xaa Xaa Xaa Xaa Xaa Xaa Xaa Xaa Xaa Xaa
 1               5                   10                  15

Cys Xaa Xaa Xaa Xaa
            20

<210> SEQ ID NO 26
<211> LENGTH: 10
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 1-2, 4-7, 9-10
<223> OTHER INFORMATION: Unknown amino acid

<400> SEQUENCE: 26

Xaa Xaa Cys Xaa Xaa Xaa Xaa Cys Xaa Xaa
```

<210> SEQ ID NO 27
<211> LENGTH: 11
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 1-2, 4-8, 10-11
<223> OTHER INFORMATION: Unknown amino acid

<400> SEQUENCE: 27

Xaa Xaa Cys Xaa Xaa Xaa Xaa Xaa Cys Xaa Xaa
 1               5                  10

<210> SEQ ID NO 28
<211> LENGTH: 12
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 1-2, 4-9, 11-12
<223> OTHER INFORMATION: Unknown amino acid

<400> SEQUENCE: 28

Xaa Xaa Cys Xaa Xaa Xaa Xaa Xaa Xaa Cys Xaa Xaa
 1               5                  10

<210> SEQ ID NO 29
<211> LENGTH: 13
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 1-2, 4-10, 12-13
<223> OTHER INFORMATION: Unknown amino acid

<400> SEQUENCE: 29

Xaa Xaa Cys Xaa Xaa Xaa Xaa Xaa Xaa Xaa Cys Xaa Xaa
 1               5                  10

<210> SEQ ID NO 30
<211> LENGTH: 14
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 1-2, 4-11, 13-14
<223> OTHER INFORMATION: Unknown amino acid

<400> SEQUENCE: 30

Xaa Xaa Cys Xaa Xaa Xaa Xaa Xaa Xaa Xaa Xaa Cys Xaa Xaa
 1               5                  10

<210> SEQ ID NO 31
<211> LENGTH: 15
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 1-2, 4-12, 14-15
<223> OTHER INFORMATION: Unknown amino acid

<400> SEQUENCE: 31

```
Xaa Xaa Cys Xaa Xaa Xaa Xaa Xaa Xaa Xaa Xaa Cys Xaa Xaa
 1               5                   10                  15
```

<210> SEQ ID NO 32
<211> LENGTH: 16
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 1-2, 4-13, 15-16
<223> OTHER INFORMATION: Unknown amino acid

<400> SEQUENCE: 32

```
Xaa Xaa Cys Xaa Xaa Xaa Xaa Xaa Xaa Xaa Xaa Xaa Cys Xaa
 1               5                   10                  15

Xaa
```

<210> SEQ ID NO 33
<211> LENGTH: 20
<212> TYPE: PRT
<213> ORGANISM: Artificial sequence
<220> FEATURE:
<223> OTHER INFORMATION: Sequence is synthesized

<400> SEQUENCE: 33

```
Ala Ser Gln Thr Pro Trp Pro Tyr Ser Ile Leu Phe Gly Glu Trp
 1               5                   10                  15

Trp Asn Ala Gly Phe
                 20
```

<210> SEQ ID NO 34
<211> LENGTH: 20
<212> TYPE: PRT
<213> ORGANISM: Artificial sequence
<220> FEATURE:
<223> OTHER INFORMATION: Sequence is synthesized

<400> SEQUENCE: 34

```
Glu Ala Gly Ala Glu Ser Arg Gly Trp Leu Gln Ala Arg Cys Gly
 1               5                   10                  15

Glu Leu Leu Gly Val
                 20
```

<210> SEQ ID NO 35
<211> LENGTH: 20
<212> TYPE: PRT
<213> ORGANISM: Artificial sequence
<220> FEATURE:
<223> OTHER INFORMATION: Sequence is synthesized

<400> SEQUENCE: 35

```
His Trp Asp Trp Thr Gly Gly Tyr Trp Trp Ile Gly Arg Glu Pro
 1               5                   10                  15

Trp Lys Glu Ala Ala
                 20
```

<210> SEQ ID NO 36
<211> LENGTH: 20
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 6
<223> OTHER INFORMATION: Unknown amino acid -continued

```
<400> SEQUENCE: 36

Arg Leu Asn Ala Glu Xaa Leu Arg Met Gly Trp Gly Tyr Met Val
 1               5                  10                  15

Trp His Trp Leu Ser
            20

<210> SEQ ID NO 37
<211> LENGTH: 20
<212> TYPE: PRT
<213> ORGANISM: Artificial sequence
<220> FEATURE:
<223> OTHER INFORMATION: Sequence is synthesized

<400> SEQUENCE: 37

Gly Ala Gln Ala Trp Leu Cys Glu Gln Arg Glu Glu Trp Cys Gly
 1               5                  10                  15

Gln Met Leu Gly Thr
            20

<210> SEQ ID NO 38
<211> LENGTH: 20
<212> TYPE: PRT
<213> ORGANISM: Artificial sequence
<220> FEATURE:
<223> OTHER INFORMATION: Sequence is synthesized

<400> SEQUENCE: 38

Tyr Asp Trp Val Glu Ala Cys Gln Lys Trp Pro Val Leu Cys Met
 1               5                  10                  15

Asp Ser Thr Met Tyr
            20

<210> SEQ ID NO 39
<211> LENGTH: 20
<212> TYPE: PRT
<213> ORGANISM: Artificial sequence
<220> FEATURE:
<223> OTHER INFORMATION: Sequence is synthesized

<400> SEQUENCE: 39

Gly Ile Arg Glu Glu Leu Cys Asp Lys Gly Leu His Lys Met Cys
 1               5                  10                  15

Phe Arg Glu Val Arg
            20

<210> SEQ ID NO 40
<211> LENGTH: 21
<212> TYPE: PRT
<213> ORGANISM: Artificial sequence
<220> FEATURE:
<223> OTHER INFORMATION: Sequence is synthesized

<400> SEQUENCE: 40

Cys Glu Cys Gly Lys Val Ser Ser Arg Gly Cys Glu Lys Leu Cys
 1               5                  10                  15

Trp Leu Val Ser Tyr Met
            20

<210> SEQ ID NO 41
<211> LENGTH: 18
<212> TYPE: PRT
<213> ORGANISM: Artificial sequence
<220> FEATURE:
```

-continued

<223> OTHER INFORMATION: Sequence is synthesized

<400> SEQUENCE: 41

Asp Ala Met Asp Cys Val Val Gly Pro Glu Trp Arg Lys Cys Phe
1               5                   10                  15
Leu Glu Gly

<210> SEQ ID NO 42
<211> LENGTH: 20
<212> TYPE: PRT
<213> ORGANISM: Artificial sequence
<220> FEATURE:
<223> OTHER INFORMATION: Sequence is synthesized

<400> SEQUENCE: 42

Ser Gly Thr Ala Cys Arg Trp Gly Pro Ser Trp Leu Leu Cys Ser
1               5                   10                  15
Leu Ala Gly Ser Pro
                20

<210> SEQ ID NO 43
<211> LENGTH: 20
<212> TYPE: PRT
<213> ORGANISM: Artificial sequence
<220> FEATURE:
<223> OTHER INFORMATION: Sequence is synthesized

<400> SEQUENCE: 43

Gly Glu Gly Pro Glu Cys Asp Leu Arg Gln Trp Gly Asn Leu Cys
1               5                   10                  15
Gly His Trp Glu Thr
                20

<210> SEQ ID NO 44
<211> LENGTH: 20
<212> TYPE: PRT
<213> ORGANISM: Artificial sequence
<220> FEATURE:
<223> OTHER INFORMATION: Sequence is synthesized

<400> SEQUENCE: 44

Leu Ser Ser Glu Glu Cys Trp Glu Ala Leu Lys Trp Gln Gly Cys
1               5                   10                  15
Leu Met Ser Glu Arg
                20

<210> SEQ ID NO 45
<211> LENGTH: 14
<212> TYPE: PRT
<213> ORGANISM: Artificial sequence
<220> FEATURE:
<223> OTHER INFORMATION: Sequence is synthesized

<400> SEQUENCE: 45

Ser Phe Cys Glu Phe Asn Asp Trp Trp Pro Thr Cys Leu Val
1               5                   10

<210> SEQ ID NO 46
<211> LENGTH: 20
<212> TYPE: PRT
<213> ORGANISM: Artificial sequence
<220> FEATURE:
<223> OTHER INFORMATION: Sequence is synthesized

<400> SEQUENCE: 46

-continued

```
Gly Val Glu Thr Cys Tyr Ser Asp Ala Met Asn Thr Gln Tyr Cys
 1               5                  10                  15
Trp Thr Thr Glu Leu
                20

<210> SEQ ID NO 47
<211> LENGTH: 20
<212> TYPE: PRT
<213> ORGANISM: Artificial sequence
<220> FEATURE:
<223> OTHER INFORMATION: Sequence is synthesized

<400> SEQUENCE: 47

Glu Val Ala Arg Cys Val Val Asp Ala Gly Gly Thr Trp Tyr Cys
 1               5                  10                  15
Trp Ala Glu Met Ala
                20

<210> SEQ ID NO 48
<211> LENGTH: 20
<212> TYPE: PRT
<213> ORGANISM: Artificial sequence
<220> FEATURE:
<223> OTHER INFORMATION: Sequence is synthesized

<400> SEQUENCE: 48

Gly Glu Ser Thr Cys Val Thr Asp Leu Glu Arg Val Glu Tyr Cys
 1               5                  10                  15
Trp Asp Glu Lys Ser
                20

<210> SEQ ID NO 49
<211> LENGTH: 20
<212> TYPE: PRT
<213> ORGANISM: Artificial sequence
<220> FEATURE:
<223> OTHER INFORMATION: Sequence is synthesized

<400> SEQUENCE: 49

His Pro Asp Lys Cys Phe Ala Asp Val Arg Ala Leu Gln Glu Cys
 1               5                  10                  15
Met Glu Ser Val Arg
                20

<210> SEQ ID NO 50
<211> LENGTH: 20
<212> TYPE: PRT
<213> ORGANISM: Artificial sequence
<220> FEATURE:
<223> OTHER INFORMATION: Sequence is synthesized

<400> SEQUENCE: 50

Arg Glu Val Lys Cys Met Lys Asp Leu Ser Gly His Glu Tyr Cys
 1               5                  10                  15
Trp Ala Glu Pro Arg
                20

<210> SEQ ID NO 51
<211> LENGTH: 20
<212> TYPE: PRT
<213> ORGANISM: Artificial sequence
<220> FEATURE:
<223> OTHER INFORMATION: Sequence is synthesized
```

```
<400> SEQUENCE: 51

Ser Thr Tyr Ser Cys Ile Arg Asp Met Gly Trp Ala Val Tyr Cys
 1               5                  10                  15

Trp Glu Thr Thr Leu
            20

<210> SEQ ID NO 52
<211> LENGTH: 20
<212> TYPE: PRT
<213> ORGANISM: Artificial sequence
<220> FEATURE:
<223> OTHER INFORMATION: Sequence is synthesized

<400> SEQUENCE: 52

Val Glu Glu Lys Cys Tyr Glu Ser Ile Thr Ala Leu Arg His Cys
 1               5                  10                  15

Met Gln Ala Met Gln
            20

<210> SEQ ID NO 53
<211> LENGTH: 20
<212> TYPE: PRT
<213> ORGANISM: Artificial sequence
<220> FEATURE:
<223> OTHER INFORMATION: Sequence is synthesized

<400> SEQUENCE: 53

Val Glu Ser Glu Cys Leu Leu Ser Leu Pro Asn Leu Arg Arg Cys
 1               5                  10                  15

Met Met Asp Arg Leu
            20

<210> SEQ ID NO 54
<211> LENGTH: 20
<212> TYPE: PRT
<213> ORGANISM: Artificial sequence
<220> FEATURE:
<223> OTHER INFORMATION: Sequence is synthesized

<400> SEQUENCE: 54

Val Lys Asp Glu Cys Leu Met Ser Val Glu Ala Leu Lys Asn Cys
 1               5                  10                  15

Met Gly Leu Val Ser
            20

<210> SEQ ID NO 55
<211> LENGTH: 20
<212> TYPE: PRT
<213> ORGANISM: Artificial sequence
<220> FEATURE:
<223> OTHER INFORMATION: Sequence is synthesized

<400> SEQUENCE: 55

Val Met Asp Gln Cys Phe Glu Ser Tyr Ala Glu Met Arg Lys Cys
 1               5                  10                  15

Met Leu Asp Gly Ser
            20

<210> SEQ ID NO 56
<211> LENGTH: 15
<212> TYPE: PRT
<213> ORGANISM: Artificial sequence
<220> FEATURE:
<223> OTHER INFORMATION: Sequence is synthesized
```

<400> SEQUENCE: 56

Ile Asp Cys Leu Asp Ser Val Glu Ala Leu Lys Gln Cys Met Tyr
 1               5                  10                  15

<210> SEQ ID NO 57
<211> LENGTH: 15
<212> TYPE: PRT
<213> ORGANISM: Artificial sequence
<220> FEATURE:
<223> OTHER INFORMATION: Sequence is synthesized

<400> SEQUENCE: 57

Ile Glu Cys Trp Gln Asp Leu Gln Gly Thr Arg Leu Cys Trp Glu
 1               5                  10                  15

<210> SEQ ID NO 58
<211> LENGTH: 20
<212> TYPE: PRT
<213> ORGANISM: Artificial sequence
<220> FEATURE:
<223> OTHER INFORMATION: Sequence is synthesized

<400> SEQUENCE: 58

Gly Ala Ser Thr Thr Cys Leu Glu Lys Tyr Arg Glu Arg Gln Trp
 1               5                  10                  15

Cys Lys Glu Leu Thr
                 20

<210> SEQ ID NO 59
<211> LENGTH: 20
<212> TYPE: PRT
<213> ORGANISM: Artificial sequence
<220> FEATURE:
<223> OTHER INFORMATION: Sequence is synthesized

<400> SEQUENCE: 59

Gly Glu Ala Ala Glu Cys Ala Tyr Asp Ser Leu Gly Met Ala Tyr
 1               5                  10                  15

Cys Tyr Ala Lys Glu
                 20

<210> SEQ ID NO 60
<211> LENGTH: 20
<212> TYPE: PRT
<213> ORGANISM: Artificial sequence
<220> FEATURE:
<223> OTHER INFORMATION: Sequence is synthesized

<400> SEQUENCE: 60

Gln Ile Pro Ala Gly Cys Tyr Glu Ser Val Gln Ser Leu Leu Glu
 1               5                  10                  15

Cys Val Gln Ser Ala
                 20

<210> SEQ ID NO 61
<211> LENGTH: 20
<212> TYPE: PRT
<213> ORGANISM: Artificial sequence
<220> FEATURE:
<223> OTHER INFORMATION: Sequence is synthesized

<400> SEQUENCE: 61

Thr Ala Gly Ile Glu Cys Ala Tyr Asp Lys His Leu Asp Gln Tyr
 1               5                  10                  15

Cys Trp Trp Lys Glu
            20

<210> SEQ ID NO 62
<211> LENGTH: 15
<212> TYPE: PRT
<213> ORGANISM: Artificial sequence
<220> FEATURE:
<223> OTHER INFORMATION: Sequence is synthesized

<400> SEQUENCE: 62

Arg Asn Cys Phe Glu Ser Val Ala Ala Leu Arg Arg Cys Met Tyr
 1               5                  10                  15

<210> SEQ ID NO 63
<211> LENGTH: 15
<212> TYPE: PRT
<213> ORGANISM: Artificial sequence
<220> FEATURE:
<223> OTHER INFORMATION: Sequence is synthesized

<400> SEQUENCE: 63

Phe Gly Cys Tyr Glu Ser Val Ala Ala Leu Arg Thr Cys Met Tyr
 1               5                  10                  15

<210> SEQ ID NO 64
<211> LENGTH: 15
<212> TYPE: PRT
<213> ORGANISM: Artificial sequence
<220> FEATURE:
<223> OTHER INFORMATION: Sequence is synthesized

<400> SEQUENCE: 64

Tyr His Cys Phe Glu Ser Val Asp Ala Leu Arg Arg Cys Met Lys
 1               5                  10                  15

<210> SEQ ID NO 65
<211> LENGTH: 15
<212> TYPE: PRT
<213> ORGANISM: Artificial sequence
<220> FEATURE:
<223> OTHER INFORMATION: Sequence is synthesized

<400> SEQUENCE: 65

Leu Glu Cys Phe Lys Ser Val Glu Ala Leu Lys Thr Cys Met Ala
 1               5                  10                  15

<210> SEQ ID NO 66
<211> LENGTH: 15
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 12
<223> OTHER INFORMATION: Unknown amino acid

<400> SEQUENCE: 66

Arg Asp Cys Phe Asp Ser Val Glu Ala Leu Arg Xaa Cys Met Tyr
 1               5                  10                  15

<210> SEQ ID NO 67
<211> LENGTH: 15
<212> TYPE: PRT
<213> ORGANISM: Artificial sequence
<220> FEATURE:
<223> OTHER INFORMATION: Sequence is synthesized

<400> SEQUENCE: 67

Leu Asp Cys Phe Thr Ser Val Glu Ala Leu Arg Trp Cys Met Arg
1               5                   10                  15

<210> SEQ ID NO 68
<211> LENGTH: 15
<212> TYPE: PRT
<213> ORGANISM: Artificial sequence
<220> FEATURE:
<223> OTHER INFORMATION: Sequence is synthesized

<400> SEQUENCE: 68

Ala Glu Cys Phe Gly Ser Val Glu Ala Leu Lys Gly Cys Met His
1               5                   10                  15

<210> SEQ ID NO 69
<211> LENGTH: 15
<212> TYPE: PRT
<213> ORGANISM: Artificial sequence
<220> FEATURE:
<223> OTHER INFORMATION: Sequence is synthesized

<400> SEQUENCE: 69

Arg Asp Cys Phe Val Ser Val Glu Ala Leu Arg His Cys Met Tyr
1               5                   10                  15

<210> SEQ ID NO 70
<211> LENGTH: 15
<212> TYPE: PRT
<213> ORGANISM: Artificial sequence
<220> FEATURE:
<223> OTHER INFORMATION: Sequence is synthesized

<400> SEQUENCE: 70

His Asp Cys Phe Ala Ser Val Glu Ala Leu Arg Arg Cys Met Tyr
1               5                   10                  15

<210> SEQ ID NO 71
<211> LENGTH: 15
<212> TYPE: PRT
<213> ORGANISM: Artificial sequence
<220> FEATURE:
<223> OTHER INFORMATION: Sequence is synthesized

<400> SEQUENCE: 71

Ser Asp Cys Phe Gly Ser Val Glu Ala Leu Lys Met Cys Met Tyr
1               5                   10                  15

<210> SEQ ID NO 72
<211> LENGTH: 15
<212> TYPE: PRT
<213> ORGANISM: Artificial sequence
<220> FEATURE:
<223> OTHER INFORMATION: Sequence is synthesized

<400> SEQUENCE: 72

Ser Asp Cys Phe Glu Ser Val Glu Ala Leu Arg Ala Cys Met Tyr
1               5                   10                  15

<210> SEQ ID NO 73
<211> LENGTH: 15
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 15
<223> OTHER INFORMATION: Unknown amino acid

<400> SEQUENCE: 73

Met Glu Cys His Gly Ser Val Glu Ala Leu Lys Ile Cys Met Xaa
1               5                   10                  15

<210> SEQ ID NO 74
<211> LENGTH: 15
<212> TYPE: PRT
<213> ORGANISM: Artificial sequence
<220> FEATURE:
<223> OTHER INFORMATION: Sequence is synthesized

<400> SEQUENCE: 74

Asp Glu Cys Leu Thr Ser Val Glu Ala Leu Arg Tyr Cys Met Ala
1               5                   10                  15

<210> SEQ ID NO 75
<211> LENGTH: 15
<212> TYPE: PRT
<213> ORGANISM: Artificial sequence
<220> FEATURE:
<223> OTHER INFORMATION: Sequence is synthesized

<400> SEQUENCE: 75

Gly Asp Cys Leu Gly Ser Val Glu Ala Leu Lys Met Cys Met Asp
1               5                   10                  15

<210> SEQ ID NO 76
<211> LENGTH: 15
<212> TYPE: PRT
<213> ORGANISM: Artificial sequence
<220> FEATURE:
<223> OTHER INFORMATION: Sequence is synthesized

<400> SEQUENCE: 76

Asn Asp Cys Leu Asp Ser Val Glu Ala Leu Arg Phe Cys Met Ser
1               5                   10                  15

<210> SEQ ID NO 77
<211> LENGTH: 15
<212> TYPE: PRT
<213> ORGANISM: Artificial sequence
<220> FEATURE:
<223> OTHER INFORMATION: Sequence is synthesized

<400> SEQUENCE: 77

Ala Asp Cys Leu Asp Ser Val Glu Ala Leu Arg Arg Cys Met Arg
1               5                   10                  15

<210> SEQ ID NO 78
<211> LENGTH: 15
<212> TYPE: PRT
<213> ORGANISM: Artificial sequence
<220> FEATURE:
<223> OTHER INFORMATION: Sequence is synthesized

<400> SEQUENCE: 78

Phe Glu Cys Leu Thr Ser Val Glu Ala Leu Arg Gly Cys Met Tyr
1               5                   10                  15

<210> SEQ ID NO 79
<211> LENGTH: 15
<212> TYPE: PRT
<213> ORGANISM: Artificial sequence
<220> FEATURE:

<223> OTHER INFORMATION: Sequence is synthesized

<400> SEQUENCE: 79

Arg Asp Cys Leu Ala Ser Val Glu Ala Leu Arg Ser Cys Met Tyr
 1               5                  10                  15

<210> SEQ ID NO 80
<211> LENGTH: 15
<212> TYPE: PRT
<213> ORGANISM: Artificial sequence
<220> FEATURE:
<223> OTHER INFORMATION: Sequence is synthesized

<400> SEQUENCE: 80

Met Asp Cys Leu Ala Ser Val Glu Ala Leu Lys Trp Cys Met Tyr
 1               5                  10                  15

<210> SEQ ID NO 81
<211> LENGTH: 15
<212> TYPE: PRT
<213> ORGANISM: Artificial sequence
<220> FEATURE:
<223> OTHER INFORMATION: Sequence is synthesized

<400> SEQUENCE: 81

Leu Glu Cys Tyr Thr Ser Val Glu Ala Leu Lys Trp Cys Met Arg
 1               5                  10                  15

<210> SEQ ID NO 82
<211> LENGTH: 15
<212> TYPE: PRT
<213> ORGANISM: Artificial sequence
<220> FEATURE:
<223> OTHER INFORMATION: Sequence is synthesized

<400> SEQUENCE: 82

Met Asp Cys Tyr Ser Ser Val Glu Ala Leu Arg Tyr Cys Met Arg
 1               5                  10                  15

<210> SEQ ID NO 83
<211> LENGTH: 15
<212> TYPE: PRT
<213> ORGANISM: Artificial sequence
<220> FEATURE:
<223> OTHER INFORMATION: Sequence is synthesized

<400> SEQUENCE: 83

Leu Thr Cys Leu Asp Ser Val Gly Ala Leu Arg Arg Cys Met Arg
 1               5                  10                  15

<210> SEQ ID NO 84
<211> LENGTH: 15
<212> TYPE: PRT
<213> ORGANISM: Artificial sequence
<220> FEATURE:
<223> OTHER INFORMATION: Sequence is synthesized

<400> SEQUENCE: 84

His Pro Cys Leu Glu Ser Val Gly Ala Leu Lys Ala Cys Met Tyr
 1               5                  10                  15

<210> SEQ ID NO 85
<211> LENGTH: 15
<212> TYPE: PRT
<213> ORGANISM: Artificial sequence
<220> FEATURE:
<223> OTHER INFORMATION: Sequence is synthesized

<400> SEQUENCE: 85

Asn Ser Cys Leu Glu Ser Val His Ala Leu Arg Glu Cys Met Leu
 1               5                  10                  15

<210> SEQ ID NO 86
<211> LENGTH: 15
<212> TYPE: PRT
<213> ORGANISM: Artificial sequence
<220> FEATURE:
<223> OTHER INFORMATION: Sequence is synthesized

<400> SEQUENCE: 86

Ala Gly Cys Leu Asp Ser Val Lys Ala Leu Lys Arg Cys Met Ile
 1               5                  10                  15

<210> SEQ ID NO 87
<211> LENGTH: 15
<212> TYPE: PRT
<213> ORGANISM: Artificial sequence
<220> FEATURE:
<223> OTHER INFORMATION: Sequence is synthesized

<400> SEQUENCE: 87

Tyr Thr Cys Phe Glu Ser Val Pro Ala Leu Arg Pro Cys Met Arg
 1               5                  10                  15

<210> SEQ ID NO 88
<211> LENGTH: 15
<212> TYPE: PRT
<213> ORGANISM: Artificial sequence
<220> FEATURE:
<223> OTHER INFORMATION: Sequence is synthesized

<400> SEQUENCE: 88

Tyr Thr Cys Phe Glu Ser Val Pro Ala Leu Arg Pro Cys Met Arg
 1               5                  10                  15

<210> SEQ ID NO 89
<211> LENGTH: 15
<212> TYPE: PRT
<213> ORGANISM: Artificial sequence
<220> FEATURE:
<223> OTHER INFORMATION: Sequence is synthesized

<400> SEQUENCE: 89

Ser His Cys Phe Asp Ser Val Arg Ala Leu Arg His Cys Met Arg
 1               5                  10                  15

<210> SEQ ID NO 90
<211> LENGTH: 15
<212> TYPE: PRT
<213> ORGANISM: Artificial sequence
<220> FEATURE:
<223> OTHER INFORMATION: Sequence is synthesized

<400> SEQUENCE: 90

Thr Ser Cys Phe Glu Ser Val Arg Ala Leu Arg Ala Cys Met Arg
 1               5                  10                  15

<210> SEQ ID NO 91
<211> LENGTH: 15
<212> TYPE: PRT
<213> ORGANISM: Artificial sequence
<220> FEATURE:
<223> OTHER INFORMATION: Sequence is synthesized -continued

```
<400> SEQUENCE: 91

Asn Ala Cys Leu Glu Ser Val Arg Ala Leu Lys Ala Cys Met Ser
  1               5                  10                  15

<210> SEQ ID NO 92
<211> LENGTH: 15
<212> TYPE: PRT
<213> ORGANISM: Artificial sequence
<220> FEATURE:
<223> OTHER INFORMATION: Sequence is synthesized

<400> SEQUENCE: 92

Leu Thr Cys Leu Asp Ser Val Arg Ala Leu Lys Glu Phe Met Leu
  1               5                  10                  15

<210> SEQ ID NO 93
<211> LENGTH: 15
<212> TYPE: PRT
<213> ORGANISM: Artificial sequence
<220> FEATURE:
<223> OTHER INFORMATION: Sequence is synthesized

<400> SEQUENCE: 93

Ser Lys Cys Leu Asp Ser Val Ser Ala Leu Arg Arg Cys Met Gln
  1               5                  10                  15

<210> SEQ ID NO 94
<211> LENGTH: 15
<212> TYPE: PRT
<213> ORGANISM: Artificial sequence
<220> FEATURE:
<223> OTHER INFORMATION: Sequence is synthesized

<400> SEQUENCE: 94

Arg Gly Cys Tyr Glu Ser Val Thr Ala Leu Arg His Cys Met Tyr
  1               5                  10                  15

<210> SEQ ID NO 95
<211> LENGTH: 15
<212> TYPE: PRT
<213> ORGANISM: Artificial sequence
<220> FEATURE:
<223> OTHER INFORMATION: Sequence is synthesized

<400> SEQUENCE: 95

Trp Arg Cys Ala Gln Asp Ala Gly Gly Trp Thr Tyr Cys Trp Ala
  1               5                  10                  15

<210> SEQ ID NO 96
<211> LENGTH: 15
<212> TYPE: PRT
<213> ORGANISM: Artificial sequence
<220> FEATURE:
<223> OTHER INFORMATION: Sequence is synthesized

<400> SEQUENCE: 96

Phe Arg Cys Ala Gly Asp Ala Gly Gly Arg Ser Tyr Cys Trp Asp
  1               5                  10                  15

<210> SEQ ID NO 97
<211> LENGTH: 15
<212> TYPE: PRT
<213> ORGANISM: Artificial sequence
<220> FEATURE:
<223> OTHER INFORMATION: Sequence is synthesized

<400> SEQUENCE: 97
```

Val Arg Cys Ala Tyr Asp Ala Gly Gly Ser Arg Tyr Cys Trp Glu
 1               5                  10                  15

<210> SEQ ID NO 98
<211> LENGTH: 15
<212> TYPE: PRT
<213> ORGANISM: Artificial sequence
<220> FEATURE:
<223> OTHER INFORMATION: Sequence is synthesized

<400> SEQUENCE: 98

Ala Arg Cys Ala Arg Asp Ala Gly Gly Phe Tyr Tyr Cys Trp Ala
 1               5                  10                  15

<210> SEQ ID NO 99
<211> LENGTH: 15
<212> TYPE: PRT
<213> ORGANISM: Artificial sequence
<220> FEATURE:
<223> OTHER INFORMATION: Sequence is synthesized

<400> SEQUENCE: 99

Ile Arg Cys Val Gln Asp Ala Gly Gly Val Arg Tyr Cys Trp Asp
 1               5                  10                  15

<210> SEQ ID NO 100
<211> LENGTH: 15
<212> TYPE: PRT
<213> ORGANISM: Artificial sequence
<220> FEATURE:
<223> OTHER INFORMATION: Sequence is synthesized

<400> SEQUENCE: 100

Val Arg Cys Val Ala Asp Ala Gly Gly Phe Leu Tyr Cys Trp Ala
 1               5                  10                  15

<210> SEQ ID NO 101
<211> LENGTH: 15
<212> TYPE: PRT
<213> ORGANISM: Artificial sequence
<220> FEATURE:
<223> OTHER INFORMATION: Sequence is synthesized

<400> SEQUENCE: 101

Trp Arg Cys Val Thr Asp Ala Gly Gly Arg Pro Tyr Cys Trp Ala
 1               5                  10                  15

<210> SEQ ID NO 102
<211> LENGTH: 15
<212> TYPE: PRT
<213> ORGANISM: Artificial sequence
<220> FEATURE:
<223> OTHER INFORMATION: Sequence is synthesized

<400> SEQUENCE: 102

Ala Ser Cys Val Ala Asp Ala Gly Gly Gly Gly Tyr Cys Trp Asp
 1               5                  10                  15

<210> SEQ ID NO 103
<211> LENGTH: 15
<212> TYPE: PRT
<213> ORGANISM: Artificial sequence
<220> FEATURE:
<223> OTHER INFORMATION: Sequence is synthesized

<400> SEQUENCE: 103

```
Val Asp Cys Val Trp Asp Ala His Gly Trp Gly Tyr Cys Trp Ala
 1               5                  10                  15
```

<210> SEQ ID NO 104
<211> LENGTH: 15
<212> TYPE: PRT
<213> ORGANISM: Artificial sequence
<220> FEATURE:
<223> OTHER INFORMATION: Sequence is synthesized

<400> SEQUENCE: 104

```
Val Thr Cys Ala Ala Asp Ala Leu Gly Phe Leu Tyr Cys Trp Glu
 1               5                  10                  15
```

<210> SEQ ID NO 105
<211> LENGTH: 15
<212> TYPE: PRT
<213> ORGANISM: Artificial sequence
<220> FEATURE:
<223> OTHER INFORMATION: Sequence is synthesized

<400> SEQUENCE: 105

```
Leu Arg Cys Thr Glu Asp Ala Ser Gly Arg Val Tyr Cys Trp Asp
 1               5                  10                  15
```

<210> SEQ ID NO 106
<211> LENGTH: 15
<212> TYPE: PRT
<213> ORGANISM: Artificial sequence
<220> FEATURE:
<223> OTHER INFORMATION: Sequence is synthesized

<400> SEQUENCE: 106

```
Gly Gly Cys Ala Ser Asp Leu Ala Gly Phe Arg Tyr Cys Trp Glu
 1               5                  10                  15
```

<210> SEQ ID NO 107
<211> LENGTH: 15
<212> TYPE: PRT
<213> ORGANISM: Artificial sequence
<220> FEATURE:
<223> OTHER INFORMATION: Sequence is synthesized

<400> SEQUENCE: 107

```
Leu Gly Cys Ala Ser Asp Leu Ala Gly Phe Trp Tyr Cys Trp Ala
 1               5                  10                  15
```

<210> SEQ ID NO 108
<211> LENGTH: 15
<212> TYPE: PRT
<213> ORGANISM: Artificial sequence
<220> FEATURE:
<223> OTHER INFORMATION: Sequence is synthesized

<400> SEQUENCE: 108

```
Tyr Arg Cys Ala Thr Asp Leu Ala Gly Phe Ser Tyr Cys Trp Ala
 1               5                  10                  15
```

<210> SEQ ID NO 109
<211> LENGTH: 15
<212> TYPE: PRT
<213> ORGANISM: Artificial sequence
<220> FEATURE:
<223> OTHER INFORMATION: Sequence is synthesized

<400> SEQUENCE: 109

```
Lys Gly Cys Val Ser Asp Leu Phe Gly Ala Gly Tyr Cys Trp Asp
```

```
                  1               5                  10                  15

<210> SEQ ID NO 110
<211> LENGTH: 15
<212> TYPE: PRT
<213> ORGANISM: Artificial sequence
<220> FEATURE:
<223> OTHER INFORMATION: Sequence is synthesized

<400> SEQUENCE: 110

Val Arg Cys Ala Trp Asp Leu Gly Gly Arg Ala Tyr Cys Trp Ala
  1               5                  10                  15

<210> SEQ ID NO 111
<211> LENGTH: 15
<212> TYPE: PRT
<213> ORGANISM: Artificial sequence
<220> FEATURE:
<223> OTHER INFORMATION: Sequence is synthesized

<400> SEQUENCE: 111

Leu Arg Cys Ala Glu Asp Leu Gly Gly Tyr Phe Tyr Cys Trp Ala
  1               5                  10                  15

<210> SEQ ID NO 112
<211> LENGTH: 15
<212> TYPE: PRT
<213> ORGANISM: Artificial sequence
<220> FEATURE:
<223> OTHER INFORMATION: Sequence is synthesized

<400> SEQUENCE: 112

Trp Arg Cys Val Asp Asp Leu Gly Gly Phe Gln Tyr Cys Trp Ala
  1               5                  10                  15

<210> SEQ ID NO 113
<211> LENGTH: 15
<212> TYPE: PRT
<213> ORGANISM: Artificial sequence
<220> FEATURE:
<223> OTHER INFORMATION: Sequence is synthesized

<400> SEQUENCE: 113

Val Lys Cys Ala Arg Asp Leu Ser Gly Phe Val Tyr Cys Trp Ala
  1               5                  10                  15

<210> SEQ ID NO 114
<211> LENGTH: 15
<212> TYPE: PRT
<213> ORGANISM: Artificial sequence
<220> FEATURE:
<223> OTHER INFORMATION: Sequence is synthesized

<400> SEQUENCE: 114

Gly Gly Cys Thr Gly Asp Ser Ala Gly Pro Gly Tyr Cys Trp Glu
  1               5                  10                  15

<210> SEQ ID NO 115
<211> LENGTH: 15
<212> TYPE: PRT
<213> ORGANISM: Artificial sequence
<220> FEATURE:
<223> OTHER INFORMATION: Sequence is synthesized

<400> SEQUENCE: 115

Arg Arg Cys Val Ser Asp Ser Gly Gly Arg Thr Tyr Cys Trp Ala
  1               5                  10                  15
```

<210> SEQ ID NO 116
<211> LENGTH: 15
<212> TYPE: PRT
<213> ORGANISM: Artificial sequence
<220> FEATURE:
<223> OTHER INFORMATION: Sequence is synthesized

<400> SEQUENCE: 116

Leu Lys Cys Ala Leu Asp Thr Phe Gly Gly Leu Tyr Cys Trp Ala
 1               5                  10                  15

<210> SEQ ID NO 117
<211> LENGTH: 15
<212> TYPE: PRT
<213> ORGANISM: Artificial sequence
<220> FEATURE:
<223> OTHER INFORMATION: Sequence is synthesized

<400> SEQUENCE: 117

Arg Lys Cys Ala Ser Asp Val Gly Gly Val Thr Tyr Cys Trp Asp
 1               5                  10                  15

<210> SEQ ID NO 118
<211> LENGTH: 15
<212> TYPE: PRT
<213> ORGANISM: Artificial sequence
<220> FEATURE:
<223> OTHER INFORMATION: Sequence is synthesized

<400> SEQUENCE: 118

Met Ser Cys Ala Arg Asp Val Arg Gly Val Arg Tyr Cys Trp Ala
 1               5                  10                  15

<210> SEQ ID NO 119
<211> LENGTH: 15
<212> TYPE: PRT
<213> ORGANISM: Artificial sequence
<220> FEATURE:
<223> OTHER INFORMATION: Sequence is synthesized

<400> SEQUENCE: 119

Gly Ala Cys Met Thr Asp Val Arg Gly Arg Glu Tyr Cys Trp Asp
 1               5                  10                  15

<210> SEQ ID NO 120
<211> LENGTH: 15
<212> TYPE: PRT
<213> ORGANISM: Artificial sequence
<220> FEATURE:
<223> OTHER INFORMATION: Sequence is synthesized

<400> SEQUENCE: 120

Phe Arg Cys Ala Trp Glu Leu Gly Trp Leu Tyr Val Leu Gly Leu
 1               5                  10                  15

<210> SEQ ID NO 121
<211> LENGTH: 16
<212> TYPE: PRT
<213> ORGANISM: Artificial sequence
<220> FEATURE:
<223> OTHER INFORMATION: Sequence is synthesized

<400> SEQUENCE: 121

Asp Glu Cys Leu Met Ser Val Glu Ala Leu Lys Asn Cys Met Gly
 1               5                  10                  15

-continued

```
Gly

<210> SEQ ID NO 122
<211> LENGTH: 16
<212> TYPE: PRT
<213> ORGANISM: Artificial sequence
<220> FEATURE:
<223> OTHER INFORMATION: Sequence is synthesized

<400> SEQUENCE: 122

Ala Arg Cys Val Val Asp Ala Gly Gly Thr Trp Tyr Cys Trp Ala
 1               5                  10                  15

Gly
```

IGF ANTAGONIST PEPTIDES

RELATED APPLICATIONS

This application is a non-provisional application filed under 37 CFR 1.53(b)(1), claiming priority under 35 USC 119(e) to provisional application No. 60/275,904 filed Mar. 14, 2001, the contents of which are incorporated herein by reference.

BACKGROUND OF THE INVENTION

1. Field of the Invention

This invention is directed to peptides that antagonize insulin-like growth factor (IGF), in particular, IGF-1. These peptides are useful in treating disorders caused or mediated by IGFs, such as cancer.

2. Description of Related Disclosures

There is a large body of literature on the actions and activities of IGFs (IGF-1, IGF-2, and IGF variants). Human IGF-1 is a 7649-dalton polypeptide with a pI of 8.4 (Rinderknecht and Humbel, *Proc. Natl. Acad. Sci. USA* 73:2365 (1976); Rinderknecht and Humbel, *J. Biol. Chem.* 253:2769(1978)) belonging to a family of somatomedins with insulin-like and mitogenic biological activities that modulate the action of growth hormone (GH) (Van Wyk et al., *Recent Prog. Horm. Res.* 30:259 (1974); Binoux, *Ann. Endocrinol*, 41:157 (198); Clemmons and Van Wyk, *Handbook Exp. Pharmacol.* 57:161 (1981); Baxter, *Adv. Clin. Chem.* 25:49 (186); U.S. Pat. No. 4,988,675; WO 91/03253; WO 93/23071). IGFs are structurally similar to insulin, and have been implicated as a therapeutic tool in a variety of diseases and injuries.

The IGF system is also composed of membrane-bound receptors for IGF-1, IGF-2, and insulin. The Type 1 IGF receptor (IGF-1 R) is closely related to the insulin receptor in structure and shares some of its signaling pathways (Jones and Clemmons, *Endocr. Rev.*, 16: 3–34 (1995)). The IGF-2 receptor is a clearance receptor that appears not to transmit an intracellular signal (Jones and Clemmons, supra). Since IGF-1 and IGF-2 bind to IGF-1 R with a much higher affinity than to the insulin receptor, it is most likely that most of the effects of IGF-1 and IGF-2 are mediated by IGF-1 R (Humbel, *Eur. J Biochem.* 190:445–462 (1990); Ballard et al., "Does IGF-1 ever act through the insulin receptor?", in Baxter et al. (Eds.), *The Insulin-Like Growth Factors and Their Regulatory Proteins*, (Amsterdam: Elsevier, 1994), pp. 131–138). The crystal structure of the first three domains of IGF-1 R has been determined (Garrett et al., *Nature*, 394, 395–399 (1998)).

IGF-1 R is a key factor in normal cell growth and development (Daughaday and Rotwein, *Endocrine Rev.*, 10:68–91 (1989)). Increasing evidence suggests, however, that IGF-1 R signaling also plays a critical role in growth of tumor cells, cell transformation, and tumorigenesis (Baserga, *Cancer Res.*, 55:249–252 (1995); for a review, see Khandwala et al., *Endocr. Rev.*, 21: 215–244 (2000)). Key examples include loss of metastatic phenotype of murine carcinoma cells by treatment with antisense RNA to the IGF-1 R (Long et al., *Cancer Res.*, 55:1006–1009 (1995)) and the in vitro inhibition of human melanoma cell motility (Stracke et al., *J. Biol. Chem.*, 264:21554–21559 (1989)) and of human breast cancer cell growth by the addition of IGF-1 R antibodies (Rohlik et al., *Biochem. Biophys. Res. Commun.*, 149:276–281 (1987)).

The IGFs are potent breast cancer cell mitogens based on the observation that IGF-1 enhanced breast cancer cell proliferation in vitro (Cullen et al., *Cancer Res.*, 50:48–53 (1990)). Breast cancers express IGF-2 and IGF-1 R, providing all the required effectors for an autocrine-loop-based proliferation paradigm (Quinn et al., *J. Biol. Chem.*, 271: 11477–11483 (1996); Steller et al., *Cancer Res.*, 56:1761–1765 (1996)). Because breast cancer is a common malignancy affecting approximately one in every eight women and is a leading cause of death from cancer in North American women (LeRoith et al., *Ann. Int. Med.*, 122:54–59 (1995)), new rational therapies are required for intervention. IGF-1 can suppress apoptosis, and therefore cells lacking IGF-1R or having compromised IGF-1 R signaling pathways may give rise to tumor cells that selectively die via apoptosis (Long et al., *Cancer Res.*, 55:1006–1009 (1995)). Furthermore, it has recently become evident that alterations in IGF signaling in the context of other disease states, such as diabetes, may be responsible for exacerbating the complications of retinopathy (Smith et al., *Science*, 276:1706–1709 (1997)) and nephropathy (Horney et al., *Am. J. Physiol.* 274: F1045–F1053 (1998)).

The IGF binding proteins (IGFBPs) are a family of at least six proteins (Jones and Clemmons, supra; Bach and Rechier, *Diabetes Reviews*, 3: 38–61 (1995)), that modulate access of the IGFs to the IGF-1 R. They also regulate the concentrations of IGF-1 and IGF-2 in the circulation and at the level of the tissue IGF-1 R (Clemmons et al., *Anal. NY Acad. Sci. USA*, 692:10–21 (1993)). The IGFBPs bind IGF-1 and IGF-2 with varying affinities and specificities (Jones and Clemmons, supra; Bach and Rechier, supra). For example, IGFBP-3 binds IGF-1 and IGF-2 with a similar affinity, whereas IGFBP-2 and IGFBP-6 bind IGF-2 with a much higher affinity than they bind IGF-1 (Bach and Rechier, supra; Oh et al., *Endocrinology*, 132, 1337–1344 (1993)).

In most cases, addition of exogenous IGFBP blunts the effects of IGF-1. For example, the growth-stimulating effect of estradiol on the MCF-7 human breast cancer cells is associated with decreased IGFBP-3 mRNA and protein accumulation, while the anti-estrogen ICI 182780 causes growth inhibition and increased IGFBP-3 mRNA and protein levels (Huynh et al., *J. Biol. Chem.*, 271:1016–1021 (1996); Oh et al., *Prog. Growth Factor Res.*, 6:503–5 12 (1995)). It has also been reported that the in vitro inhibition of breast cancer cell proliferation by retinoic acid may involve altered IGFBP secretion by tumor cells or decreased circulating IGF-1 levels in vivo (LeRoith et al., *Ann. Int. Med.*, 122:54–59 (1995); Oh et al., (1995), supra). Contrary to this finding, treatment of MCF-7 cells with the anti-estrogen tamoxifen decreases IGF-1 R signaling in a manner that is unrelated to decreased IGFBP production (Lee et al., *J. Endocrinol.*, 152:39 (1997)). Additional support for the general anti-proliferative effects of the IGFBPs is the striking finding that IGFBP-3 is a target gene of the tumor suppressor, p53 (Buckbinder et al., *Nature*, 377:646–649 (1995)). This suggests that the suppressor activity of p53 is, in part, mediated by IGFBP-3 production and the consequential blockade of IGF action (Buckbinder et al., supra). These results indicate that the IGFBPs can block cell proliferation by modulating paracrine/autocrine processes regulated by IGF-1/IGF-2. A corollary to these observations is the finding that prostate-specific antigen (PSA) is an IGFBP-3-protease, which upon activation, increases the sensitivity of tumor cells to the actions of IGF-1/IGF-2 due to the proteolytic inactivation of IGFBP-3 (Cohen et al., *J. Endocr.*, 142:407–415 (1994)). The IGFBPs complex with IGF-1/IGF-2 and interfere with the access of IGF-1/IGF-2 to IGF-1Rs (Clemmons et al., *Anal. NY Acad. Sci. USA*, 692:10–21 (1993)). IGFBP-1, -2 and -3 inhibit cell growth following addition to cells in vitro (Lee et al., *J Endocrinol.*, 152:39 (1997); Feyen et al., *J. Biol. Chem.*, 266:19469–19474 (1991)). Further, IGFBP-1 (McGuire et al., *J. Natl. Cancer Inst.*, 84:1335–1341(1992); Figueroa et al., *J Cell Physiol.*, 157:229–236 (1993)), IGFBP-3 (Oh et al. (1995), supra; Pratt and Pollak, *Biophys. Res. Commun.*, 198:292–297 (1994)) and IGFBP-2 have all been shown to inhibit IGF-1 or estrogen-induced breast cancer cell proliferation at nanomolar concentrations in vitro. These findings support the idea that the IGFBPs are potent antagonists of IGF action. There is also evidence for a direct effect of IGFBP-3 on cells through its own cell surface receptor, independent of IGF interactions (Oh et al., *J. Biol. Chem.*, 268:14964–14971 (1993); Valentinis et al., *Mol. Endocrinol.*, 9:361–367 (1995)). Taken together, these findings underscore the importance of IGF and IGF-1 R as targets for therapeutic use.

Unlike most other growth factors, the IGFs are present in high concentrations in the circulation, but only a small fraction of the IGFs is not protein bound. For example, it is generally known that in humans or rodents, less than 1% of the IGFs in blood is in a "free" or unbound form (Juul et al., *Clin. Endocrinol.*, 44: 515–523 (1996); Hizuka et al., *Growth Regulation*, 1: 51–55 (1991Hasegawa et al., *J. Clin. Endocrinol. Metab.*, 80: 3284–3286 (1995)). The overwhelming majority of the IGFs in blood circulate as part of a non-covalently associated ternary complex composed of IGF-1 or IGF-2, IGFBP-3, and a large protein termed the acid-labile subunit (ALS). This complex is composed of equimolar amounts of each of the three components. The ternary complex of an IGF, IGFBP-3, and ALS has a molecular weight of approximately 150,000 daltons, and it has been suggested that the function of this complex in the circulation may be to serve as a reservoir and buffer for IGF-1 and IGF-2, preventing rapid changes in free IGF-1 or IGF-2.

Maintaining normal levels of IGF-1 signaling are important for proper cellular function, since both down-and up-regulation of IGF-1-related pathways have been implicated in several human diseases. The rate of cell proliferation is positively correlated with risk of transformation of certain epithelial cell types (Cohen and Ellwein, *Science*, 249: 1007 (1990); Cohen and Ellwein, *Cancer Research*, 51:6493 (1991)). Relatively high plasma IGF-1 and low IGF binding protein-3 levels are associated with greater risk of breast cancer in pre-menopausal women, prostate cancer in men, colorectal cancer in men and women, and lung cancer in men and women; additional in vitro and in vivo studies reflecting a link between IGF and cancer are found in "Insulin-Like Growth Factors and Cancer", *Cytokine Bulletin*, R&D Systems (Fall 2000 edition), pages 2–3. IGFs have mitogenic and anti-apoptotic influences on normal and transformed prostate epithelial cells (Hsing et al., *Cancer Research*, 56: 5146 (1996); Culig et al., *Cancer Research*, 54: 5474 (1994); Cohen et al., *Hormone and Metabolic Research*, 26: 81 (1994); Iwamura et al., *Prostate*, 22: 243 (1993); Cohen et al., *J. Clin. Endocrin. & Metabol.*, 73: 401 (1991); Rajah et al., *J. Biol. Chem.*, 272: 12181 (1997)). Most circulating IGF-1 originates in the liver, but IGF bioactivity in tissues is related not only to levels of circulating IGFs and IGFBPs, but also to local production of IGFs, IGFBPs, and IGFBP proteases (Jones and Clemmons, *Endocrine Reviews*, 16: 3 (1995)). Person-to-person variability in levels of circulating IGF-1 and IGFBP-3 (the major circulating IGFBP (Jones and Clemmons, supra)) is considerable (Juul et al., *J. Clin. Endocrinol. & Metabol.*, 78: 744 (1994); Juul et al., *J. Clin. Endocrinol. & Metabol.*, 80: 2534 (1995)), and heterogeneity in serum IGF-1 level appears to reflect heterogeneity in tissue IGF bioactivity. Markers relating to IGF-axis components can be used as a risk marker for prostate cancer, as PSA is likewise used (WO 99/38011). Further, it has been found that reduced IGF-1 concentrations in serum correlate with improved clinical scores in acromegaly patients (Trainer et al., *New England J. Med.*, 342: 1171–1177 (2000)).

There has been much work identifying the regions on IGF-1 and IGF-2 that bind to the IGFBPs (Bayne et al., *J. Biol. Chem.*, 265: 15648–15652 (1990); Dubaquic and Lowman, *Biochemistry*, 38: 6386–6396 (1999); and U.S. Pat. Nos. 5,077,276; 5,164,370; and 5,470,828). For example, it has been discovered that the N-terminal region of IGF-1 and IGF-2 is critical for binding to the IGFBPs (U.S. Pat. Nos. 5,077,276; 5,164,370; and 5,470,828). Thus, the natural IGF-1 variant, designated des (1–3) IGF-1, binds poorly to IGFBPs.

A similar amount of research has been devoted to identifying the regions on IGF-1 and IGF-2 that bind to IGF-1 R (Bayne et al., supra; Oh et al., *Endocrinology* (1993), supra). It was found that the tyrosine residues in IGF-1 at positions 24, 31, and 60 are crucial to the binding of IGF-1 to IGF-1 R (Bayne et al., supra). Mutant IGF-1 molecules where one or more of these tyrosine residues are substituted showed progressively reduced binding to IGF-1 R. Bayne et al., supra, also investigated whether such mutants of IGF-1 could bind to IGF-1 R and to the IGFBPs. They found that quite different residues on IGF-1 and IGF-2 are used to bind to the IGFBPs from those used to bind to IGF-IR. It is therefore possible to produce IGF variants that show reduced binding to the IGFBPs, but, because they bind well to IGF-1 R, show maintained activity in in vitro activity assays.

Also reported was an IGF variant that binds to IGFBPs but not to IGF receptors and therefore shows reduced activity in in vitro activity assays (Bar et al., *Endocrinology*, 127: 3243–3245 (1990)). In this variant, designated (1–27, gly$^4$, 38–70)-hIGF-1, residues 28–37 of the C region of human IGF-1 are replaced by a four-residue glycine bridge.

Other truncated IGF-1 variants are disclosed. For example, in the patent literature, WO 96/33216 describes a truncated variant having residues 1–69 of authentic IGF-1. EP 742,228 discloses two-chain IGF-1 superagonists, which are derivatives of the naturally occurring, single-chain IGF-1 having an abbreviated C region. The IGF-1 analogs are of the formula: BC",A wherein B is the B region of IGF-1 or a functional analog thereof, C is the C region of IGF-1 or a functional analog thereof, n is the number of amino acids in the C region and is from about 6 to about 12, and A is the A region of IGF-1 or a functional analog thereof.

Additionally, Cascieri et al., *Biochemistry*, 27: 3229–3233 (1988) discloses four mutants of IGF-1, three of which have reduced affinity to IGF-1 R. These mutants are: (Phe$^{23}$, Phe$^{24}$,Tyr$^{25}$)IGF-1 (which is equipotent to human IGF-1 in its affinity to the Types 1 and 2 IGF and insulin receptors), (Leu$^{24}$)IGF-1 and (Ser 24)IGF-1 (which have a lower affinity than IGF-1 to the human placental IGF-1 R, the placental insulin receptor, and the IGF-1 R of rat and mouse cells), and desoctapeptide (Leu$^{24}$)IGF-1 (in which the loss of aromaticity at position 24 is combined with the deletion of the carboxyl-terminal D region of hIGF-1, which has lower affinity than (Leu$^{24}$) IGF-1 for the IGF-1 R and higher affinity for the insulin receptor). These four mutants have normal affinities for human serum binding proteins.

Bayne et al., *J. Biol. Chem.*, 263: 6233–6239 (1988) discloses foul structural analogs of human IGF-1: a B-chain mutant in which the first 16 amino acids of IGF-1 were replaced with the first 17 amino acids of the B-chain of insulin, (Gln$^3$,Ala$^4$)IGF-1, (Tyr$^{15}$,Leu$^{16}$)IGF-1, and (Gln$^3$, Ala$^4$,Tyr$^{15}$,Leu$^{16}$)IGF-1. These studies identify some of the regions of IGF-1 that are responsible for maintaining high-affinity binding with the serum binding protein and the Type 2 IGF receptor.

In another study, Bayne et al., *J. Biol. Chem.*, 264: 11004–11008 (1988) discloses three structural analogs of IGF-1: (1–62)IGF-1, which lacks the carboxyl-terminal 8-amino-acid D region of IGF-; (1–27,Gly$^4$,38–70)IGF-1, in which residues 28–37 of the C region of IGF-1 are replace four-residue glycine bridge; and (1–27,Gly$^4$,38–62)IGF-1, with a C region glycine replacement and a D region deletion. Peterkofsky et al., *Endocrinology*, 128: 1769–1779 (1991) discloses data using the Gly$^4$ mutant of Bayne et al., supra (vol. 264).

Cascieri et al., *J. Biol. Chem.*, 264: 2199–2202 (1989) discloses three IGF-1 analogs in which specific residues in the A region of IGF-1 are replaced with the corresponding residues in the A chain of insulin. The analogs are: (Ile$^{48}$, Glu$^{45}$,Gln$^{46}$,Thr$^{49}$,Ser$^{50}$,Ile$^{51}$,Ser$^{53}$,Tyr$^{55}$ Gln$^{56}$)IGF-1, an A-chain mutant in which residue 41 is changed from threonine to isoleucine and residues 42–56 of the A region are replaced; (Thr$^{49}$,Ser$^{50}$,Ile$^{51}$)IGF-1; and (Tyr$^{55}$,Gln$^{56}$)IGF-1.

Clemmons et al., *J. Biol. Chem.*, 265: 12210–12216 (1990) discloses use of IGF-1 analogs that have reduced binding affinity for either IGF-1 R or binding proteins to study the ligand specificity of IGFBP-1 and the role of IGFBP-1 in modulating the biological activity of IGF-1.

WO 94/04569 discloses a specific binding molecule, other than a natural IGFBP, that is capable of binding to IGF-1 and can enhance the biological activity of IGF-1.

The direction of research into IGF variants has mostly been to make IGF variants that do not bind to the IGFBPs, but show maintained binding to the IGF receptor. The idea behind the study of such molecules is that the major actions of the IGFBPs are proposed to be an inhibition of the activity of the IGFs. Chief among these variants is the natural molecule, des(1–3)IGF-1, which shows selectively reduced affinity for some of the IGF binding proteins, yet a maintained affinity for the IGF receptor (U.S. Pat. Nos. 5,077, 276; 5,164,370; 5,470,828).

Peptides that bind to IGFBP-1, block IGF-1 binding to this binding protein, and thereby release "free-IGF" activity from mixtures of IGF-1 and IGFBP-1 have been recently described (Lowman et al., *Biochemistry*, 37: 8870–8878 (1998); WO 98/45427 published Oct. 15, 1998; Lowman et al., International Pediatric Nephrology Association, Fifth Symposium on Growth and Development in Children with Chronic Renal Failure (New York, Mar. 13, 1999)).

Exploitation of the interaction between IGF and IGFBP in screening, preventing, or treating disease has been limited, however, because of a lack of specific antagonists. To date, only one publication is known to exist that describes the application of an IGF-1/IGF-2 antagonist as a potential therapeutic adjunct in the treatment of cancer (Pietrzkowski et al., *Cancer Res.*, 52: 6447–6451 (1992)). In that report, a peptide corresponding to the D-region of IGF-1 was synthesized for use as an IGF-1/2 antagonist. This peptide exhibited questionable inhibitory activity against IGF-1. The basis for the observed inhibition is unclear as the D-region does not play a significant role in IGF-1 R binding but rather, in IGF-1 binding to the insulin receptor (Cooke et al., *Biochem.*, 30:5484–5491 (1991); Bayne et al., *J. Biol. Chem.*, 264:11004–11008 (1988); Yee et al., *Cell Growth and Different.*, 5:73–77 (1994)). IGF antagonists whose mechanism of action is via blockade of interactions at the IGF-1R interface may also significantly alter insulin action at the insulin receptor, a disadvantage of such antagonists.

Recently, certain IGF-1 antagonists have been described by WO 00/23469, which discloses the portions of IGFBP and IGF peptides that account for IGF-1 GFBP binding, i.e., an isolated IGF binding domain of an IGFBP or modification thereof that binds IGF with at least about the same binding affinity as the full-length IGFBP. The patent publication also discloses an IGF antagonist that reduces binding of IGF to an IGF receptor, and/or binds to a binding domain of IGFBP. Disclosed uses of such antagonists and fragments are in treating a subject having cancer and preventing cancer in a subject, treating a subject with a diabetic complication exacerbated by IGF and preventing diabetic complications exacerbated by IGF, or treating a subject with an ischemic injury or preventing an ischemic injury in a subject.

Additionally, EP 639981 discloses pharmaceutical compositions comprising short peptides that function as IGF-1 receptor antagonists. The peptides used in the pharmaceutical compositions consist of less than 25 amino acids, comprise at least a portion of the C or D region from IGF-1, and inhibit IGF-1-induced autopliosphorylation of IGF-1 receptors. Methods of inhibiting cell proliferation and of treating individuals suspected of suffering from or susceptible to diseases associated with undesirable cell proliferation such as cancer, restenosis and asthma are disclosed.

Generation of specific IGF-1 antagonists has been restricted, at least in part, because of difficulties in studying the structure of IGF and IGFBP. Due to the inability to obtain crystals of IGF-1 suitable for diffraction studies, for example, an extrapolation of IGF-1 structure based on the crystal structure of porcine insulin was the most important structural road map for IGF-1 available (Blundell et al., *Proc. Natl. Acad. Sci. USA*, 75:180–184 (1978)). See also Blundell et al., *Fed Proc.*, 42: 2592 (1983), which discloses tertiary structures, receptor binding, and antigenicity of IGFs. Based on studies of chemically modified and mutated IGF-1, a number of common residues between IGF-1 and insulin have been identified as being part of the IGF-1R-insulin receptor contact site, in particular the aromatic residues at positions 23–25. Using NMR and restrained molecular dynamics, the solution structure of IGF-1 was recently reported (Cooke et al., supra). The resulting minimized structure was shown to better fit the experimental findings on modified IGF-1, as well as the extrapolations made from the structure-activity studies of insulin. Further, De Wolf et al., *Protein Sci.*, 5: 2193 (1996) discloses the solution structure of a mini-IGF-1. Sato et al., *Int. J. Pept.*, 41: 433(1993) discloses the three-dimensional structure of IGF-1 determined by 1 H-NMR and distance geometry. Torres et al., *J Mol. Biol.*, 248: 385 (1995) discloses the solution structure of human IGF-2 and its relationship to receptor and binding protein interactions. Laajoki et al., *J. Biol. Chem.*, 275: 10009 (2000) discloses the solution structure and backbone dynamics of long-[Arg(3)]IGF-1.

Peptide sequences capable of binding to insulin and/or insulin-like growth factor receptors with either agonist or antagonist activity and identified from various peptide libraries are described in WO 01/72771 published Oct. 4, 2001.

There is a continuing need in the art for a molecule that acts as an IGF antagonist to control the levels of circulating IGF as well as receptor response, for therapeutic or diagnostic purposes.

SUMMARY OF THE INVENTION

Accordingly, the invention is as claimed. In one aspect the invention provides a peptide of family 1 comprising the sequence:

$(Xaa)_1(Xaa)_2Cys(Xaa)_3(Xaa)_4SerVal(Xaa)_5AlaLeu(Xaa)_6(Xaa)_7CysMet(Xaa)_8$ (SEQ ID NO:1) where $(Xaa)_1$, $(Xaa)_2$, and $(Xaa)_7$ are any amino acid, $(Xaa)_3$ is Phe, Leu, or Tyr, $(Xaa)_4$ is Glu, Asp, Ala, Gly, Thr, or Ser, $(Xaa)_5$ is Glu, Asp, Ala, or Gly, $(Xaa)_6$ is Arg or Lys, and $(Xaa)_8$ is Tyr or Arg. $(Xaa)_4$ is Glu, Ala, Gly, Thr, or Ser, $(Xaa)_5$ is Glu, Ala, or Gly, and $(Xaa)_8$ is Tyr. The preferred peptides of the above sequence are such that $(Xaa)_4$ is Glu, Ala or Thr, $(Xaa)_5$ is Ala or Gly, and Xaa8 is Tyr. More preferred are the peptides wherein $(Xaa)_4$ is Glu or Ala, $(Xaa)_5$ is Ala or Gly, and $(Xaa)_8$ is Tyr. Still more preferred are the peptides comprising the sequence RNCFESVAALRRCMYG (SEQ ID NO:2), MDCLASVEALKWCMYG (SEQ ID NO:3), or FECLTSVEALRGCMYG (SEQ ID NO:4). Most preferred are peptides that comprise SEQ ID NO:2 or 3.

In another aspect, the invention provides a peptide of family 2 comprising the sequence:

$(Xaa)_1(Xaa)_2Cys(Xaa)_3(Xaa)_4Asp(Xaa)_5(Xaa)_6Gly(Xaa)_7(Xaa)_8TyrCysTrp(Xaa)_9$ (SEQ ID NO:5 where $(Xaa)_1$, $(Xaa)_4$, and $(Xaa)_8$ are any amino acid, $(Xaa)_2$ is Arg, Lys, Gly, Ser, or Thr, $(Xaa)_3$ is Ala or Val, $(Xaa)_5$ is Ala or Leu, $(Xaa)_6$ is Ala, Gly, or Leu, $(Xaa)_7$ is Phe, Tyr, Trp, or Gly, and $(Xaa)_9$ is Glu, Asp, Ala, or Gly. The preferred peptides herein are such that $(Xaa)_2$ is Gly, Ser, Arg, or Thr, and $(Xaa)_9$ is Glu, Ala, or Asp. More preferred are peptides wherein $(Xaa)_2$ is Glu or Arg, $(Xaa)_5$ is Leu, $(Xaa)_6$ is Ala or Gly, $(Xaa)_7$ is Phe, and $(Xaa)_9$ is Ala. The most preferred of this family of peptides are those that comprise the sequence LGCASDLAGFWYCWAG (SEQ ID NO:6) or WRCVDDLGGFQYCWAG (SEQ ID NO:7).

Preferably, all the amino acids in these two families of peptides are L-amino acids. Also preferred is that these families of peptides comprise a glycine residue after $(Xaa)_8$ for family 1 above or after $(Xaa)_9$ for family 2 above.

The invention also provides conjugates comprising the peptide conjugated with a cytotoxic agent or polyethylene glycol. The cytotoxic agent here may be one that is active in killing cells once internalized.

Uses of these peptides include all uses that antagonize at least one biological activity of exogenous or endogenous IGFs. They can be used in treating, inhibiting, or preventing conditions in which an IGF antagonist such as IGFBP-3 or antibodies to IGF-1 is useful, as described below.

The invention also provides a composition comprising one of the peptides described above in a carrier. Preferably, this composition is sterile and (he carrier is a pharmaceutically acceptable carrier. Also preferred is the composition further comprising an angiogenic agent or chemotherapeutic agent, and also one that is suitable for injection or inhalation. A kit is also provided comprising a container containing the composition and instructions directing the user to utilize the composition.

In another aspect, the invention provides a method for treating a mammal having a disorder involving an IGF-1-mediated event comprising administering to the mammal an effective amount of any of the peptides or compositions described above. More specifically, the invention provides a method of treating a mammal suffering from, or predisposed to, a disease or disorder involving an IGF-1-mediated event, comprising administering to the mammal a therapeutically effective amount of a peptide as disclosed herein, or of a composition comprising the peptide and a pharmaceutically acceptable carrier. Preferably, this method further comprises administering to the mammal an effective amount of another agent that treats said disorder. This agent may be a growth inhibitory agent, an angiostatic agent, or a cytotoxic agent, or a chemotherapeutic agent or an antibody. In another preferred aspect, the mammal is human.

In a further preferred embodiment, before the administration step of the above method, the concentration of IGF-1 in a body sample from the mammal is measured, wherein an elevated concentration of IGF-1 above a reference range for IGF-1 indicates an increased risk for the disorder. The body sample is preferably selected from the group consisting of tumor tissue, blood, plasma, serum, mammary fluid, and seminal fluid. In another preferred embodiment, the IGF-1 is total IGF-1, free IGF-1 or complexed IGF-1, and the disorder is cancer, a diabetic complication exacerbated by IGF-1, preferably diabetic retinopathy or diabetic nephropathy, acromegaly, age-related macular degeneration, ischemic injury, or a trauma.

If the disorder is cancer, preferably it comprises a tumor that expresses an insulin-like growth factor receptor. Further, the cancer is preferably breast cancer, prostate cancer, colorectal cancer, or lung cancer, more preferably breast or prostate cancer. If the disorder is prostate cancer the process preferably comprises, before the administration step, measuring the concentration of PSA in a body sample from the mammal, wherein an elevated concentration of PSA above a reference range for PSA indicates an increased risk for prostate cancer. Alternatively, if the disorder is prostate cancer, the method preferably comprises, before the administration step, measuring the concentration of IGF-1 in a body sample from the mammal, measuring the concentration of IGFBP-3 in a body sample from the mammal and conducting a multivariate adjustment of the IGF-1 concentration relative to the IGFBP-3 concentration to provide an adjusted IGF-1 level, wherein the adjusted IGF-1 level above a reference range for adjusted IGF-1 indicates an increased risk for prostate cancer. Still alternatively, if the disorder is prostate cancer, the method preferably comprises, before the administration step, measuring the concentration of IGF-1 in a body sample from the mammal, measuring the concentration of IGFBP-3 in a body sample from the mammal, measuring the concentration of PSA in a body sample from the mammal, and conducting a multivariate adjustment of the IGF-1 concentration relative to the IGFBP-3 concentration and PSA concentration to provide an adjusted IGF/IGFBP/PSA value, wherein an adjusted IGF/IGFBP/PSA value above a reference range for adjusted IGF/IGFBP/PSA indicates an increased risk for severe prostate cancer.

The present invention further provides various dosage forms of any of the peptides of the present invention, including but not limited to, those suitable for parenteral, oral, rectal and pulmonary administration of a peptide. In preferred aspects herein a therapeutic dosage form is provided suitable for inhalation and the invention provides for the therapeutic treatment of diseases or disorders involving an IGF-mediated or associated process or event via pulmonary administration of a peptide of the invention. More particularly, the invention is directed to pulmonary administration of the peptides herein by inhalation. Thus, the present invention provides an aerosol formulation comprising an amount of a peptide of the invention, effective to block or prevent an IGF-mediated or associated process or event and a dispersant. In one embodiment, any one of the above peptides can be provided in a liquid aerosol formulation. Alternatively, the peptide can be provided as a dry powder aerosol formulation. Therefore, according to the present invention, formulations are provided that provide an effective non-invasive alternative to other parenteral routes of administration of the peptides herein for the treatment of IGF-mediated or associated events.

Isolated nucleic acid encoding one of the above peptides herein is also provided, and may be used for in vivo or ex vivo gene therapy.

BRIEF DESCRIPTION OF THE DRAWINGS

FIG. 1 shows the three-dimensional minimized mean structure of the peptide IGF-F1-1 in solution calculated using restraints derived from NMR data. The backbone fold is depicted as a ribbon, and all side-chains' heavy atoms arc shown; several side-chains arc labeled.

DESCRIPTION OF THE PREFERRED EMBODIMENTS

A. Definitions

As used herein, "mammal" for purposes of treatment refers to any animal classified as a mammal, including humans, domestic, and farm animals, and zoo, sports, or pet animals, such as dogs, horses, cats, sheep, pigs, cows, etc. The preferred mammal herein is a human. The term "non-adult" refers to mammals that are from perinatal age (such as low-birth-weight infants) up to the age of puberty, the latter being those that have not yet reached full growth potential.

As used herein, "IGF" refers to native insulin-like growth factor-1 and native insulin-like growth factor-2 as well as natural variants thereof such as brain IGF, otherwise known as des(1–3)IGF-1.

As used herein, "IGF-1" refers to insulin-like growth factor-1 from any species, including bovine, ovine, porcine, equine, and human, preferably human, and, if referring to exogenous administration, from any source, whether natural, synthetic, or recombinant. Human native-sequence, mature IGF-1, more preferably without a N-terminal methionine is prepared, e.g., by the process described in EP 230,869 published Aug. 5, 1987; EP 128,733 published Dec. 19, 1984; or EP 288,451 published Oct. 26, 1988. More preferably, this native-sequence IGF-1 is recombinantly produced and is available from Genentech, Inc., South San Francisco, Calif. for clinical investigations.

As used herein, "IGF-2" refers to insulin-like growth factor-2 from any species, including bovine, ovine, porcine, equine, and human, preferably human, and, if referring to exogenous administration, from any source, whether natural, synthetic, or recombinant. It may be prepared by the method described in, e.g., EP 128,733, supra.

An "IGFBP" or an "IGF binding protein" refers to a protein or polypeptide normally associated with or bound or complexed to IGF-1 or IGF-2, whether or not it is circulatory (i.e., in serum or tissue). Such binding proteins do not include receptors. This definition includes IGFBP-1, IGFBP-2, IGFBP-3, IGFBP-4, IGFBP-5, IGFBP-6, Mac 25 (IGFBP-7), and prostacyclin-stimulating factor (PSF) or endothelial cell-specific molecule (ESM-1), as well as other proteins with high homology to IGFBPs. Mac 25 is described, for example, in Swisshelm et al., *Proc. Natl. Acad. Sci. USA,* 92: 4472–4476 (1995) and Oh et al., *J. Biol. Chem.,* 271: 30322–30325 (1996). PSF is described in Yamauchi et al., *Biochemical Journal,* 303: 591–598 (1994). ESM-1 is described in Lassalle et al., *J. Biol. Chem.,* 271: 20458–20464 (1996). For other identified IGFBPs, see, e.g., EP 375,438 published 27 Jun. 1990; EP 369,943 published 23 May 1990; WO 89/09268 published 5 Oct. 1989; Wood et al., *Molecular Endocrinology,* 2: 1176–1185 (1988); Brinkman et al., *The EMBO J.,* 7: 2417–2423 (1988); Lee et al., *Mol. Endocrinol.,* 2: 404–411 (1988); Brewer et al., *BBRC,* 152: 1289–1297 (1988); EP 294,021 published 7 Dec. 1988; Baxter et al., *BBRC,* 147: 408–415 (1987); Leung et al., *Nature,* 330: 537–543 (1987); Martin et al., *J. Biol. Chem.,* 261: 8754–8760 (1986); Baxter et al., *Comp. Biochem. Physiol.,* 91B: 229–235 (1988); WO 89/08667 published 21 Sep. 1989; WO 89/09792 published 19 Oct. 1989; and Binkert et al., *EMBO J.,* 8: 2497–2502 (1989).

The term "body sample" refers to a biological specimen from a mammal, preferably from a human, including tissues, cells, and body fluid. Examples include tumor tissue, tumor cells, serum, plasma, lymph fluid, synovial fluid, follicular fluid, seminal fluid, amniotic fluid, milk, mammary fluid, whole blood, urine, spinal fluid, saliva, sputum, tears, perspiration, mucus, tissue culture medium, tissue extracts, and cellular extracts. Preferably, the body sample is tumor tissue, blood, plasma, serum, mammary fluid, or seminal fluid.

As used herein, "human IGF receptor" refers to any receptor for an IGF found in humans and includes the Type 1 and Type 2 IGF receptors in humans to which both human IGF-1 and IGF-2 bind, such as the placental IGF-1R, etc.

The term "amino acid" within the scope of the present invention is used in its broadest sense and is meant to include the naturally-occurring L $\alpha$-amino acids or residues. The commonly used one- and three-letter abbreviations for naturally-occurring amino acids are used herein (Lehninger, *Biochemistry,* 2d ed., pp. 71–92, (Worth Publishers: New York, 1975). The term includes D-amino acids as well as chemically-modified amino acids such as amino acid analogs, naturally-occurring amino acids that are not usually incorporated into proteins such as norleucine, and chemically-synthesized compounds having properties known in the art to be characteristic of an amino acid. For example, analogs or mimetics of phenylalanine or proline, which allow the same confrontational restriction of the peptide compounds as natural Phe or Pro, are included within the definition of amino acid. Such analogs and mimetics are referred to herein as "functional equivalents" of an amino acid. Other examples of amino acids are listed by Roberts and Vellaccio, *The Peptides: Analysis, Synthesis, Biology*, Eds. Gross and Meiehofer, Vol. 5, p. 341 (Academic Press, Inc.: N.Y. 1983).

The term "conservative" amino acid substitution as used herein to refer to amino acid substitutions that substitute functionally-equivalent amino acids. Conservative amino acid changes result in silent changes in the amino acid sequence of the resulting peptide. For example, one or more amino acids of a similar polarity act as functional equivalents and result in a silent alteration within the amino acid sequence of the peptide. The largest sets of conservative amino acid substitutions include:

(1) hydrophobic: His, Trp, Tyr, Phe, Met, Leu, lie, Val, Ala;
(2) neutral hydrophilic: Cys, Ser, Thr;
(3) polar: Ser, Thr, Asn, Gln;
(4) acidic/negatively charged: Asp, Glu;
(5) charged: Asp, Glu, Arg, Lys, His;
(6) basic/positively charged: Arg, Lys, His;
(7) basic: Asn, Gln, His, Lys, Arg;
(8) residues that influence chain orientation: Gly, Pro; and
(9) aromatic: Trp, Tyr, Phe, His.

In addition, "structurally-similar" amino acids can substitute conservatively for some of the specific amino acids.

Groups of structurally-similar amino acids include: (Ile, Leu, and Val); (Phe and Tyr); (Lys and Arg); (Gln and Asn); (Asp and Glu); and (Gly and Ala). In this regard, it is understood that amino acids are substituted on the basis of side-chain bulk, charge, and/or hydrophobicity. Amino acid residues are classified into four major groups:

Acidic: The residue has a negative charge due to loss of an H ion at physiological pH and the residue is attracted by aqueous solution so as to seek the surface positions in the conformation of a peptide in which it is contained when the peptide is in aqueous solution.

Basic: The residue has a positive charge due to association with an H ion at physiological pH and the residue is attracted by aqueous solution so as to seek the surface positions in the conformation of a peptide in which it is contained when the peptide is in aqueous medium at physiological pH.

Neutral/non-polar: The residues are not charged at physiological pH and the residue is repelled by aqueous solution so as to seek the inner positions in the conformation of a peptide in which it is contained when the peptide is in aqueous medium. These residues are also designated "hydrophobic residues."

Neutral/polar: The residues are not charged at physiological pH, but the residue is attracted by aqueous solution so as to seek the outer positions in the conformation of a peptide in which it is contained when the peptide is in aqueous medium.

"Amino acid" residues can be further classified as cyclic or non-cyclic, and aromatic or non-aromatic with respect to their side-chain groups, these designations being commonplace to the skilled artisan. The table below shows the types of conservative substitutions that can be made.

| Original Residue | Exemplary Conservative Substitution | Preferred Conservative Substitution |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn | Asn |
| Glu | Asp | Asp |
| Gly | Pro | Pro |
| His | Asn, Gln, Lys, Arg | Arg |
| Ile | Leu, Val, Met, Ala Phe | Leu |
| Leu | Ile, Val Met, Ala, Phe | Ile |
| Lys | Arg, Gln, Asn | Arg |
| Met | Leu, Phe, Ile | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe Ala | Leu |

Peptides synthesized by the standard solid-phase synthesis techniques described herein, for example, are not limited to amino acids encoded by genes for substitutions involving the amino acids. Commonly-encountered amino acids that are not encoded by the genetic code include, for example, those described in WO 90/01940 and in the table below, as well as, for example, 2-amino adipic acid (Aad) for Glu and Asp; 2-aminopimelic acid (Apm) for Glu and Asp; 2-aminobutyric (Abu) acid for Met, Leu, and other aliphatic amino acids; 2-aminoheptanoic acid (Ahe) for Met, Leu, and other aliphatic amino acids; 2-aminoisobutyric acid (Aib) for Gly; cyclohexylalanine (Cha) for Val, Leu and Ile; homoarginine (Har) for Arg and Lys; 2,3-diaminopropionic acid (Dpr) for Lys, Arg, and His; N-ethylglycine (EtGly) for Gly, Pro, and Ala; N-ethylglycine (EtGly) for Gly, Pro, and Ala; N-ethylasparagine (EtAsn) for Asn, and Gln; hydroxylysine (Hyl) for Lys; allohydroxylysine (AHyl) for Lys; 3-(and 4-)hydroxyproline (3Hyp, 4Hyp) for Pro, Ser, and Thr; alloisoleucine (AIle) for Ile, Leu, and Val; ρ-amidinophenylalanine for Ala; N-methylglycine (MeGly, sarcosine) for Gly, Pro, and Ala; N-methylisoleucine (MeIle) for Ile; norvaline (Nva) for Met and other aliphatic amino acids; norleucine (Nle) for Met and other aliphatic amino acids; ornithine (Orn) for Lys, Arg and His; citruline (Cit) and methionine sulfoxide (MSO) for Thr, Asn, and Gln; and N-methylphenylalanine (MePhe), trimethylphenylalanine, halo-(F-, Cl-, Br-, or I-)phenylalanine, or trifluorylphenylalanine for Phe.

| Abbreviations used in the specification | |
|---|---|
| Compound | Abbreviation |
| Acetyl | Ac |
| Alanine | Ala |
| 3-(2-Thiazolyl)-L-alanine | Tza |
| Arginine | Arg |
| Asparagine | Asn |
| Aspartic acid | Asp |
| t-Butyloxycarbonyl | Boc |
| Benzotriazol-l-yloxy-tris-(dimethyl-amino)phosphonium-hexafluorophosphate | Bop |
| β-Alanine | βAla |
| β-Valineβ | Val |
| β-(2-Pyridyl)-alanine | Pal(2) |
| β-(3-Pyridyl)-alanine | Pal(3) |
| β-(4-Pyridyl)-alanine | Pal(4) |
| β-(3-N-Methylpyridinium)-alanine | PalMe(3) |
| t-Butyl | tBu, But |
| t-Butyloxycarbonyl | Boc |
| Caffeic acid | Caff |
| Cysteine | Cys |
| Cyclohexylalanine | Cha |
| Cyclohexylglycine | Chg |
| 3,5-Dinitrotyrosine | Tyr(3,5-No$_2$) |
| 3,5-Diiodotyrosine | Tyr(3,5-I) |
| 3,5-Dibromotyrosine | Tyr(3,5-Br) |
| 9-Fluorenylmethyloxy-carbonyl | Fmoc |
| Glutamine | Gln |
| Glutamic acid | Glu |
| γ-Carboxyglutamic acid | Gla |
| Glycine | Gly |
| Histidine | His |
| Homoarginine | hArg |
| 3-Hydroxyproline | Hyp |
| Isoleucine | Ile |
| Leucine | Leu |
| tert-Leucine | Tle |
| Lysine | Lys |
| Mercapto-β,β-cyclopentamethylene-propionic acid | Mpp |
| Mercaptoacetic acid | Mpa |
| Mercaptopropionic acid | Mpr |
| Methionine | Met |
| 1-Naphthylalanine | Nal(1) |
| 2-Naphthylalanine | Nal(2) |
| Nicotinic acid | Nic |
| Nipecotic acid | Npa |
| N-methyl nicotinic acid | NicMe |
| Norarginine | nArg |
| Norleucine | Nle |
| Norvaline | Nva |
| Ornithine | Orn |
| Ornithine-derived dimethylamidinium | Orn(N$^\delta$-C$_3$H$_7$N) |
| Phenylalanine | Phe |

-continued

Abbreviations used in the specification

| Compound | Abbreviation |
|---|---|
| p-Guanidinophenylalanine | Phe(Gua) |
| p-Aminophenylalanine | Phe(NH$_2$) |
| p-Chlorophenylalanine | Phe(Cl) |
| p-Flurophenylalanine | Phe(F) |
| p-Nitrophenylalanine | Phe(NO$_2$) |
| p-Hydroxyphenylglycine | Pgl(OH) |
| p-Toluenesulfonyl | Tos |
| m-Amidinophenylalanine | mAph |
| p-Amidinophenylalanine | pAph |
| Phenylglycine | Pgl |
| Phenylmalonic acid | Pma |
| Proline | Pro |
| 4-Quinolinecarboxy | 4-Qca |
| Sarcosine | Sar |
| Serine | Ser |
| Threonine | Thr |
| Tryptophan | Trp |
| Tyrosine | Tyr |
| 3-iodotyrosine | Tyr(3-I) |
| O-Methyl tyrosine | Tyr(Me) |
| Valine | Val |

*Amino acids of D configuration are denoted by D-prefix using three-letter code (e.g., D-Ala, D-Cys, D-Asp, D-Trp).

"Peptides" include molecules having at least two amino acids and include polypeptides having at least about 60 amino acids. Preferably, the peptides have about 10 to about 60 amino acids, more preferably about 10–25, and most preferably about 12–25 amino acids. The definition includes linear and cyclic peptides, peptide derivatives, their salts, or optical isomers.

As used herein, an "amide bond-forming substituent contained in an amino acid side-chain", a "side-chain amino bond-forming substituent", and their grammatical variants, arc defined to include (1) any carboxy substituent contained in the side-chain ("R" group) of an amino acid wherein the carboxy substituent is capable of forming an amide linkage with an amino group contained in another molecule, i.e., the carboxy substituent reacts with an amino group contained in another molecule to form an amide linkage; and (2) any amino substituent contained in the side-chain ("R" group) of an amino acid wherein the amino substituent is capable of forming an amide linkage with a carboxy group contained in another molecule, i.e., the amino substituent reacts with a carboxy group contained in another molecule to form an amide linkage.

As used herein, "differentially-removable" protecting or protective groups are defined as any pair of protective groups capable of protecting a first amide bond-forming substituent and a second amide bond-forming substituent, wherein it is possible to deprotect the first amide bond-forming substituent protected with one member of the pair under conditions which do not deprotect the second amide bond-forming substituent protected with the other member of the pair. Differentially-removable protecting groups are also referred to herein as "orthogonal" protecting groups, and the differentially-removable protection conferred by such protective groups is referred to herein as "orthogonal" protection.

As used herein, the term "treating" refers to both therapeutic treatment and prophylactic or preventative measures. Those in need of treatment include those already with the disorder as well as those prone to having the disorder or diagnosed with the disorder or those in which the disorder is to be prevented. Consecutive treatment or administration refers to treatment on at least a daily basis without interruption in treatment by one or more days. Intermittent treatment or administration, or treatment or administration in an intermittent fashion, refers to treatment that is not consecutive, but rather cyclic in nature. The treatment regime herein can be either consecutive or intermittent. Subjects for whom the preventive measures are appropriate include those with one or more known risk factors for the disorder, such as cancer.

As used herein, the tern "pulmonary administration" refers to administration of a formulation of the invention through the lungs by inhalation. As used herein, the term "inhalation" refers to intake of air to the alveoli. In specific examples, intake can occur by self-administration of a formulation of the invention while inhaling through a nebulizer or other aerosol-delivery device, or by administration via a respirator, e.g., to a patient on a respirator. The term "inhalation" used with respect to a formulation of the invention is synonymous with "pulmonary administration."

As used herein, the term "parenteral" refers to introduction of a peptide of the invention into the body by other than the intestines, and in particular, intravenous (i.v.), intraarterial (i.a.), intraperitoneal (i.p.), intramuscular (i.m.), intraventricular, and subcutaneous (s.c.) routes.

As used herein, the term "aerosol" refers to suspension in the air. In particular, aerosol refers to the formation of particles or particulates in a formulation of the invention and its suspension in the air. According to the present invention, an aerosol formulation is a formulation comprising a peptide of the present invention that is suitable for aerosolization, i.e., formation of particles or particulates and suspension in the air, for inhalation or pulmonary administration.

As used herein, the term "dispersant" refers to an agent that assists aerosolization of the peptide or absorption of the protein in lung tissue, or both. Preferably, the dispersant is pharmaceutically acceptable. As used herein, the modifier "pharmaceutically-acceptable" means approved by a regulatory agency of the federal or a state government or listed in the U.S. Pharmacopoeia or other generally recognized pharmacopoeia for use in animals, and more particularly in humans.

A "disorder" is any condition caused, mediated, or exacerbated by, or associated with, an IGF, preferably IGF-1, that would benefit from treatment with the peptides herein. This includes chronic and acute disorders or diseases including those pathological conditions that predispose the mammal to the disorder in question. Non-limiting examples of disorders to be treated herein include diseases associated with undesirable cell proliferation, such as benign tumors, cancer, restenosis, and asthma; acromegaly; inflammatory, angiogenic, or immunological disorders; an ischemic injury such as a stroke, myocardial ischemia, or ischemic injury to the kidneys; diabetic complications such as diabetic retinopathies or neuropathies; eye-related diseases; or neuronal, glial, astrocytal, hypothalamic or other glandular, macrophagal, epithelial, stromal, or blastococlic disorders. Eye-related disorders include age-related macular degeneration; ophthalmic surgery such as cataract extraction, corneal transplantation, glaucoma filtration surgery, and keratoplasty; surgery to correct refraction, i.e., a radial keratotomy, also in sclera macular holes and degeneration; retinal tears; vitreoretinopathy; cataract disorders of the cornea such as the sequelae of radial keratotomy; dry eye; viral conjunctivitis; ulcerative conjunctivitis; optical wounds such as corneal epithelial wounds; Sjogren's syndrome; macular and retinal edema; vision-limited scarring; and retinal ischemia. Preferably, such disorders are cancer, a diabetic complication, an ischemic injury, acromegaly, restenosis, an eye-related disorder, or asthma. The efficacy of the treatment can be evidenced by a reduction in clinical manifestations or symptoms, including, for example, decreased cell proliferation or growth, improved renal clearance, improved vision, or a reduction in the amount of IGF available for binding to the IGF receptor.

The term "effective amount" refers to an amount of a peptide effective to treat a disease or disorder in a mammal. In the case of cancer, the effective amount of the peptide may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the peptide may prevent growth and/or kill existing cancer cells, it may be cytostatic and/or cytotoxic. For cancer therapy, efficacy in vivo can, for example, be measured by assessing the time to disease progression (TTP) and/or determining the response rates (RR).

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD). Preferably, the cancer comprises a tumor that expresses an IGF receptor, more preferably breast cancer, lung cancer, colorectal cancer, or prostate cancer, and most preferably breast or prostate cancer.

An "another agent that treats the disorder" is any agent other than the peptides herein that in effective amounts will treat the disorder in question. This includes a growth inhibitory agent, an angiostatic agent, or a cytotoxic agent. Preferably, the agent is a chemotherapeutic agent or antibody, preferably a growth-inhibitory antibody, an antibody that induces cell death, or an antibody that induces apoptosis.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu) chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and CYTOXAN™ cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimnustine; antibiotics such as the enediyne antibiotics (e.g., calicheamicin, especially calicheamicin $\gamma_1^I$ and calicheamicin $\theta^I_1$ (see, e.g., Agnew, Chem Intl. Ed. Engl., 33: 183–186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN™ doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine;

arabinoside ("Ara-C"); cyclophosphamide; thiotepa; taxoids, e.g., TAXOL® paclitaxel (Bristol-Myers Squibb Oncology, Princeton, N.J.) and TAXOTERE® doxetaxel (Rhône-Poulenc Rorer, Antony, France); chloranbucil; GEMZAR™ gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE™ vinorelbine; novantrone; teniposide; edatrexate; daunomycin; aminopterin; xeloda; ibandronate; CPT-11; topoisomerase inhibitor RFS 2000; difluorometlhylornithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX™ tamoxifen), raloxifene, droloxifene, 4-hydroxytamoxifen, trioxifene, keoxifene, LY117018, onapristone, and FARESTON· toremifene; aromatase inhibitors that inhibit the enzyme aromatase, which regulates estrogen production in the adrenal glands, such as, for example, 4(5)-imidazoles, aminoglutethimide, MEGASE™ megestrol acetate, AROMASIN™ exemestane, formestanie, fadrozole, RIVISOR™ vorozole, FEMARA™ letrozole, and ARIMIDEX™ anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN™ vaccine, LEUVECTIN™ vaccine, and VAXID™ vaccine; PROLEUKIN™ rIL-2; LURTOTECAN™ topoisomerase 1 inhibitor; ABARELIX™ rmRH; and pharmaceutically acceptable salts, acids or derivatives of any of the above.

A "growth inhibitory agent" when used herein refers to a compound or composition which inhibits growth of a cell in vitro and/or in vivo. Thus, the growth inhibitory agent may be one that significantly reduces the percentage of cells in S phase. Examples of growth inhibitory agents include agents that block cell cycle progression (at a place other than S phase), such as agents that induce GI arrest and M-phase arrest. Classical M-phase blockers include the vincas (vincristine and vinblastine), TAXOL® paclitaxel, and topo II inhibitors such as doxorubicin, epirubicin, daunorubicin, etoposide, and bleomycin. Those agents that arrest GI also spill over into S-phase arrest, for example, DNA alkylating agents such as tanoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antieioplastic drugs" by Murakaini et at. (W B Saunders: Philadelphia, 1995), especially p. 13.

Examples of "growth inhibitory" anti-HER2 antibodies are those which bind to HER2 and inhibit the growth of cancer cells overexpressing HER2. Preferred growth inhibitory anti-HER2 antibodies inhibit growth of SKBR3 breast tumor cells in cell culture by greater than 20%, and preferably greater than 50% (e.g., from about 50% to about 100%) at an antibody concentration of about 0.5 to 30 μg/ml, where the growth inhibition is determined six days after exposure of the SKBR3 cells to the antibody (see U.S. Pat. No. 5,677,171 issued Oct. 14, 1997).

An antibody which "induces cell death" is one which causes a viable cell to become nonviable. The cell is generally one which expresses the antigen to which the antibody binds, especially where the cell overexpresses the antigen. Preferably, the cell is a cancer cell, e.g., a breast, ovarian, stomach, endometrial, salivary gland, lung, kidney, colon, thyroid, pancreatic or bladder cell. In vitro, the cell may be a SKBR3, BT474, Calu 3, MDA-MB-453, MDA-MB-361 or SKOV3 cell. Cell death in vitro may be determined in the absence of complement and immune effector cells to distinguish cell death induced by antibody dependent cell-mediated cytotoxicity (ADCC) or complement dependent cytotoxicity (CDC). Thus, the assay for cell death may be performed using heat inactivated serum (i.e. in the absence of complement) and in the absence of immune effector cells. To determine whether the antibody is able to induce cell death, loss of membrane integrity as evaluated by uptake of propidium iodide (PI), trypan blue (see Moore et al. *Cytotechnology*, 17:1–11 (1995)) or 7AAD can be assessed relative to untreated cells.

An antibody that "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is one which expresses the antigen to which the antibody binds and may be one which overexpresses the antigen. The cell may be a tumor cell, e.g., a breast, ovarian, stomach, endometrial, salivary gland, lung, kidney, colon, thyroid, pancreatic or bladder cell. In vitro, the cell may be a SKBR3, BT474, Calu 3 cell, MDA-MB-453, MDA-MB-361 or SKOV3 cell. Various methods are available for evaluating the cellular events associated with apoptosis. For example, phosphatidyl serine (PS) translocation can be measured by annexin binding; DNA fragmentation can be evaluated through DNA laddering as disclosed in the example herein; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cell in an annexin binding assay using cells expressing the antigen to which the antibody binds.

Examples of antibodies that induce apoptosis include the anti-HER2 monoclonal antibodies 7F3 (ATCC HB-12216), and 7C2 (ATCC HB 12215), including humanized and/or affinity matured variants thereof; the anti-DR5 antibodies 3F1 1.39.7 (ATCC HB-12456); 3H3.14.5 (ATCC HB-12534); 3D5. 1.10 (ATCC HB-12536); and 3H3. 14.5 (ATCC HB-12534), including humanized and/or affinity matured variants thereof; the human anti-DR5 receptor antibodies 16E2 and 20E6, including affinity matured variants thereof (WO98/5 1793, expressly incorporated herein by reference); the anti-DR4 antibodies 4E7.24.3 (ATCC HB-12454); 4H6.17.8 (ATCC HB-12455); 1H5.25.9 (ATCC HB-12695); 4G7.18.8 (ATCC PTA-99); and 5G I 1.17.1 (ATCC HB-12694), including humanized and/or affinity matured variants thereof.

In order to screen for antibodies which bind to an epitope on an antigen bound by an antibody of interest, a routine cross-blocking assay such as that described in *Antibodies, A Laboratory Manual*, eds. Harlow and Lane (New York: Cold Spring Harbor Laboratory, 1988) can be performed.

The word "label" when used herein refers to a detectable compound or composition which is conjugated directly or indirectly to the polypeptide. The label may be itself be detectable (e.g., radioisotope labels or fluorescent labels) or, in the case of an enzymatic label, may catalyze chemical alteration of a substrate compound or composition which is detectable.

B. Modes for Carrying out the Invention

The present invention relates to various peptides having the function of antagonizing IGF-1. Specifically, one family of such peptides (family 1) comprises the sequence:

$(Xaa)_1(Xaa)_2CYs(Xaa)_3(Xaa)_4SerVal(Xaa)_5AlaLeu(Xaa)_6(Xaa)_7CYsMet(Xaa)_8$ (SEQ ID NO:1) $(Xaa)_1$, $(Xaa)_2$, and $(Xaa)_7$ are any amino acid, $(Xaa)_3$ is Phe, Leu, or Tyr, $(Xaa)_4$ is Glu, Asp, Ala, Gly, Thr, or Ser, $(Xaa)_5$ is Glu, Asp, Ala, or Gly, $(Xaa)_6$ is Arg or Lys, and $(Xaa)_8$ is Tyr or Arg. $(Xaa)_4$ is Glu, Ala, Gly, Thr, or Ser, $(Xaa)_5$ is Glu, Ala, or Gly, and $(Xaa)_8$ is Tyr. The preferred peptides of the above sequence are such that $(Xaa)_4$ is Glu, Ala or Thr, $(Xaa)_5$ is Ala or Gly, and $Xaa_8$ is Tyr. More preferred are the peptides wherein $(Xaa)_4$ is Glu or Ala, $(Xaa)_5$ is Ala or Gly, and $(Xaa)_8$ is Tyr. Still more preferred are the peptides comprising the sequence RNCFESVAALRRCMYG (SEQ ID NO:2), MDCLASVEALKWCMYG (SEQ ID NO:3), or FECLTSVEALRGCMYG (SEQ ID NO:4). Most preferred are peptides that comprise SEQ ID NO:2 or 3.

The second family of such peptides (family 2) comprises the sequence:

$(Xaa)_1(Xaa)_2Cys(Xaa)_3(Xaa)_4Asp(Xaa)_5(Xaa)_6Gly(Xaa)_7(Xaa)_8TyrCysTrp(Xaa)_9$ (SEQ ID NO:5), where $(Xaa)_1$, $(Xaa)_4$, and $(Xaa)_8$ are any amino acid, $(Xaa)_2$ is Arg, Lys, Gly, Ser, or Thr, $(Xaa)_3$ is Ala or Val, $(Xaa)_5$ is Ala or Leu, $(Xaa)_6$ is Ala, Gly, or Leu, $(Xaa)_7$ is Phe, Tyr, Trp, or Gly, and $(Xaa)_9$ is Glu, Asp, Ala, or Gly. The preferred peptides herein are such that $(Xaa)_2$ is Gly, Ser, Arg, or Thr, and $(Xaa)_9$ is Glu, Ala, or Asp. More preferred are peptides wherein $(Xaa)_2$ is Glu or Arg, $(Xaa)_5$ is Leu, $(Xaa)_6$ is Ala or Gly, $(Xaa)_7$ is Phe, and $(Xaa)_9$ is Ala. The most preferred of this family of peptides are those that comprise the sequence LGCASDLAGFWYCWAG (SEQ ID NO:6) or WRCVDDLGGFQYCWAG (SEQ ID NO:7).

Preferably, all the amino acids in these two families of peptides are L-amino acids. Also preferred is that these families of peptides comprise a glycine residue after $(Xaa)_8$ for family 1 above or after $(Xaa)_9$ for family 2 above.

Production of Peptides

The peptides of this invention can be made by chemical synthesis or by employing recombinant technology. These methods are known in the art. Chemical synthesis, especially solid-phase synthesis, is preferred for short (e.g., less than 50 residues) peptides or those containing unnatural or unusual amino acids such as D-Tyr, ornithinie, amino-adipic acid, and the like. Recombinant procedures are preferred for longer polypeptides. When recombinant procedures are selected, a synthetic gene may be constructed de novo or a natural gene may be mutated by, for example, cassette mutagenesis.

A useful method for identification of certain residues or regions of the peptides herein suitable for amino acid substitution other than those described herein is called alanine-scanning mutagenesis as described by Cunningham and Wells, *Science,* 244: 1081–1085 (1989). Here a residue or group of target residues are identified (e.g., charged residues such as Arg, Asp, His, Lys, and Glu) and replaced by a neutral or negatively-charged amino acid to affect the interaction of the amino acids with the surrounding aqueous environment in or outside the cell. Those domains demonstrating functional sensitivity to the substitution then are refined by introducing further or other variations at or for the sites of substitution. Thus, while the site for introducing an amino acid sequence variation is predetermined, the nature of the mutation per se need not be predetermined. For example, to optimize the performance of a mutation at a given site, Ala-scanning or random mutagenesis may be conducted at the target codon or region and the expressed compound screened for the optimal combination of desired activity.

Phage display of protein or peptide libraries offers another methodology for the selection of compounds with improved affinity, altered specificity, or improved stability (Smith, *Curr. Opin. Biotechnol.,* 2:668–673 (1991)). High affinity proteins, displayed in a monovalent fashion as fusions with the M13 gene III coat protein (Clackson et al., *Trends Biotechnol.* 12:173–183 (1994)), can be identified by cloning and sequencing the corresponding DNA packaged in the phagemid particles after a number of rounds of binding selection.

Other peptides include the fusion to the N- or C-terminus of the peptides described herein of immunogenic polypeptides, e.g., bacterial polypeptides such as beta-lactamase or an enzyme encoded by *E. coli* Trp locus or yeast protein, and C-terminal fusion with proteins having a long half-life such as immunoglobulin constant region or other immunoglobulin regions, albumin, or ferritin as described in WO 89/02922 published 6 Apr. 1989. Further, free functional groups on the side-chains of the amino acid residues can also be modified by amidation, acylation, or other substitution, which can, for example, change the solubility of the peptides without affecting their activity.

Set forth below are exemplary general recombinant procedures.

From a purified IGF and its amino acid sequence, for example, an IGF antagonist that is a peptidyl mutant of an IGF may be produced using recombinant DNA techniques. These techniques contemplate, in simplified form, taking the gene, either natural or synthetic, encoding the peptide; inserting it into an appropriate vector; inserting the vector into an appropriate host cell; culturing the host cell to cause expression of the gene; and recovering or isolating the peptide produced thereby. Preferably, the recovered peptide is then purified to a suitable degree.

Somewhat more particularly, the DNA sequence encoding a peptidyl IGF antagonist is cloned and manipulated so that it may be expressed in a convenient host. DNA encoding parent polypeptides can be obtained from a genomic library, from cDNA derived from mRNA from cells expressing the peptide, or by synthetically constructing the DNA sequence (Sambrook et al., *Molecular Cloning: A Laboratory Manual* (2d ed.) (Cold Spring Harbor Laboratory: N.Y., 1989)).

The parent DNA is then inserted into an appropriate plasmid or vector that is used to transform a host cell. In general, plasmid vectors containing replication and control sequences derived from species compatible with the host cell are used in connection with those hosts. The vector ordinarily carries a replication site, as well as sequences encoding proteins or peptides that are capable of providing phenotypic selection in transformed cells.

For example, *E. coli* may be transformed using pBR322, a plasmid derived from an *E. coli* species (Mandel et al., *J. Mol. Biol.* 53: 154 (1970)). Plasmid pBR322 contains genes for ampicillin and tetracycline resistance, and thus provides easy means for selection. Other vectors include different features such as different promoters, which are often important in expression. For example, plasmids pKK223-3, pDR720, and pPL-lambda represent expression vectors with the tac, trp, or PL promoters that are currently available (Pharmacia Biotechnology).

One preferred vector is pB0475. This vector contains origins of replication for phage and *E. coli* that allow it to be shuttled between such hosts, thereby facilitating both mutagenesis and expression (Cunningham et al., *Science*, 243: 1330–1336 (1989); U.S. Pat. No. 5,580,723). Other preferred vectors are pR1T5 and pR1T2T (Pharmiacia Biotechnology). These vectors contain appropriate promoters followed by the Z domain of protein A, allowing genes inserted into the vectors to be expressed as fusion proteins.

Other preferred vectors can be constructed using standard techniques by combining the relevant traits of the vectors described above. Relevant traits include the promoter, the ribosome binding site, the decorsin or ornatin gene or gene fusion (the Z domain of protein A and decorsin or ornatin and its linker), the antibiotic resistance markers, and the appropriate origins of replication.

The host cell may be prokaryotic or eukaryotic. Prokaryotes arc preferred for cloning and expressing DNA sequences to produce parent IGF-1 polypeptide, segment-substituted peptides, residue-substituted peptides, and peptide vartiants. For example, *E. coli* K12 strain 294 (ATCC No. 31446) may be used as well as *E. coli* B, *E. coli* X1776 (ATCC No. 31537), and *E. coli* c600 and c600hfl, *E. coli* W3110 (F-, gamma-, prototrophic/ATCC No. 27325), bacilli such as *Bacillus subtilis*, and other enterobacteriaceae such as *Salmonella marcesans* or *Serratia marcesans*, and various *Pseudomonas* species. The preferred prokaryote is *E. coli* W3110 (ATCC 27325). When expressed by prokaryotes the peptides typically contain an N-terminal methionine or a formyl methionine and are not glycosylated. In the case of fusion proteins, the N-terminal methionine or formyl methionine resides on the amino terminus of the fusion protein or the signal sequence of the fusion protein. These examples are, of course, intended to be illustrative rather than limiting.

In addition to prokaryotes, eukaryotic organisms, such as yeast cultures, or cells derived from multicellular organisms may be used. In principle, any such cell culture is workable. However, interest has been greatest in vertebrate cells, and propagation of vertebrate cells in culture (tissue culture) has become a reproducible procedure. *Tissue Culture*, Academic Press, Kruse and Patterson, editors (1973). Examples of such useful host cell lines are VERO and HeLa cells, Chinese Hamster Ovary (CHO) cell lines, W 138, 293, BHK, COS-7 and MDCK cell lines.

A variation on the above procedures contemplates the use of gene fusions, wherein the gene encoding the desired peptide is associated, in the vector, with a gene encoding another protein or a fragment of another protein. This results in the desired peptide being produced by the host cell as a fusion with another protein or peptide. The "other" protein or peptide is often a protein or peptide that can be secreted by the cell, making it possible to isolate and purify the desired peptide from the culture medium and eliminating the necessity of destroying the host cells that arises when the desired peptide remains inside the cell. Alternatively, the fusion protein can be expressed intracellularly. It is useful to use fusion proteins that are highly expressed.

The use of gene fusions, though not essential, can facilitate the expression of heterologous peptides in *E. coli* as well as the subsequent purification of those gene products. Harris, in *Genetic Engineering*, Williamson, R., Ed. (Academic Press, London, Vol. 4, 1983), p. 127; Ljungquist et al., *Eur. J. Biochem.*, 186: 557–561 (1989) and Ljungquist et al., *Eur. J. Biochem.*, 186: 563–569 (1989). Protein A fusions are often used because the binding of protein A, or more specifically the Z domain of protein A, to IgG provides an "affinity handle" for the purification of the fused protein. See Nilsson et al., *Protein Engineering*, 1: 107–113 (1987). It has also been shown that many heterologous proteins are degraded when expressed directly in *E. coli*, but are stable when expressed as fusion proteins. Marston, *Biochem J.*, 240: 1 (1986).

After expression and secretion, for example, from *E. coli*, the fusion protein is cleaved to yield free peptide, which can be purified from the reaction mix. The cleavage may be accomplished using chemicals, such as cyanogen bromide, which cleaves at a methionine, or hydroxylamine, which cleaves between an Asn and Gly residue. Using standard recombinant DNA methodology, the nucleotide base pairs encoding these amino acids may be inserted just prior to the 5' end of the gene encoding the desired peptide.

Alternatively, one can employ proteolytic cleavage of fusion protein (Carter, in *Protein Purification: From Molecular Mechanisms to Large-Scale Processes*, Ladisch et al., eds. (American Chemical Society Symposium Series No. 427, 1990), Ch 13, pages 181–193; Varadarajan et al., *Proc. Natl. Acad. Sci. USA*, 82: 5681–5684 (1985); Castellanos-Serra et al., *FEBS Letters*, 378: 171–176 (1996); Nilsson et al., *J. Biotechnol.*, 48: 241–250 (1996)).

Proteases such as Factor Xa, thrombin, subtilisin, or trypsin, or its mutants, and a number of others have been successfully used to cleave fusion proteins. Trypsin is preferred because peptide-Z-domain fusions are found to be readily cleaved by this protease. Detailed procedures for employing trypsin as protease are found in Smith, *Methods in Mol. Biol.*, 32: 289–196 (1994). Typically, a peptide linker that is amenable to cleavage by the protease used is inserted between the "other" protein (e.g., the Z domain of protein A) and the desired peptide. Using recombinant DNA methodology, the nucleotide base pairs encoding the linker are inserted between the genes or gene fragments coding for the other proteins. Proteolytic cleavage of the partially-purified fusion protein containing the correct linker can then be carried out on either the native fusion protein, or the reduced or denatured fusion protein.

The peptide may or may not be properly folded when expressed as a fusion protein. Also, the specific peptide linker containing the cleavage site may or may not be accessible to the protease. These factors determine whether the fusion protein must be denatured and refolded, and if so, whether these procedures are employed before or after cleavage.

When denaturing and refolding are needed, typically the peptide is treated with a chaotrope, such as guanidine HCl, and is then treated with a redox buffer, containing, for example, reduced and oxidized dithiothreitol or glutathione at the appropriate ratios, pH, and temperature, such that the peptide is refolded to its native structure.

As well as by recombinant methods, peptides of the invention can be conveniently prepared using solid phase peptide synthesis (Merrifield, *J. Am. Chem. Soc.*, 85: 2149 (1964); Houghten, *Proc. Natl. Acad. Sci. USA*, 82: 5132 (1985)), although other equivalent chemical syntheses known in the art are employable. Solid-phase synthesis is initiated from the C-terminus of the peptide by coupling a protected α-amino acid to a suitable resin. Such a starting material can be prepared by attaching an α-amino-protected amino acid by an ester linkage to a chloroinethylated resin or a hydroxyinethyl resin, or by an amide bond to a BHA resin or MBHA resin. The preparation of the hydioxymiiethyl resin is described by Bodansky et al., *Chem. Ind.* (*London*), 38: 1597–1598 (1966). Chloromethylated resins are commercially available from BioRad Laboratories, Richmond, Calif. and from Lab. Systems, Inc. The preparation of such a resin is described by Stewart et al., *Solid Phase Peptide Synthesis* (Freeman & Co., San Francisco 1969), Chapter 1, pp. 1–6. BHA and MBHA resin supports are commercially available and are generally used only when the desired polypeptide being synthesized has an unsubstituted amide at the C-terminus.

The amino acids are coupled to the peptide chain using techniques well known in the art for the formation of peptide bonds. One method involves converting the amino acid to a derivative that will render the carboxyl group more susceptible to reaction with the free N-terminal amino group of the peptide fragment. For example, the amino acid can be converted to a mixed anhydride by reaction of a protected amino acid with ethylchloroformate, phenyl chloroformate, sec-butyl chloroformate, isobutyl chloroformate, pivaloyl chloride or like acid chlorides. Alternatively, the amino acid can be converted to an active ester such as a 2,4,5-trichlorophenyl ester, a pentachlorophenyl ester, a pentafluorophenyl ester, a p-nitrophenyl ester, a N-hydroxysuccinimide ester, or an ester formed from 1-hydroxybenzotriazole.

Another coupling method involves use of a suitable coupling agent such as N,N'-dicyclohexylcarbodiimide or N,N'-diisopropyl-carbodiimide. Other appropriate coupling agents, apparent to those skilled in the art, are disclosed in E. Gross & J. Meienhofer, *The Peptides: Analysis, Structure, Biology*, Vol. 1: Major Methods of Peptide Bond Formation (Academic Press: New York, 1979).

It should be recognized that the α-amino group of each amino acid employed in the peptide synthesis must be protected during the coupling reaction to prevent side reactions involving their active α-amino function. It should also be recognized that certain amino acids contain reactive side-chain functional groups (e.g., sulfhydryl, amino, carboxyl, and hydroxyl) and that such functional groups must also be protected with suitable protecting groups to prevent a chemical reaction from occurring at that site during both the initial and subsequent coupling steps. Suitable protecting groups, known in the art, are described in Gross and Meienhofer, *The Peptides: Analysis, Structure, Biology*, Vol.3: "Protection of Functional Groups in Peptide Synthesis" (Academic Press: New York, 1981).

In the selection of a particular side-chain protecting group to be used in synthesizing the peptides, the following general rules are followed. An α-amino protecting group (a) must render the α-amino function inert under the conditions employed in the coupling reaction, (b) must be readily removable after the coupling reaction under conditions that will not remove side-chain protecting groups and will not alter the structure of the peptide fragment, and (c) must eliminate the possibility of racemization upon activation immediately prior to coupling. A side-chain protecting group (a) must render the side-chain functional group inert under the conditions employed in the coupling reaction, (b) must be stable under the conditions employed in removing the α-amino protecting group, and (c) must be readily removable upon completion of the desired amino acid peptide under reaction conditions that will not alter the structure of the peptide chain.

It will be apparent to those skilled in the art that the protecting groups known to be useful for peptide synthesis will vary in reactivity with the agents employed for their removal. For example, certain protecting groups such as triphenylmethyl and 2-(p-biphenylyl)isopropyloxycarbonyl are very labile and can be cleaved under mild acid conditions. Other protecting groups, such as t-butyloxycarbonyl (BOC), t-amyloxycarbonyl. adamantyl-oxycarbonyl, and p-methoxybenzyloxycarbonyl, are less labile and require moderately strong acids, such as trifluoroacetic, hydrochloric, or boron trifluoride in acetic acid, for their removal. Still other protecting groups, such as benzyloxycarbonyl (CBZ or Z), halobenzyloxycarbonyl, p-nitrobenzyloxycarbonyl cycloalkyloxycarbonyl, and isopropyloxycarbonyl, are even less labile and require stronger acids, such as hydrogen fluoride, hydrogen bromide, or boron trifluoroacetate in trifluoroacetic acid, for their removal. Among the classes of useful amino acid protecting groups are included:

(1) for an α-amino group, (a) aromatic urethane-type protecting groups, such as fluorenylmethyloxycarbonyl (FMOC) CBZ, and substituted CBZ, such as, e.g., p-chlorobenzyloxycarbonyl, p-6-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, and the like; (b) aliphatic urethane-type protecting groups, such as BOC, t-amyloxycarbonyl, isopropyloxycarbonyl, the like; (c) cycloalkyl urethane-type protecting groups, such as cyclopentyloxycarbonyl, adamantyloxycarbonyl, and cyclohexyloxycarbonyl; and d) allyloxycarbonyl. The preferred α-amino protecting groups are BOC or FMOC.

(2) for the side chain amino group present in Lys, protection may be by any of the groups mentioned above in (1) such as BOC, p-chlorobenzyloxycarbonyl, etc.

(3) for the guanidino group of Arg, protection may be by nitro, tosyl, CBZ, adamantyloxycarbonyl, 2,2,5,7,8-pentamethylchroman-6-sulfonyl, 2,3,6-trimethyl-4-methoxyphenylsulfonyl, or BOC.

(4) for the hydroxyl group of Ser, Thr, or Tyr, protection may be, for example, by C1–C4 alkyl, such as t-butyl; benzyl (BZL); or substituted BZL, such as p-methoxybenzyl, p-nitrobenzyl, p-chlorobenzyl, o-chlorobenzyl, and 2,6-dichlorobenzyl.

(5) for the carboxyl group of Asp or Glu, protection may be, for example, by esterification using groups such as BZL, t-butyl, cyclohexyl, cyclopentyl, and the like.

(6) for the imidazole nitrogen of His, the tosyl moiety is suitably employed.

(7) for the phenolic hydroxyl group of Tyr, a protecting group such as tetrahydropyranyl, tert-butyl, trityl, BZL, chlorobenzyl, 4-bromobenzyl, or 2,6-dichlorobenzyl is suitably employed. The preferred protecting group is 2,6-dichlorobenzyl.

(8) for the side-chain amino group of Asn or Gln, xanthyl (Xan) is preferably employed.

(9) for Met, the amino acid is preferably left unprotected.

(10) for the thio group of Cys, p-methoxybenzyl is typically employed.

The C-terminal amino acid, e.g., Lys, is protected at the N-amino position by an appropriately-selected protecting group, in the case of Lys, BOC. The BOC-Lys-OH can be first coupled to the benzyhydrylamine or chloromethylated resin according to the procedure set forth in Horiki et al., *Chemistry Letters,* 165–1 68 (1978) or using isopropylcarbodiimide at about 25° C. for 2 hours with stirring. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups are described in the literature.

After removal of the α-amino protecting group, the remaining α-amino and side-chain protected amino acids are coupled stepwise within the desired order. As an alternative to adding each amino acid separately in the synthesis, some may be coupled to one another prior to addition to the solid-phase synthesizer. The selection of an appropriate coupling reagent is within the skill of the art. Particularly suitable as a coupling reagent is N,N-dicyclohexyl carbodiimide or diisopropylcarbodiimide.

Each protected amino acid or amino acid sequence is introduced into the solid-phase reactor in excess, and the coupling is suitably carried out in a Medium of dimethylformamide (DMF) or $CH_2Cl_2$ or mixtures thereof. If incomplete coupling occurs, the coupling procedure is repeated before removal of the N-amino protecting group prior to the coupling of the next amino acid. The success of the coupling reaction at each stage of the synthesis may be monitored. A preferred method of monitoring the synthesis is by the ninhydrin reaction, as described by Kaiser et al., *Anal. Biochem*, 34: 595 (1970). The coupling reactions can be performed automatically using well-known methods, for example, a BIOSEARCH9500™ peptide synthesizer.

Upon completion of the desired peptide sequence, the protected peptide must be cleaved from the resin support, and all protecting groups must be removed. The cleavage reaction and removal of the protecting groups is suitably accomplished simultaneously or stepwise. When the resin support is a chloro-methylated polystyrene resin, the bond anchoring the peptide to the resin is an ester linkage formed between the free carboxyl group of the C-terminal residue and one of the many chloromethyl groups present on the resin matrix. It will be appreciated that the anchoring bond can be cleaved by reagents that are known to be capable of breaking an ester linkage and of penetrating the resin matrix.

One especially convenient method is by treatment with liquid anhydrous hydrogen fluoride. This reagent not only will cleave the peptide from the resin but also will remove all protecting groups. Hence, use of this reagent will directly afford the fully deprotected peptide. When the chloromethylated resin is used, hydrogen fluoride treatment results in the formation of the free peptide acids. When the benzhydrylamine resin is used, hydrogen fluoride treatment results directly in the free peptide amines. Reaction with hydrogen fluoride in the presence of anisole and dimethylsulfide at 0° C. for one hour will simultaneously remove the side-chain protecting groups and release the peptide from the resin.

When it is desired to cleave the peptide without removing protecting groups, the protected peptide-resin can undergo methanolysis to yield the protected peptide in which the C-terminal carboxyl group is methylated. The methyl ester is then hydrolyzed under mild alkaline conditions to give the free C-terminal carboxyl group. The protecting groups on the peptide chain then are removed by treatment with a strong acid, such as liquid hydrogen fluoride. A particularly useful technique for methanolysis is that of Moore et al., *Peptides, Proc. Fifth Amer. Pept. Symp.*, M. Goodman and J. Meienhofer, Eds., (John Wiley, N.Y., 1977), p. 518–521, in which the protected peptide-resin is treated with methanol and potassium cyanide in the presence of crown ether.

Another method for cleaving the protected peptide from the resin when the chloromethylated resin is employed is by ammonolysis or by treatment with hydrazine. If desired, the resulting C-terminal amide or hydrazide can be hydrolyzed to the free C-terminal carboxyl moiety, and the protecting groups can be removed conventionally.

It will also be recognized that the protecting group present on the N-terminal α-amino group may be removed preferentially either before or after the protected peptide is cleaved from the support.

Purification of the polypeptides of the invention is typically achieved using conventional procedures such as preparative high-pressure liquid chromatography (HPLC) (including reversed-phase HPLC) or other known chromatographic techniques such as gel permeation, ion exchange, partition chromatography, affinity chromatography (including monoclonal antibody columns), or counter-current distribution.

The peptides of this invention may be stabilized by polymerization. This may be accomplished by crosslinking monomer chains with polyfunctional crosslinking agents, either directly or indirectly, through multi-functional polymers. Ordinarily, two substantially identical polypeptides are crosslinked at their C- or N-termini using a bifunctional crosslinking agent. The agent is used to crosslink the terminal amino and/or carboxyl groups. Generally, both terminal carboxyl groups or both terminal amino groups are crosslinked to one another, although by selection of the appropriate crosslinking agent the α-amino group of one polypeptide is crosslinked to the terminal carboxyl group of the other polypeptide. Preferably, the polypeptides are substituted at their C-termini with cysteine. Under conditions well known in the art a disulfide bond can be formed between the terminal cysteines, thereby crosslinking the polypeptide chains. For example, disulfide bridges are conveniently formed by metal-catalyzed oxidation of the free cysteines or by nucleophilic substitution of a suitably modified cysteine residue. Selection of the crosslinking agent will depend upon the identities of the reactive side-chains of the amino acids present in the polypeptides. For example, disulfide crosslinking would not be preferred if cysteine was present in the polypeptide at additional sites other than the C-terminus. Also within the scope hereof are peptides crosslinked with methylene bridges.

Suitable crosslinking sites on the peptides, aside from the N-terminal amino and C-terminal carboxyl groups, include epsilon amino groups found on lysine residues, as well as amino, imino, carboxyl, sulfhydryl and hydroxyl groups located on the side-chains of internal residues of the peptides or residues introduced into flanking sequences. Crosslinking through externally added crosslinking agents is suitably achieved, e.g., using any of a number of reagents familiar to those skilled in the art, for example, via carbodiimide treatment of the polypeptide. Other examples of suitable multi-functional (ordinarily bifunctional) crosslinking agents are found in the literature.

The peptides of this invention also may be conformationally stabilized by cyclization. The peptides ordinarily are cyclized by covalently bonding the N- and C-terminal domains of one peptide to the corresponding domain of another peptide of this invention so as to form cyclo-oligomers containing two or more iterated peptide sequences, each internal peptide having substantially the same sequence. Further, cyclized peptides (whether cyclo-oligomers or cyclo-monomers) are crosslinked to form 1–3 cyclic structures having from 2 to 6 peptides comprised therein. The peptides preferably are not covalently bonded through α-amino and main-chain carboxyl groups (head to tail), but rather are crosslinked through the side-chains of residues located in the N- and C-terminal domains. The linking sites thus generally will be between the side-chains of the residues.

Many suitable methods per se are known for preparing mono-or poly-cyclized peptides as contemplated herein. Lys/Asp cyclization has been accomplished using Na-Boc-amino acids on solid-phase support with Fmoc/9-fluorenylmethyl (OFm) side-chain protection for Lys/Asp; the process is completed by piperidine treatment followed by cyclization. Glu and Lys side-chains also have been crosslinked in preparing cyclic or bicyclic peptides: the peptide is synthesized by solid-phase chemistry on a p-methylbenzhydrylamine resin. The peptide is cleaved from the resin and deprotected. The cyclic peptide is formed using diphenylphosphorylazide in diluted methylformamide. For an alternative procedure, see Schiller et al., *Peptide Protein Res.*, 25: 171–177 (1985). See also U.S. Pat. No. 4,547,489.

Disulfide crosslinked or cyclized peptides are generated by conventional methods. The method of Pelton et al. (*J. Med. Chem.*, 29: 2370–2375 (1986)) is suitable, except that a greater proportion of cyclo-oligomers are produced by conducting the reaction in more concentrated solutions than the dilute reaction mixture described by Pelton et al., supra, for the production of cyclo-monomers. The same chemistry is useful for synthesis of dimers or cyclo-oligomers or cyclo-monomers. Also useful are thiomethylene bridges. Lebl and Hruby, *Tetrahedron Letters*, 25: 2067–2068 (1984). See also Cody et al., *J. Med. Chem.*, 28: 583 (1985).

The desired cyclic or polymeric peptides are purified by gel filtration followed by reversed-phase HPLC or other conventional procedures. The peptides are sterile filtered and formulated into conventional pharmacologically acceptable vehicles.

The starting materials required for the processes described herein are known in the literature or can be prepared using known methods and known starting materials.

If in the peptides being created carbon atoms bonded to four non-identical substituents are asymmetric, then the compounds may exist as diastereoisomers, enanitiomers, or mixtures thereof. The syntheses described above may employ racemates, enantiomers, or diastereomers as starting materials or intermediates. Diastereomeric products resulting from such syntheses may be separated by chromatographic or crystallization methods. Likewise, enantiomeric product mixtures may be separated using the same techniques or by other methods known in the art. Each of the asymmetric carbon atoms, when present, may be in one of two configurations (R or S), and both are within the scope of the present invention.

The peptides described in this invention may be isolated as the free acid or base or converted to salts of various inorganic and organic acids and bases. Such salts are within the scope of this invention. Examples of such salts include ammonium, met al salts like sodium, potassium, calcium, and magnesium; salts with organic bases like dicyclohexylamine, N-methyl-D-glucamine and the like; and salts with amino acids like arginine or lysine. Salts with inorganic and organic acids may be likewise prepared, for example, using hydrochloric, hydrobromic, sulfuric, phosphoric, trifluoroacetic, methanesulfonic, malic, maleic, fumaric acid, and the like. Non-toxic and physiologically-compatible salts are particularly useful, although other less desirable salts may have use in the processes of isolation and purification.

A number of methods are useful for the preparation of the salts described above and are known to those skilled in the art. Examples include reaction of the free acid or free base form of the peptide with one or more molar equivalents of the desired acid or base in a solvent or solvent mixture in which the salt is insoluble; or in a solvent like water after which the solvent is removed by evaporation, distillation or freeze drying. Alternatively, the free acid or base form of the product may be passed over an ion-exchange resin to form the desired salt or one salt form of the product may be converted to another using the same general process.

Use of Peptides

The peptides herein may be useful in diagnostic assays, e.g., for detecting expression of IGF-1 in specific cells, tissues, or serum.

For diagnostic applications, the peptide typically will be labeled with a detectable moiety. Numerous labels are available which can be generally grouped into the following categories:

(a) Radioisotopes, such as $^{35}$S, $^{14}$C, $^{125}$I, $^{3}$H, and $^{131}$I. The peptide can be labeled with the radioisotope using the techniques described in *Current Protocols in Immunology*, Volumes 1 and 2, Coligen et al., ed. (Wiley-Interscience: New York, 1991), for example, and radioactivity can be measured using scintillation counting.

(b) Fluorescent labels such as rare earth chelates (europium chelates) or fluorescein and its derivatives, rhodaine and its derivatives, dansyl, Lissamine, phycoerythrin and Texas Red are available. The fluorescent labels can be conjugated to the peptide using the techniques disclosed in *Current Protocols in Immunology*, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.* (ed J. Langone & H. Van Vunakis), , 73:147–166 (Academic Press, New York, 1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g.,orthophenylene diamine (OPD) or 3,3',5,5'-tetramethyl benzidine hydrochloride (TMB));

(ii) alkaline phosphatase (AP) with para-nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbellifuryl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the peptide. The skilled artisan will be aware of various techniques for achieving this. For example, the peptide call be conjugated with biotin and any of the three broad categories of labels mentioned above can be conjugated with avidin, or vice versa. Biotin binds selectively to avidin and thus, the label can be conjugated with the peptide in this indirect manner. Alternatively, to achieve indirect conjugation of the label with the peptide, the peptide is conjugated with a small hapten (e.g., digoxin) and one of the different types of labels mentioned above is conjugated with an anti-hapten peptide (e.g., anti-digoxin antibody). Thus, indirect conjugation of the label with the peptide can be achieved.

In another embodiment of the invention, the peptide need not be labeled, and the presence thereof can be detected using a labeled antibody that binds to the peptide.

The peptide of the present invention may be employed in any known assay method, such as competitive binding assays, direct and indirect sandwich assays, and immunoprecipitation assays. Zola, *Monoclonal Antibodies: A Manual of Techniques*, pp.147–158 (CRC Press, Inc. 1987).

The peptide may also be used for ini vivo diagnostic assays. Generally, the peptide is labeled with a radionuclide (such as $^{111}$In, $^{99}$Tc, $^{14}$C, $^{131}$I, $^{125}$I, $^{3}$H, $^{32}$P or $^{35}$S) so that the antigen or cells expressing it can be localized using immunoscintiography.

The peptides of this invention are shown to bind to IGF-1 and inhibit IGFBP-3 and IGFBP-1 binding to IGF-1. It is contemplated that the peptide of the present invention may be used to treat a mammal, e.g. a patient suffering from, or predisposed to, a disease or disorder who could benefit from administration of the peptide. It is known to those skilled in the art that there are many disorders caused by IGFs. These disorders are set forth above.

If the disorder is cancer comprising a tumor with an IGF receptor, the efficacy of the treatment can be evidenced by a reduction in clinical manifestations or symptoms, including, for example, the size of a tumor or reductions in the amount of IGF available for binding to an IGF receptor of the tumor. Examples of these protocols are well known in the art. For example, the peptide can be administered to subjects having an IGF-dependent tumor, and tumor size could be monitored using imaging techniques, such as MRI, mammography, or ultrasound depending on the type of tumor. Imaging could be performed, for example, twice monthly. Serum levels of IGF and IGFBP could also be measured from serum samples from the subject at regular intervals. For example, levels of plasma IGF-1 and IGF-2 in treated subjects can be monitored with radioimmunoassay, using an antibody specific for IGF and preferably for the IGFBP binding domain on IGF. Plasma IGF levels could be measured with and without acid dissociation of IGFs and IGFBPs in order to assess the levels of bound and unbound IGF. Thus, by comparing the IGF levels with and without acid dissociation, the amount of unbound IGF can be determined. Normal serum levels of IGF-1 and IGF-2 after acid dissociation typically range from about 90 to 320 and 288–740 µg/L, respectively. Plasma levels of the IGF antagonist peptide herein can be assessed similarly using a high affinity monoclonal antibody specific for the IGF antagonist peptide.

The peptides of this invention may be administered to the mammal by any suitable technique, including oral, intraventricular, transdermal, extracorporeal, parenteral (e.g., intradermal, intramuscular, intraperitoneal, intravenous, intratracheal, or subcutaneous injection or infusion, or implant), nasal, pulmonary, vaginal, rectal, sublingual, or topical routes of administration, and can be formulated in dosage forms appropriate for each route of administration. The specific route of administration will depend, e.g., on the medical history of the patient, including any perceived or anticipated side effects using the peptide, the type of peptide being administered, and the particular disorder to be corrected. Most preferably, the administration is orally or by pulmonary administration or continuous infusion (using, e.g., slow-release devices or minipumps such as osmotic pumps or skin patches), or by injection (using, e.g., intravenous or subcutaneous means). A specific method for administering can be found in, e.g., U.S. Pat. No. 6,124,259.

The peptide to be used in the therapy will be formulated, dosed, and administered in a fashion consistent with good medical practice, taking into account the particular mammal being treated, the clinical condition of the individual patient (especially the side effects of treatment with the peptide), the type and cause of disorder being treated, the type of particular peptide used, the site of delivery of the peptide, the method of administration, the scheduling of administration, and other factors known to medical practitioners. The "effective amount" of the peptide to be administered for purposes herein are thus determined by such considerations, and is the minimum amount necessary to prevent, ameliorate, or treat the disorder herein, resulting in bioavailability of the drug to the mammal and the desired effect. As a general proposition, the total pharmaceutically effective amount of the IGF-1 antagonist peptide administered parenterally per dose will be in a range that can be measured by a dose-response curve.

Depending on the type and severity of the disease, about 1 µg/kg to 1000 mg/kg of body weight once per day of peptide is an initial candidate dosage for administration to the patient, whether, for example, by one or more separate administrations, or by continuous infusion. A typical daily dosage might range from about 1 µg/kg to 100 mg/kg or more, depending on the factors mentioned above, more preferably about 0.1 to 20 mg/kg of body weight, and, when administered subcutaneously or intramuscularly, about 0.1 to 10 mg/kg of body weight. Necessary modifications in this dosage range may be determined by one of ordinary skill in the art using only routine experimentation given the teachings herein. See Remington's *Pharmaceutical Sciences*, 16th edition, Osol, ed. (Mack Publishing Co., Easton , Pa., 1980). For repeated administrations over several days or longer, depending on the condition, the treatment is sustained until a desired suppression of disease symptoms occurs. However, other dosage regimens may be useful. The progress of this therapy is easily monitored by conventional techniques and assays.

The peptide is suitably administered by a sustained-release system. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutanic acid and gamma-ethyl-L-glutamate (Sidman et al., *Biopolymers*, 22, 547–556 (1983)), poly(2-hydroxyethyl methaerylate) (Langer et al., *J. Biomed. Mater. Res.*, 15: 167–277 (1981), and Langer, *Chem. Tech.*, 12: 98–105 (1982)), ethylene vinyl acetate (Langer et al., supra) or poly-D-(–)-3-hydroxybutyric acid (EP 133,988). Sustained-release compositions also include a liposomally-entrapped peptide. Liposomes containing the peptide are prepared by methods known per se: DE 3,218,121; Epstein et al., *Proc. Natl. Acad. Sci. U.S.A.*, 82: 3688–3692 (1985); Hwang et al., *Proc. Natl. Acacl. Sci. U.S.A.*, 77: 4030–4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (from or about 200 to 800 Angstroms) unilamellar type in which the lipid content is greater than about 30 mol. percent cholesterol, the selected proportion being adjusted for the most efficacious therapy. See also the microencapsulation technique of Langer, *Nature*, 392:5–10 (1998). The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particies and nanocapsules) or in maeroemulsions. Such techniques are disclosed in Remington's Pharmaceutical Sciences, supra.

The formulations to be used for in vivo administration must be sterile. This is readily accomplished by filtration through sterile filtration membranes.

Peptides derivatized with polyethylene glycol (PEG) having a longer life can also be employed, based on, e.g., the conjugate technology described in WO 95/32003 published Nov. 30, 1995.

For parenteral administration, in one embodiment, the peptide herein is formulated generally by mixing it at the desired degree of purity, in a unit dosage injectable form (solution, suspension, or emulsion), with a pharmaceutically, or parenterally, acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Depending on the intended mode of administration, the peptides of the present invention can be in pharmaceutical compositions in the form of solid, semi-solid or liquid dosage forms, such as, for example, tablets, suppositories, pills, capsules, powders, liquids, suspensions, or the like, preferably in unit dosage form suitable for single administration of a precise dosage. The compositions will include, as noted above, an effective amount of the selected antagonist in combination with a pharmaceutically acceptable carrier and, in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the selected antagonist without causing any undesirable biological effects or interacting in a deleterious manner with any of the other components of the pharmaceutical composition in which it is contained.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc. the peptide as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's *Pharmaceutical Sciences*, supra.

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained.

Generally, the formulations are prepared by contacting the peptide uniformly and intimately with liquid carriers or finely-divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, a buffered solution, and dextrose solution. Non-aqueous vehicles such as fixed oils and ethyl oleate are also useful herein.

The carrier suitably contains minor amounts of additives such as substances that enhance isotonicity and chemical stability. Such materials are non-toxic to recipients at the dosages and concentrations employed; and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethylene glycol (PEG); and/or neutral salts, e.g., NaCl, KCl, $MgCl_2$, $CaCl_2$, etc.

The peptide is typically formulated in such vehicles at a pH of from about 4.5 to 8. It will be understood that use of certain of the foregoing excipients, carriers, or stabilizers will result in the formation of salts of the peptide. The final preparation may be a stable liquid or lyophilized solid.

The peptide to be used for therapeutic administration must be sterile. Sterility is readily accomplished by filtration through sterile filtration membranes (e.g., 0.2 micron membranes). Therapeutic compositions generally are placed into a container having a sterile access port, for example, an intravenous solution bag or vial having a stopper pierceable by a hypodermic injection needle.

The peptide ordinarily will be stored in unit or multi-(lose containers, for example, sealed ampoules or vials, as an aqueous solution or as a lyophilized formulation for reconstitution. As an example of a lyophilized formulation, 10-mL vials arc filled with 5 ml of sterile-filtered 1% (w/v) aqueous solution of peptide, and the resulting mixture is lyophilized. The infusion solution is prepared by reconstituting the lyophilized peptide using bacteriostatic Water-for-injection.

A preferred route of administration of the present invention is in the aerosol or inhaled form. The peptides of the present invention, combined with a dispersing agent, or dispersant, can be administered in an aerosol formulation as a dry powder or in a solution or suspension with a diluent.

Suitable dispersing agents are well known in the art, and include but are not limited to surfactants and the like. For example, surfactants that are generally used in the art to reduce surface-induced aggregation of the peptide caused by atomization of the solution forming the liquid aerosol may be used. Non-limiting examples are surfactants such as polyoxyethylene fatty acid esters and alcohols and polyoxyethylene sorbitan fatty acid esters. Amounts of surfactants used will vary, being generally within the range of about 0.001 and 4% by weight of the formulation. In a specific aspect, the surfactant is polyoxyethylene sorbitan monooleate or sorbitan trioleate. Suitable surfactants are well known in the art, and can be selected on the basis of desired properties, depending on the specific formulation, concentration of the peptide, diluent (in a liquid formulation), or form of powder (in a dry powder formulation), etc.

Moreover, depending on the choice of the peptide, the desired therapeutic effect, the quality of the lung tissue (e.g., diseased or healthy lungs), and numerous other factors, the liquid or dry formulations can comprise additional components, as discussed further below.

The liquid aerosol formulations generally contain the peptide and a dispersing agent in a physiologically-acceptable diluent. The dry powder aerosol formulations of the present invention consist of a finely divided solid form of the peptide and a dispersing agent. With either the liquid or dry powder aerosol formulation, the formulation must be aerosolized. That is, it must be broken down into liquid or solid particles to ensure that the aerosolized dose actually reaches the alveoli. In general, the mass median dynamic diameter will be about 5 micrometers or less in order to ensure that the drug particles reach the lung alveoli (Weariley, *Crit. Rev. in Ther. Drug Carrier Systems,* 8: 333 (1991)). Aerosol particles are the liquid or solid particles suitable for pulmonary administration, i.e., that will reach the alveoli. Other considerations such as construction of the delivery device, additional components in the formulation, and particle characteristics are important. These aspects of pulmonary administration of a drug are well known in the art, and manipulation of formulations, aerosolization means, and construction of a delivery device require at most routine experimentation by one of ordinary skill in the art.

With regard to construction of the delivery device, any form of aerosolization known in the art, including but not limited to nebulization, atomization, or pump aerosolization of a liquid formulation, and aerosolization of a dry powder formulation, can be used in the practice of the invention. A delivery device that is uniquely designed for administration of solid formulations is envisioned. Often, the aerosolization of a liquid or a dry powder formulation will require a propellant. The propellent may be any propellant generally used in the art. Specific nonlimiting examples of such useful propellants include a chloroflourocarbon, a hydrofluorocarbon, a hydrochlorofluorocarbon, or a hydrocarbon, including trifluoromethane, dichlorodifluoromethane, dichlorotetrafluoroethanol, and 1,1,1,2-tetrafluoroethane, or combinations thereof.

In a preferred aspect of the invention, the device for aerosolization is a metered dose inhaler. A metered dose inhaler provides a specific dosage when administered, rather than a variable dose depending on administration. Such a metered dose inhaler can be used with either a liquid or a dry powder aerosol formulation. Metered dose inhalers are well known in the art.

Once the peptide reaches the lung, a number of formulation-dependent factors affect the drug absorption. It will be appreciated that in treating a disease or disorder that requires circulatory levels of the peptide, such factors as aerosol particle size, aerosol particle shape, the presence or absence of infection, lung disease, or emboli may affect the absorption of the peptides. For each of the formulations described herein, certain lubricators, absorption enhancers, protein stabilizers or suspending agents may be appropriate. The choice of these additional agents will vary depending on the goal. It will be appreciated that in instances where local delivery of the peptides is desired or sought, such variables as absorption enhancement will be less critical.

The liquid aerosol formulations of the present invention will typically be used with a nebulizer. The nebulizer can be either compressed air driven or ultrasonic. Any nebulizer known in the art can be used in conjunction with the present invention such as but not limited to the: ULTRAVENT™ nebulizer (Mallinekrodt, Inc., St. Louis, Mo.) or the ACORN II™ nebulizer (Marquest Medical Products, Englewood Colo.). Other nebulizers useful in conjunction with the present invention are described in U.S. Pat. Nos. 4,624,251; 3,703,173; 3,561,444; and 4,635,627.

The liquid aerosol formulation may include a carrier. The carrier is a macromolecule that is soluble in the circulatory system and that is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to soya lecithin, oleic acid, and sorbitan trioleate, with sorbitan trioleate preferred.

The liquid aerosol formulations herein may also include other agents useful for protein stabilization or for the regulation of osmotic pressure. Examples of the agents include but are not limited to salts, such as sodium chloride or potassium chloride, and carbohydrates, such as glucose, galactose or mannose, and the like.

It is also contemplated that the present pharmaceutical formulation will be used as a dry powder inhaler formulation comprising a finely divided powder form of the peptide and a dispersant. The form of the peptide will generally be a lyophilized powder. Lyophilized forms of peptides can be obtained through standard techniques.

In another embodiment, the dry powder formulation will comprise a finely divided dry powder containing one or more peptides of the present invention, a dispersing agent and also a bulking agent. Bulking agents useful in conjunction with the present formulation include such agents as lactose, sorbitol, sucrose, or mannitol, in amounts that facilitate the dispersal of the powder from the device.

The formulation herein may also contain more than one active compound as necessary for the particular indication being treated, preferably those with complementary activities that do not adversely affect each other. Hence, the present application contemplates combining the peptide with one or more other therapeutic agent(s), which depend on the particular indication being treated. While the agent may be an endocrine agent such as a GH, a GHRP, a GHRH, a GH secretagogue, an IGFBP, ALS, a GH complexed with a GHBP, it is preferably a cytotoxic agent, especially for treating cancer. For instance, the peptide may be co-administered with another peptide (or multivalent antibodies), a monovalent or bivalent antibody (or antibodies), chemotherapeutic agent(s) (including cocktails of chemotherapeutic agents), other cytotoxic agent(s), anti-angiogenic agent(s), cytokines, and/or growth inhibitory agent(s). Where the peptide induces apoptosis, it may be particularly desirable to combine the peptide with one or more other therapeutic agent(s) that also induce apoptosis. For instance, the peptide may be combined with pro-apoptotic antibodies (e.g., bivalent or multivalent antibodies) directed against B-cell surface antigens (e.g., RITUXAN®, ZEVALIN® or BEXXAR® anti-CD20 antibodies) and/or with (1) pro-apoptotic antibodies (e.g., bivalent or multivalent antibodies directed against a receptor in the TNF receptor superfamily, such as anti-DR4 or anti-DR5 antibodies) or (2) cytokines in the TNF family of cytokines (e.g., Apo2L). Likewise, the peptide may be administered along with anti-ErbB antibodies (e.g., HERCEPTIN® anti-HER2 antibody) alone or combined with (1) and/or (2). Alternatively, or additionally, the patient may receive combined radiation therapy (e.g., external beam irradiation or therapy with a radioactive labeled agent, such as an antibody), ovarian ablation, chemical or surgical, or high-dose chemotherapy along with bone marrow transplantation or peripheral-blood stem-cell rescue or transplantation. Such combined therapies noted above include combined administration (where the two or more agents are included in the same or separate formulations), and separate administration, in which case, administration of the peptide can occur prior to, and/or following, administration of the adjunct therapy or therapies. The effective amount of such other agents depends on the amount of peptide present in the formulation, the type of disorder or treatment, and other factors discussed above. These are generally used in the same dosages and with administration routes as used hereinbefore or about from 1 to 99% of the heretofore employed dosages.

Optionally, before the peptide is administered to the mammal, the levels of various markers are measured to determine disease state. Hence, assays can be used for measuring IGF levels, particularly IGF-1 levels as a measure of predicting, diagnosing, and monitoring a disorder such as cancer. A strong consistent positive association between IGF-1 and breast or prostate cancer risk has been observed, especially with adjustment for IGFBP-3. See WO 99/38011. High levels of IGF-1 are predictive of increased risk for prostate cancers, whereas IGFBP has a protective effect. Additionally, the IGF or IGF/IGFBP assay can be combined with a test for prostate-specific antigen (PSA) for improved ability to predict patient prognosis and monitor treatment. The method involves measuring the concentration of IGF or IGFBP-3 and/or PSA in a body sample from a mammal, wherein changes in the concentration of such components as compared to normal reference values indicate an increased risk for prostate cancer.

In one embodiment, before treatment the concentration of IGF-1 is measured in a body sample from the mammal, wherein an elevated concentration of IGF-1 above a reference range for IGF-1 indicates an increased risk for prostate cancer.

In another embodiment, the method involves measuring the concentration of IGF-1 and IGFBP in a specimen from an individual, wherein increased IGF-1 and decreased IGFBP, as compared to a nor mal reference range value, indicates an increased risk for prostate cancer.

In yet another embodiment, the method involves measuring the IGF/PSA status of an individual. High IGF and PSA levels and/or low IGFBP levels are indicative of individuals at risk for severe prostate cancer or who have prostate cancer with a poor prognosis.

A multivariate adjustment of the IGF-1 concentration relative to the IGFBP-3 concentration provides an adjusted IGF-1 level that can be compared to an adjusted normal reference range value. An algorithm can be designed, by those skilled in the art of statistical analyses, which will allow the user to quickly calculate an adjusted IGF level or IGF status for use in making predictions or monitoring prostate disease. With additional patient data, generated similarly to the manner described herein, it will be possible to more accurately define normal reference range values for IGF status parameters. The algorithm and normal reference values can be used to generate a device that will allow the end user to input IGF, IGFBP, and quickly and easily determine the IGF status or risk index of an individual. Similarly, it is possible to provide a device that indicates the IGF/PSA status of an individual.

The IGF status is reflected in the levels of IGF and IGFBP. For example, a high IGF status is reflected by high levels of IGF and stimulators of IGF activity and low levels of inhibitors of IGF activity such as IGFBP. The IGF status of an individual is now known to vary—either up or down—in certain conditions involving the prostate, including but not limited to prostate adenocarcinoma and benign prostatic hyperplasia. The IGF/PSA status is a combination of IGF status and PSA levels. Individuals with high IGF/PSA status are at risk for developing severe prostate cancer. High IGF and PSA levels and low IGFBP levels reflect a high IGF/PSA status.

"Prostate disease" includes diseases or disorders associated with pathologic conditions of the prostate, including but not limited to, prostate cancer or benign prostatic hyperplasia. The method here is preferably used to determine the risk of an individual developing prostate cancer.

The body sample collected from the mammal may be taken by any method, including venipuncture or capillary puncture, or biopsy, and the specimen collected into an appropriate container for receiving the specimen. Alternative, the specimen may be placed onto filter paper.

The IGF and IGFBP and/or PSA can be measured by techniques well known to those skilled in the art, including immunoassays such as enzyme-linked immunosorbent assay (ELISA), enzyme immunoassay (EIA), fluorescence polarization immunoassay (FPIA), fluorescence immunoassay (FIA), and radioimmunoassay (RIA). The assays described in, for example, U.S. Pat. Nos. 5,935,775; 6,066,464; and 5,747,273; Zapp et al., *J. Clin. Invest.*, 68: 1321–1330 (198 1); and EP 700,994) are particularly suitable herein. Further, the concentrations of the IGF, IGFBP, and/or PSA may, for example, be measured by test kits supplied by Diagnostic Systems Laboratories, Inc., Webster, Tex. In a preferred embodiment, total IGF-1 can be measured. In some cases, it may be advantageous to measure total, bound, and/or free IGF-1. For example, suitable highly specific and simple non-competitive ELISAs for reliable determination of IGF-1 (Khosravi et al., *Clin. Chem.*, 42:1147–54 (1996)), IGFBP-3 (Khosravi et at., *Clin. Chem.*, S6:234 (1996)), and IGFBP-1 (Khosravi et al., *Clin. Chem.*, S6:171 (1996)) have been described. The high-affinity antibodies incorporated in these immunoassays have been selected for lack of cross-reactivity or interference by the closely related peptides or binding protein.

Men in the highest quartile of circulating IGF-1 have a relative risk of prostate cancer of 4.32 (95 percent confidence interval 1.76–10.6) compared to men in the lowest quartile. There was a significant linear trend such that a 100 ng/ml increase in IGF-1 level was associated with a doubling of risk (p=0.001). Furthermore, this association is evident among men with normal as well as elevated baseline PSA levels. These results indicate that circulating IGF-1 is a predictor of prostate cancer risk.

In addition, the invention contemplates using gene therapy for treating a mammal, using nucleic acid encoding the IGF antagonist peptide. Generally, gene therapy is used to increase (or overexpress) IGF levels in the mammal. Nucleic acids that encode the IGF antagonist peptide can be used for this purpose. Once the amino acid sequence is known, one can generate several nucleic acid molecules using the degeneracy of the genetic code, and select which to use for gene therapy.

There are two major approaches to getting the nucleic acid (optionally contained in a vector) into the patient's cells for purposes of gene therapy: in vivo and ex vivo. For in vivo delivery, the nucleic acid is injected directly into the patient, usually at the site where the IGF antagonist peptide is required. For ex vivo treatment, the patient's cells are removed, the nucleic acid is introduced into these isolated cells and the modified cells are administered to the patient either directly or, for example, encapsulated within porous membranes which are implanted into the patient. See, e.g., U.S. Pat. Nos. 4,892,538 and 5,283,187. There are a variety of techniques available for introducing nucleic acids into viable cells. The techniques vary depending upon whether the nucleic acid is transferred into cultured cells in vitro or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE, and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins that bind to a cell-surface membrane protein associated with endocytosis may be used for targeting and/or to facilitate uptake. Such proteins include, e.g., capsid proteins or fragments thereof tropic for a particular cell type, antibodies for proteins that undergo internalization in cycling, and proteins that target intracellular localization and enhance intracellular half-life. The technique of receptor-mediated endocytosis is described, for example, by Wu et al., *J. Biol. Chem.*, 262: 4429–4432 (1987) and Wagner et al., *Proc. Natl. Acad. Sci. USA*, 87: 3410–3414 (1990). For review of the currently known gene marking and gene therapy protocols, see Anderson et al., *Science*, 256: 808–813 (1992). See also WO 93/25673 and the references cited therein.

Articles of Manufacture

In another embodiment of the invention, an article of manufacture or kit containing materials useful for the treatment of the disorders described above is provided. The article of manufacture comprises a container and instructions, such as a label or package or product insert on or associated with the container. Suitable containers include, for example, bottles, vials, syringes, etc., preferably a vial. The containers may be formed from a variety of materials such as glass or plastic. The container holds a composition with at least the peptide herein and may have a sterile access port (for example the container may be an intravenous solution bag or a vial having a stopper pierceable by a hypodermic injection needle). The instructions direct the user how to utilize the composition for treating the condition of choice, such as cancer. The kit may optionally include a second container with a composition comprising a further active agent as set forth above, such as a cytotoxic agent. Alternatively, or additionally, the article of manufacture may further comprise a second (or third) container comprising a pharmaceutically acceptable buffer, such as bacteriostatic water for injection (BWFI), phosphate-buffered saline, Ringer's solution, and dextrose solution. It may further include other materials desirable from a commercial and user standpoint, including other buffers, diluents, filters, needles, and syringes.

The invention will be more fully understood by reference to the following examples. They should not, however, be construed as limiting the scope of the invention. The disclosures of all literature and patent citations mentioned herein are expressly incorporated by reference.

EXAMPLES

Data on a model compound (an IGF-1 mutant with amino acid changes at residues 24 and 31 (Y24L,Y31 A), also designated (Leu$^{24}$,Ala$^{31}$)hIGF-1 or IGF-M) for predicting behavior of the peptides herein in vitro and in vivo is also disclosed in WO 98/45427, supra. WO 98/45427 also discloses how to dose an IGF antagonist for use in humans. From the doses of IGF-1 used and the concentrations of IGFBP, IGF-1 and IGF-2 demonstrated, it is simple to calculate how much of an IGF antagonist should be given to decrease levels of active endogenous IGF. The molecular size relative to IGF-1, the affinity of the IGF antagonist for the IGF-1, and its bioavailability would be other variables taken into account to arrive at doses that decreased active IGF in a human.

EXAMPLE 1

Experimental Procedure

Construction of Polyvalent Naïve Peptide Libraries

Libraries were constructed using the method of Sidhu et al., *Methods Enzymol.*, 328 333–363 (2000) with a phagemid containing an IPTG-inducible Ptac promoter driving the expression of open reading frames encoding fusion proteins of the following form: the STII secretion signal (MKKNIAFLLASMFVFSIATNAYA; SEQ ID NO:8), followed by a random peptide (i.e., a member of the naive peptide library), followed by a linker (GGGSGGG; SEQ ID NO:9), followed by the M13 gene-8 major coat protein (AEGDDPAKAAFNSLQASATEYIGYAWAMVVVIVGA TIGIKLFKKFTSKAS; SEQ ID NO: 10). Twenty-two different peptide libraries were constructed as shown in Table 1. Phage displaying the naive libraries were purified by precipitation with PEG/NaCl as described in Sidhu et al., supra, and stored frozen at −70° C.

Isolation of IGF-1 Binding Peptides From NäPeptide-phage Libraries

IGF-1 was obtained in house as described in U.S. Pat. No. 5,342,763.

Immunosorbant plates (Nunc Maxisorp) were coated with 5 μpg/ml of IGF-1 in 50 mM sodium carbonate buffer (pH 9.6) for one hour at room temperature, followed by blocking for 1 hr with 0.2% BSA in phosphate-buffered saline (PBS). The plates were washed four times with PBS, 0.05% TWEEN®-20 detergent.

Phage from 26 naive peptide-P8 libraries (Table 1) were pooled. To select peptide-phage that bound specifically to IGF-1, the library pool was added to the above-described IGF-1-coated plate. In the first round of selection, 4.8 mL of phage solution (about $10^{13}$ phage/mL) was added to 48 coated wells (100 μl/well). After two hours incubation with shaking, the plate was washed 12 times with PBS, 0.05% TWEEN®-20 detergent to remove unbound phage. Bound phage were then eluted with 0.2M glycine, pH 2.0 for 5 minutes (100 μl/well), and the phage eluant was neutralized by adding ⅙ volume of 1.0M Tris, pH 8.0. The eluted phage were amplified by propagation in E. coli XL1-blue cells with M13-VCS helper phage (Stratagene), and the amplified phage pool was cycled through additional rounds of binding selection. In total, four rounds of binding selection were performed. The procedure for round 3 was identical to that for round 1, while rounds 2 and 4 differed only in the use of 0.2% Casein in place of BSA in both the blocking solution and the phage cocktail.

From each round, individual peptide-displaying phage were isolated and analyzed for binding to IGF-1 in a phage ELISA by capturing the peptide-phage with IGF-1 immobilized on a plate, and detecting bound phage (see below). As a control for non-specific binding, the phage were also analyzed in a phage ELISA that used plates coated with BSA. Phage that exhibited strong signals in the phage ELISA with IGF-1 immobilized on plates, but not with the control ELISA, were subjected to DNA sequence analysis. The results from sequencing of positive phage clones are seen in Table 2a.

Second-Generation Affinity Maturation of IGF-1 Binding Peptides

The IGF-1 binding peptides from the CX9C class shown in Table 2a could be grouped into two distinct families based on sequence homology. Based on the sequence conservation in the two families, four second-generation libraries were designed in which highly conserved residues were held constant, moderately conserved residues were represented by degenerate codons that provided partial randomization, and unconserved residues were represented by a codon (NNK) that encoded all twenty natural amino acids (Table 2b). The peptide phage libraries were displayed on the N-terminus of human growth hormone (hGH) fused to P3 of the phage coat to ensure monovalency (Table 2b).

Phage from the libraries were pooled and cycled through four rounds of binding selections as described above. Rounds 1 and 3 used immobilized IGF-1 as the capture target to select phage that bound specifically to IGF-1; 0.2% BSA was used in the blocking buffer and the phage cocktail. Rounds 2 and 4 used anti-hGH monoclonal antibody 3F6.B1.4B13 (Jin et al., J. Mol. Biol., 226: 851–865 (1992)) as the capture target to select for phage that still displayed hGH and thus select against clones in which the hGH gene had been deleted; 0.2% Casein was used in the blocking buffer and the phage cocktail.

Finally, a fifth round of selection was conducted in which the harvested phage pool was incubated with 1.0 nM biotinylated IGF-1 (bio-IGF) in PBS with 0.2% BSA for 2 hours. The phage and bio-IGF solution was added to streptavidin-linked magnetic beads, previously blocked with BSA and washed as above. After half an hour, the magnetic beads were washed 12 times with PBS, 0.05% TWEEN®-20 detergent to remove unbound phage. The remaining phage was eluted with 1.0 M HCl and neutralized by adding ⅙ volume of 1.0 M Tris buffer, pH 8.0.

Individual phage clones from round 5 were isolated and analyzed in phage ELISAs. Specifically binding phage clones were identified as those which bound to both IGF-1 and anti-hGH but not to BSA. These positive clones were subjected to DNA sequence analysis and the results are shown in Table 3.

Phage ELISA

E. coli XL1-Blue harboring phagemids were grown overnight at 37° C. in 2YT, 50 μg/mL carbenicillin, 10 μg/mL tetracycline and M13-VCS helper phage ($10^{10}$ phage/mL). Phage were harvested from the culture supernatant by precipitation twice with PEG/NaCl and resuspended in phosphate-buffered saline, 0.2% BSA, 0.1% TWEEN®-20 detergent (BSA blocking buffer). Phage concentrations were determined spectrophotometrically ($\lambda_{268}=1.2\times10^8$ $M^{-1}$ $cm^{-1}$).

MAXISORP™ immunoplates (96-well) were coated with capture target protein for 2 hours at room temperature (100 μL at 5 μg/mL in 50 mM carbonate buffer, pH 9.6). The plates were then blocked for 1 h with 0.2% BSA in phosphate-buffered saline (PBS) and washed eight times with PBS, 0.05% TWEEN®-20 detergent. Phage particles were serially diluted into BSA blocking buffer and 100 μL were transferred to coated wells. After I h, plates were washed eight times with PBS, 0.05% TWEEN®-20 detergent, incubated with 100 μL of 1:3000 horse radish peroxidase/anti-M 13 antibody conjugate in BSA blocking buffer for 30 min. and then washed eight times with PBS, 0.05% TWEEN®-20 detergent and two times with PBS. Plates were developed using a tetramethylbenzidine substrate (TMB, Kirkegaard and Perry, Gaithersburg, Md.), stopped with 1.0 M H3PO4, and read spectrophotometrically at 450 nm.

Affinity Measurement by Monovalent Phage ELISA

A modified phage ELISA was used to estimate the binding affinities of selected second-generation IGF-1 binding peptides displayed in a monovalent format as described in Sidhu et al., supra, and in Clackson et al., supra. Phage ELISAs were carried out as described above, using plates coated with IGF-1. Peptide-displaying phage were serially diluted and binding was measured to determine a phage concentration giving <50% of the ELISA signal at saturation.

A fixed, subsaturating concentration of peptide-phage was mixed with serial dilutions of IGF-1 and incubated for 1.0 hr and then transferred to assay plates coated with IGF-1. After 30-min incubation, the plates were washed and developed as described above. The binding affinities of the peptides for IGF-1 were determined as IC50 values where the IC50 value is defined as the concentration of IGF-1 that blocked 50% of the peptide-phage binding to the immobilized IGF-1. The results are shown in Table 4.

Peptide Synthesis

Peptides were synthesized by either manual or automated (Milligen 9050) solid-phase synthesis at 0.2 mM on PEG-polystyrene resin (Bodansky and Bodansky, in *The Practice of Peptide Synthesis* (Springer-Verlag, New York, 1984)) utilizing Fmoc chemistry. Purification was as described in Dubaquid and Lowman, *Biochemistry*, 38: 6386–6396 (1999)) Synthesized peptides are shown in Table 5.

Peptide Inhibition of Phage IGF-1 Binding to IGF Binding Proteins

For inhibition of IGFBP-1 and IGFBP3, *E. coli* cells (XL1-Blue, Stratagene) freshly transformed with the phage vector pIGF-g3 displaying human IGF-1 as described in Dubaquié and Lowman, supra, was grown overnight in 5ml of 2YT medium (Sambrook et al., *Molecular Cloning. A Laboratory Handbook* (Cold Spring Harbor Laboratory Press, Cold Spring Harbor, N.Y., 1989)). The IGF-1 displaying phage was titered against IGF bp1 and bp3 for a 500–1000× dilution for preincubation with serial dilutions the synthesized peptides and binding protein standards for 45 minutes. Immunosorbant plates were coated with IGF binding proteins and blocked with 0.5% TWEEN®-20 detergent and PBS and washed as above. The samples were added to the plates for 20 minutes, washed and detected as above. The experimental IC50 values are in Table 5.

Cell-based Insulin KIRA Assay of IGF-1 Binding Peptide Activity

A kinase receptor activation assay (KIRA) (Sadick et al., *J. Pharm. Biomed. Anal.*, 19, 883–891 (1999)) for measuring phosphorylation of human insulin receptor (hIR) was developed using Chinese hamster ovary cells transfected with the hIR. (TRY-IR 5.3) Cells were grown overnight in 96-well plates with medium (PS/20) at 37° C. Supernatants were decanted and stimulation media (PS/20 and 0.5% BSA) containing either peptide samples (peptides incubated with 25 nm IGF-1 for 1 hr), experimental controls (IGF Bp1 incubated with IGF-1 for 1 hr), and 25mm rhIGF-1 standards were added. After fifteen minute stimulation at 37° C., stimulation solutions were removed and cells were lysed with a buffer containing 50 mM HEPES, 150 mM NaCl, 0.5% Triton-X-100™ octylphenyl ethylene oxide condensate, 1 mM AEBSF, aprotinin and 0.05 mM leupeptin, and 2 mM sodium orthovanadate. Lysates were frozen at –70° C. for ELISA. Immunosorbant plates were coated with 2 μg/ml insulin receptor Ab-2 (clone 83-7) in PBS at pH 7.0 overnight at 4° C. The plate was blocked and washed as above. Cell lysates containing transfected hIR were incubated on the capture ELISA plates for 2 hrs. After removing unbound receptor by washing, biotinylated anti-phosphotyrosine 4G 10 (Upstate Biologicals Inc.) was added to detect activated receptor. After 2 hrs, the plates were developed with streptavidin conjugated to HRP and TMB substrate as above. The results are shown in Table 5.

Displacement of IGF-1 on MCF-7 Cells

MCF7 (ATCC-HTB, Bethesda, Md.), a breast carcinoma cell line that expresses IGF receptors as well as insulin receptors (Grupe et al., *J. Biol. Chem.*, 270, 22085–22088 (1995)) was used to detect inhibition of 125, IGF-1 to receptors on cells by synthesized peptides. Cell were passaged weekly in media containing a 50/50 mix of high-glucose DMEM/Ham's F12, with 10% fetal bovine serum and 10 mM HEPES pH 7.2. Cells were plated and grown overnight maintained at 37° C. and 5% $CO_2$. For IGF-1 iodination, 50 μg of IGF-1 was diluted into 200 μL of PBS and added to a tube coated with 100 μg of IODOGEN® 1,3,4,6-tetrachloro-3α-6β-diphenylglycouril) (Pierce Chemical Co.), incubated with 1 mCi of $^{125}$I-NaI (10 μL) at room temperature for 10–15 minutes. Synthesized peptides and binding protein controls were preincubated with 2 nm $^{125}$I IGF-1 for 40 minutes at 37° C. The samples were added to cells for 30 minutes. The cells were washed with media and lysed with 1N NaOH. Fifteen-minute counts were taken and the results are shown in Table 5.

Cell-based IGF-1 KIRA Assay

A KIRA for measuring the activation of the human type 1 IGF-1 receptor was performed using human MCF-7 cells (as described above). Cells were grown overnight in 96-well plates with mediuum (50:50 F12/DMEM, Gibco). Supernatants were decanted, and stimulation media (50:50 F12/DMEM with 25 mM HEPES and 2.0% BSA) containing either controls (2 nM IGF-1 preincubated with IGF Bp1 or Bp3) or experimental samples (Peptides preincubated for 30 min. with 2 nm IGF-1) were added. After 15-minute stimulation the cells were lysed, and added to the polyclonal anti-IGF-1R (3B7 Santa Cruz Biotech) coated overnight on immunosorbant plates. The detection ELISA was performed as above. The results are seen in Table 5.

Results:

TABLE 1

Naive phage library design and diversity (where X is any amino acid and any number following X is a multiplier)

| Library | Design (P8 display) | SEQ ID NO: | Diversity (× $10^{10}$) |
|---|---|---|---|
| 1 | X8 | 11 | 2.6 |
| 2 | X20 | 12 | 1.2 |
| 3 | C-X6-C-X6-CC-X3-C-X6-C | 13 | 1.6 |
| 4 | CC-X3-C-X6-C | 14 | 1.7 |
| 5 | CC-X5-C-X4-C-X4-CC | 15 | 1.6 |
| 6 | C-X-C-X7-C-X3-C-X6 | 16 | 1.5 |
| 7 | X4-C-X2-GP-X4-C-X4 | 17 | 2.0 |
| 8 | C-X2-GP-X4-C | 18 | 2.5 |
| 9 | X7-C-X4-C-X7 | 19 | 2.5 |
| 10 | X7-C-X5-C-X6 | 20 | 1.4 |
| 11 | X6-C-X6-C-X6 | 21 | 2.5 |
| 12 | X6-C-X7-C-X5 | 22 | 2.1 |
| 13 | X5-C-X8-C-X5 | 23 | 1.9 |
| 14 | X5-C-X9-C-X4 | 24 | 2.0 |
| 15 | X4-C-X10-C-X4 | 25 | 2.5 |
| 16 | X2-C-X4-C-X2 | 26 | 2.1 |
| 17 | X2-C-X5-C-X2 | 27 | 2.2 |
| 18 | X2-C-X6-C-X2 | 28 | 1.5 |
| 19 | X2-C-X7-C-X2 | 29 | 2.1 |
| 20 | X2-C-X8-C-X2 | 30 | 2.1 |
| 21 | X2-C-X9-C-X2 | 31 | 2.2 |
| 22 | X2-C-X10-C-X2 | 32 | 2.4 |

TABLE 2a

Naive Phage Peptides Sequences

| SCAFFOLD | SEQ ID NO: |
|---|---|
| X20 | |
| A S Q T P W P Y S L F G E W W N A G F | 33 |
| E A G A E S R G W L Q A R C G E L L G V | 34 |
| H W D W T G G Y W W I G R E P W K E A A | 35 |
| R L N A E X L R M G W G Y M V W H W L S | 36 |
| CX6C | |
| G A Q A W L C E Q R E E W C G Q M L G T | 37 |
| Y D W V E A C Q K W P V L C M D S T M Y | 38 |
| CX7C | |
| G I R E E L C D K G L H K M C F R E V R | 39 |
| C E C G K V S S R G C E K L C W L V S Y M | 40 |

TABLE 2a-continued

Naive Phage Peptides Sequences

| SCAFFOLD | SEQ ID NO: |
|---|---|
| CX8C | |
| D A M D C V V G P E W R K C F L E G | 41 |
| S G T A C R W G P S W L L C S L A G S P | 42 |
| G E G P E C D L R Q W G N L C G H W E T | 43 |
| L S S E E C W E A L K W Q G C L M S E R | 44 |
| S F C E F N D W W P T C L V | 45 |
| CX9C | |
| G V E T C Y S D A M N T Q Y C W T T E L | 46 |
| E V A R C V V D A G G T W Y C W A E M A | 47 |
| G E S T C V T D L E R V E Y C W D E K S | 48 |
| H P D K C F A D V R A L Q E C M E S V R | 49 |
| R E V K C M K D L S G H E Y C W A E P R | 50 |
| S T Y S C I R D M G W A V Y C W E T T L | 51 |
| V E E K C Y E S I T A L R H C M Q A M Q | 52 |
| V E S E C L L S L P N L R R C M M D R L | 53 |
| V K D E C L M S V E A L K N C M G L V S | 54 |
| V M D Q C F E S Y A E M R K C M L D G S | 55 |
| T D C L D S V E A K Q C M Y | 56 |
| I E C W Q D L Q G T R L C W E | 57 |
| G A S T T C L E K Y R E R Q W C K E L T | 58 |
| G E A A E C A Y D S L G M A Y C Y A K E | 59 |
| Q I P A G C Y E S V Q S L L E C V Q S A | 60 |
| T A G I E C A Y D K H L D Q Y C W W K E | 61 |

TABLE 2b

Second generation library construction for family I and II of the IGF-1 binding peptides.

| Library Diversity | DNA Code Possible Amino acids | | | | | | | | | | | | | | |
|---|---|---|---|---|---|---|---|---|---|---|---|---|---|---|---|
| IGF-PEP8-FI 2.0 × 10^10 | NNK All 20 | VVK PHQRT NKSA DEG | TGC C | YWC FYLH | GAS DE | AGC S | GTC V | VVK PHQRT NKSA DEG | GCT A | CTC L | ARG KR | VVK PHQRT NKSA DEG | TGT C | ATG M | NNK All 20 |
| IGF-PEP9-FII 2.6 × 10^10 | NNK All 20 | RVK TNKSR ADEG | TGC C | RYK IMVT A | NNK All 20 | GAC D | KYG LSVA | NNK All 20 | GGT G | NNK All 20 | NNK All 20 | TAC Y | TGT C | TGG W | GMK ADE |
| IGF-PEP10-FI 2.2 × 10^10 | NNK All 20 | GAS DE | TGC C | YWC FYLH | RNK IMTNK SRVAD EG | AGC S | GTC V | GAG E | GCT A | CTC L | ARG KR | NNK All 20 | TGT C | ATG M | NNK All 20 |
| IGF-PEP12-FII 2.0 × 10^10 | NNK All 20 | ARG KR | TGC C | RYK IMVT A | NNK All 20 | GAC D | KYG LSVA | RGT GS | GGT G | NNK All 20 | NNK All 20 | TAC Y | TGT C | TGG W | GMK ADE |

TABLE 3

Sequences from Second Generation Library Sorting

| | SEQ ID NO: |
|---|---|
| Family I | |
| R N C F E S V A A L R R C M Y | 62 |
| F G C Y E S V A A L R T C M Y | 63 |
| Y H C F E S V D A L R R C M K | 64 |
| L E C F K S V E A L K T C M A | 65 |
| R D C F D S V E A L R X C M Y | 66 |
| L D C F T S V E A L R W C M R | 67 |
| A E C F G S V E A L K G C M H | 68 |
| R D C F V S V E A L R H C M Y | 69 |
| H D C F A S V E A L R R C M Y | 70 |
| S D C F G S V E A L K M C M Y | 71 |
| S D C F E S V E A L R A C M Y | 72 |
| M E C H G S V E A L K I C M X | 73 |
| D E C L T S V E A L R Y C M A | 74 |
| G D C L G S V E A L K M C M D | 75 |
| N D C L D S V E A L R F C M S | 76 |
| A D C L D S V E A L R R C M R | 77 |
| F E C L T S V E A L R G C M Y | 78 |
| R D C L A S V E A L R S C M Y | 79 |
| M D C L A S V E A L K W C M Y | 80 |
| L E C Y T S V E A L K W C M R | 81 |
| M D C Y S S V E A L R Y C M R | 82 |
| L T C L D S V G A L R R C M R | 83 |
| H P C L E S V G A L K A C M Y | 84 |

TABLE 3-continued

Sequences from Second Generation Library Sorting

| | SEQ ID NO: |
|---|---|
| N S C L E S V H A L R E C M L | 85 |
| A G C L D S V K A L K R C M I | 86 |
| Y T C F E S V P A L R P C M R | 87 |
| Y T C F E S V P A L R P C M R | 88 |
| S H C F D S V R A L R H C M R | 89 |
| T S C F E S V R A L R A C M R | 90 |
| N A C L E S V R A L K A C M S | 91 |
| L T C L D S V R A L K E F M L | 92 |
| S K C L D S V S A L R R C M Q | 93 |
| R G C Y E S V T A L R H C M Y | 94 |
| Family II | |
| W R C A Q D A G G W T Y C W A | 95 |
| F R C A G D A G G R S Y C W D | 96 |
| V R C A Y D A G G S R Y C W E | 97 |
| A R C A R D A G G F Y Y C W A | 98 |
| I R C V Q D A G G V R Y C W D | 99 |
| V R C V A D A G G F L Y C W A | 100 |
| W R C V T D A G G R P Y C W A | 101 |
| A S C V A D A G G G G Y C W D | 102 |
| V D C V W D A H G W G Y C W A | 103 |
| V T C A A D A L G F L Y C W E | 104 |
| L R C T E D A S G R V Y C W D | 105 |
| G G C A S D L A G F R Y C W E | 106 |
| L G C A S D L A G F W Y C W A | 107 |
| Y R C A T D L A G F S Y C W A | 108 |
| K G C V S D L F G A G Y C W D | 109 |
| V R C A W D L G G R A Y C W A | 110 |
| L R C A E D L G G Y F Y C W A | 111 |
| W R C V D D L G G F Q Y C W A | 112 |
| V K C A R D L S G F V Y C W A | 113 |
| G G C T G D S A G P G Y C W E | 114 |
| R R C V S D S G G R T Y C W A | 115 |
| L K C A L D T F G G L Y C W A | 116 |
| R K C A S D V G G V T Y C W D | 117 |
| M S C A R D V R G V R Y C W A | 118 |
| G A C M T D V R G R E Y C W D | 119 |
| F R C A W E L G W L Y V L G L | 120 |

TABLE 4

Positive Second Generation Clones with Phage Competition IC50.

| | SEQ ID NO: | IC50 |
|---|---|---|
| F1-A H P C L E S V G A L K A C M Y | 84 | $4.01 \times 10^{-7}$ |
| F1-B F G C Y E S V A A L R T C M Y | 63 | $3.01 \times 10^{-7}$ |
| F1-C R N C F E S V A A L R R C M Y | 62 | $1.08 \times 10^{-7}$ |
| F1-D H D C F A S V E A L R R C M Y | 70 | $4.68 \times 10^{-7}$ |
| F1-E S D C F G S V E A L K M C M Y | 71 | $7.11 \times 10^{-7}$ |
| F1-F E C L T S V E A L R G C M Y | 78 | $2.86 \times 10^{-7}$ |
| F1-G S D C F E S V E A L R A C M Y | 72 | $9.68 \times 10^{-7}$ |
| F1-H M D C L A S V E A L K W C M Y | 80 | $1.47 \times 10^{-7}$ |
| F2-A G G C A S D L A G F R Y C W E | 106 | $1.33 \times 10^{-6}$ |
| F2-B V R C A Y D A G G S R Y C W E | 97 | $2.46 \times 10^{-5}$ |
| F2-C V K C A R D L S G F V Y C W A | 113 | 0.010019 |
| F2-D V R C A W D L G G R A Y C W A | 110 | 0.0002493 |
| F2-E L G C A S D L A G F W Y C W A | 107 | $5.54 \times 10^{-7}$ |
| F2-F F R C A W E L G W L Y V L L G | 120 | 0.0002087 |
| F2-G A S C V A D A G G G G Y C W D | 102 | $9.86 \times 10^{-7}$ |
| F2-H W R C V D D L G G F Q Y C W A | 112 | $3.19 \times 10^{-7}$ |
| F2-I V T C A A D A L G F L Y C W E | 104 | $1.03 \times 10^{-6}$ |
| F2-J L R C A E D L G G Y F Y C W A | 111 | $2.12 \times 10^{-6}$ |
| F2-K Y R C A T D L A G F S Y C W A | 108 | $1.45 \times 10^{-6}$ |
| F2-L A R C A R D A G G F Y Y C W A | 98 | $4.36 \times 10^{-6}$ |
| F2-M W R C A Q D A G G W T Y C W A | 95 | $1.04 \times 10^{-6}$ |
| F2-N V R C V A D A G G F L Y C W A | 101 | $1.18 \times 10^{-6}$ |

TABLE 5

| Synthetic IGF-1 Binding Peptide | Phage | BP1 Comp ($\mu$M) | BP3 Comp ($\mu$M) | Insulin KIRA ($\mu$M) | IGF-1 KIRA ($\mu$M) | MCF-7 Binding ($\mu$M) |
|---|---|---|---|---|---|---|
| F1-P DECLMSVEALKNCMGG (SEQ ID NO:121) | NT | — | — | 183 | 400 | — |
| F1-1 RNCFESVAALRRCMYG (SEQ ID NO:2) | 1.08 × 10$^{-7}$M | 1.4 | 2.93 | 5.48 | 84.9 | 5.12 |
| F1-2 MDCLASVEALKWCMYG (SEQ ID NO:3) | 1.47 × 10$^{-7}$M | 15.5 | 9.20 | 32.6 | 20 | 15.3 |
| F1-3 FECLTSVEALRGCMYG (SEQ ID NO:4) | 2.86 × 10$^{-7}$M | 11.65 | 12.84 | 66.1 | 102 | 45.7 |
| F2-P ARCVVDAGGTWYCWAG (SEQ ID NO:122) | NT | — | — | 300 | NT | — |
| F2-1 LGCASDLAGFWYCWAG (SEQ ID NO:5) | 5.54 × 10$^{-7}$M | — | — | 40.41 | NT | — |
| F2-2 WRCVDDLGGFQYCWAG (SEQ ID NO:6) | 3.19 × 10$^{-7}$M | — | — | 93.6 | 130 | — |

EXAMPLE 2

Structure Determination of IGF-F1-1 by NMR $^1$H NMR data were collected on peptide IGF-F1-1 either in pure H$_2$O solution (30° C., pH 5.1 and 5.0 millimolar concentration) or in H$_2$O containing 6% (v/v) d$_6$-DMSO (40° C., pH 5.2 and at a concentration of 6.7 millimolar). In addition to one-dimensional spectra, two-dimensional double-quantum-filtered correlation spectroscopy (2QF-COSY), total correlation spectra (TOCSY), and rotating-frame Overhauser effect spectra (ROESY) were collected. The experiments were recorded as described by Cavanagh et al. in *Protein NMR Spectroscopy, Principles and Practice* (Academic Press, San Diego; ISBN 0-12-164490-1, 1995), except that pulsed-field gradients were used for coherence selection in the 2QF-COSY (van Zijl et al., *J. Magn. Reson.*, 113A: 265–270 (1995)) and excitation sculpting was used to suppress the water resonance in the TOCSY and ROESY experiments (Hwang and Shaka, *J. Magn. Reson.*, 112A: 275–279 (1995)). After lyophilization and dissolution of the peptide in $^2$H$_2$O, a 2D ROESY spectrum (Cavanagh et al., supra) and a COSY spectrum with a 35° mixing pulse (Cavanagh et al, supra) were acquired. Complete $^1$H resonance assignments were obtained from these data by standard methods (Wüthrich, in *NMR of proteins and nucleic acids* (John Wiley & Sons, New York; ISBN 0-471-82893-9, 1986) and are listed in Table 6.

Evidence of a well defined three-dimensional structure for IGF-F1-1 was obtained from the following:

(1) Scalar coupling constants between amide and alpha protons (obtained from the 2QF-COSY spectrum) are distinct from the averaged values observed in unstructured peptides. The values less than 6.0 Hz for Glu5, Ser6, Ala8, Ala9, Leu10, Arg11, Arg12, and Cys13 are indicative of a helical conformation for these residues. The value of 8.3 Hz observed for Phe4 is indicative of an extended conformation for this residue.

(2) Scalar coupling constants were also measured between alpha and beta protons in the COSY-35 spectrum. These data indicate that the side chains of Cys3, Phe4, Ser6 and Cys13 have fixed chi-1 angles; i.e., these side chains do not sample the range of chi-1 rotamers that are populated in unstructured peptides.

(3) Peaks in the ROESY spectra indicate that there are many proton-proton contacts (<5 Å) between residues that are not adjacent in the primary sequence. These can only occur if the peptide folds up into a well-defined structure. Contacts between residues at position i and i+3 in the primary sequence are prevalent between Val6 and Arg12, consistent with the presence of a helix in this region. Many contacts are observed between the aromatic side chain of Phe4 and the methyl groups of Val7, Leu10, and Met14, indicating the presence of a hydrophobic patch along one face of the helix.

The NMR data were used to derive restraints that could be used to determine a three-dimensional model of the IGF-F1-1 structure. Dihedral angle restraints were derived from the amide-alpha and alpha-beta scalar coupling constants via an appropriate Karplus relationship (Karplus, *J. Phys. Chem.*, 30: 11–15 (1959)). Distance restraints were introduced between protons that exhibited a through-space interaction in the ROESY spectrum; the size of the upper bound, and corrections to the upper bound because of peak overlap or resonance degeneracy were as described by Skelton et al., *Biochemistry*, 33: 13581–92 (1994). These restraints were used to generate a family of structures using the program DGII (Havel, *Prog. Biophys. Mol. Biol.*, 56: 43–78 (1991)), which were subsequently refined by restrained molecular dynamics with the program Discover (MSI, San Diego) using the AMBER all-atom force field (Weiner et al., *J. Comput. Chem.*, 7: 230–252 (1986)). 81 inter-proton distance restraints (45 between non-sequential residues) and 18 dihedral angle restraints (14 φ and 4$_\chi$1) were used in the final calculation. The resulting structures converged to a single global fold (mean root-mean-squared deviation from the mean structure of 0.46±0.16 Å and 1.51±0.14 Å for backbone or all heavy atoms, respectively, of residues 3–13). The best 20 structures (least violation of the input restraints) agreed with the input data very well (no distance restraint violations greater than 0.13 Å and no dihedral angle violations greater than 2.0°), and had good covalent geometry as judged by the program PROCHECK (Laskowski et al., *J.*

*Appl. Cryst.*, 26: 283–291). Mean coordinates were generated for IGF-F1-1 from the ensemble of 20 structure; energy minimization of these coordinates under the influence of the experimental restraints produced the minimized mean structure depicted in FIG. 1. The atomic coordinates of the minimized mean are listed in Table 7.

According to the Kabsch and Sander secondary structure algorithm within PROCHECK (supra), IGF-F1-1 contains a type 1 reverse turn at residues Cys3-Phe4 and an alpha helix from Va17 to Cys13; Ser6 and Met14 are extensions of the main helix. Hydrogen-bond interactions consistent with these designations are observed in most of the structures within the ensemble. Residues Arg1,Asn2,Tyr15, and Gly16 are not well defined by the NMR restraints and may be more flexible in solution than the other residues. There are extensive hydrophobic contacts between the side-chains of Phe4, Va17, Leu10, and Met14. These residues also pack on top of the disulfide bond (residues Cys3 and Cys13). The non-bonded interactions along this face of the helix likely help to stabilize the folded conformation of the peptide.

IGF-F1-1 was selected from a peptide library displayed on phage. Although selection was based only on the ability of the peptide to bind to IGF-1, the sequence identified also folds up into a stable, compact structure. Highly structured peptides containing a C-terminal helix have been observed in a number of other phage-derived peptide selection experiments (Dennis et al., *Nature*, 404: 465–470 (2000); Lowman et al., *Biochemistry*, 37: 8870–8878 (1998)). In these examples the conformation observed for the peptide in solution is similar to that present when bound to the target protein. Selection of a peptide that has a stable fold in solution that does not change significantly on binding to its target provides an energetic benefit to binding since the association will not lead to a loss of conformational entropy. In these two examples, hydrophobic residues on one face of the peptide helix provide important contacts for binding to the target protein. On the basis of these prior findings, it is hypothesized, without being limited to any one theory, that the hydrophobic patch of residues on the front surface depicted in FIG. 1 (Phe4, Va17, Leu10, Met14) likely represents the surface that IGF-F1-1 uses to bind to or interact with IGF-1. Thus, the structure of IGF-F1-1 contains information about the particular arrangement of atoms that is necessary for binding to IGF-1.

TABLE 6

Chemical shifts and coupling constant data for IGF-F1-1[a]

| Res | $H^N$ | $H^\alpha$ | $H^\beta$ | Other | $^3J_{H\alpha\text{-}H\beta}$ | $^3J_{HN\text{-}H\alpha}$ |
|---|---|---|---|---|---|---|
| 1 Arg | — | 4.02 | 1.89* | $\gamma = 1.63^*; \delta = 3.18^*$; | *, * | — |
| 2 Asn | — | 4.80 | 2.84, 2.76 | $\delta = 7.57, 6.95$ | 7.6, 6.5 | — |
| 3 Cys | 8.52 | 4.37 | 2.92, 2.68 | | 4.5, 10.0 | 6.2 |
| 4 Phe | 7.98 | 4.65 | 3.28, 2.92 | $\delta = 7.23, \epsilon = 7.33, \zeta = 7.28$ | 4.5, 11.0 | 8.3 |
| 5 Glu | 7.82 | 4.18 | 2.03* | $\gamma = 2.28^*$ | * * | 5.6 |
| 6 Ser | 7.73 | 4.57 | 4.09, 4.00 | | 4.5, 3.0 | 5.9 |
| 7 Val | 8.43 | 3.96 | 2.14 | $\gamma = 1.06, 0.99$ | 8.0 | 6.2 |
| 8 Ala | 8.12 | 4.13 | 1.40 | | — | 5.4 |
| 9 Ala | 7.97 | 4.13 | 1.45 | | — | 5.1 |
| 10 Leu | 7.87 | 4.19 | 1.80, 1.75 | $\gamma = 1.62, \delta = 0.91, 0.85$ | *, * | 5.1 |
| 11 Arg | 8.13 | 4.12 | 1.92, 1.87 | $\gamma = 1.77, 1.64, \delta = 3.19^*$ | — | 4.7 |
| 12 Arg | 7.96 | 4.26 | 1.90, 1.84 | $\gamma = 1.79, 1.64, \delta = 3.19^*$ | — | 6.1 |
| 13 Cys | 8.22 | 4.47 | 3.35, 3.08 | | 11.0, 3.5 | 6.0 |
| 14 Met | 8.17 | 4.29 | 1.85* | $\gamma = 2.49, 2.37, \epsilon = 2.10$ | — | 6.6 |
| 15 Tyr | 8.03 | 4.65 | 3.16, 2.94 | $\delta = 7.16, \epsilon = 6.83$ | 5.5, 10.5 | 7.9 |
| 16 Gly | 8.07 | 3.95, 3.87 | | | — | — |

[a]Data obtained from $H_2O$ solution containing 6% (v/v) d6-DMSO at 40° C. and pH 5.1. Stereospecifically assigned prochiral groups are indicated by bold typeface; underlined resonances indicate the proR stereochemistry.
*indicates degenerate methylene (methyl) resonances.

TABLE 7

Atomic coordinates of the minimized mean structure of IGF-F1-1
REMARK 4 1IGF COMPLIES WITH FORMAT V. 2.0, Jan. 31, 2001

| ATOM | 1 | N | ARG | 1 | 9.068 | 4.862 | −21.485 | 1.00 | 0.00 | N1+ |
|---|---|---|---|---|---|---|---|---|---|---|
| ATOM | 2 | CA | ARG | 1 | 8.948 | 5.526 | −20.172 | 1.00 | 0.00 | C |
| ATOM | 3 | C | ARG | 1 | 7.528 | 6.018 | −19.856 | 1.00 | 0.00 | C |
| ATOM | 4 | O | ARG | 1 | 7.310 | 6.619 | −18.805 | 1.00 | 0.00 | O |
| ATOM | 5 | CB | ARG | 1 | 10.010 | 6.628 | −20.005 | 1.00 | 0.00 | C |
| ATOM | 6 | CG | ARG | 1 | 10.080 | 7.674 | −21.132 | 1.00 | 0.00 | C |
| ATOM | 7 | CD | ARG | 1 | 8.816 | 8.524 | −21.315 | 1.00 | 0.00 | C |
| ATOM | 8 | NE | ARG | 1 | 8.348 | 9.114 | −20.052 | 1.00 | 0.00 | N1+ |
| ATOM | 9 | CZ | ARG | 1 | 8.892 | 10.172 | −19.427 | 1.00 | 0.00 | C |
| ATOM | 10 | NH1 | ARG | 1 | 9.953 | 10.809 | −19.942 | 1.00 | 0.00 | N |
| ATOM | 11 | NH2 | ARG | 1 | 8.364 | 10.593 | −18.271 | 1.00 | 0.00 | N |
| ATOM | 12 | 1H | ARG | 1 | 8.848 | 5.519 | −22.219 | 1.00 | 0.00 | H |
| ATOM | 13 | 2H | ARG | 1 | 10.013 | 4.526 | −21.606 | 1.00 | 0.00 | H |
| ATOM | 14 | 3H | ARG | 1 | 8.428 | 4.081 | −21.529 | 1.00 | 0.00 | H |
| ATOM | 15 | HA | ARG | 1 | 9.169 | 4.765 | −19.422 | 1.00 | 0.00 | H |
| ATOM | 16 | 1HB | ARG | 1 | 9.871 | 7.128 | −19.046 | 1.00 | 0.00 | H |
| ATOM | 17 | 2HB | ARG | 1 | 10.983 | 6.135 | −19.972 | 1.00 | 0.00 | H |

TABLE 7-continued

Atomic coordinates of the minimized mean structure of IGF-F1-1
REMARK 4 1IGF COMPLIES WITH FORMAT V. 2.0, Jan. 31, 2001

| ATOM | 18 | 1HG | ARG | 1 | 10.308 | 7.179 | −22.076 | 1.00 | 0.00 | H |
|---|---|---|---|---|---|---|---|---|---|---|
| ATOM | 19 | 2HG | ARG | 1 | 10.914 | 8.339 | −20.904 | 1.00 | 0.00 | H |
| ATOM | 20 | 1HD | ARG | 1 | 9.016 | 9.313 | −22.041 | 1.00 | 0.00 | H |
| ATOM | 21 | 2HD | ARG | 1 | 8.020 | 7.906 | −21.727 | 1.00 | 0.00 | H |
| ATOM | 22 | HE | ARG | 1 | 7.549 | 8.667 | −19.619 | 1.00 | 0.00 | H |
| ATOM | 23 | 1HH1 | ARG | 1 | 10.354 | 11.603 | −19.465 | 1.00 | 0.00 | H |
| ATOM | 24 | 2HH1 | ARG | 1 | 10.356 | 10.496 | −20.813 | 1.00 | 0.00 | H |
| ATOM | 25 | 1HH2 | ARG | 1 | 7.552 | 10.124 | −17.894 | 1.00 | 0.00 | H |
| ATOM | 26 | 2HH2 | ARG | 1 | 8.756 | 11.385 | −17.783 | 1.00 | 0.00 | H |
| ATOM | 27 | N | ASN | 2 | 6.559 | 5.760 | −20.745 | 1.00 | 0.00 | N |
| ATOM | 28 | CA | ASN | 2 | 5.164 | 6.118 | −20.525 | 1.00 | 0.00 | C |
| ATOM | 29 | C | ASN | 2 | 4.533 | 5.260 | −19.427 | 1.00 | 0.00 | C |
| ATOM | 30 | O | ASN | 2 | 3.607 | 5.721 | −18.766 | 1.00 | 0.00 | O |
| ATOM | 31 | CB | ASN | 2 | 4.368 | 5.991 | −21.831 | 1.00 | 0.00 | C |
| ATOM | 32 | CG | ASN | 2 | 4.188 | 4.536 | −22.261 | 1.00 | 0.00 | C |
| ATOM | 33 | OD1 | ASN | 2 | 5.063 | 3.972 | −22.913 | 1.00 | 0.00 | O |
| ATOM | 34 | ND2 | ASN | 2 | 3.065 | 3.920 | −21.884 | 1.00 | 0.00 | N |
| ATOM | 35 | H | ASN | 2 | 6.779 | 5.264 | −21.597 | 1.00 | 0.00 | H |
| ATOM | 36 | HA | ASN | 2 | 5.119 | 7.164 | −20.219 | 1.00 | 0.00 | H |
| ATOM | 37 | 1HB | ASN | 2 | 4.884 | 6.539 | −22.621 | 1.00 | 0.00 | H |
| ATOM | 38 | 2HB | ASN | 2 | 3.386 | 6.445 | −21.691 | 1.00 | 0.00 | H |
| ATOM | 39 | 1HD2 | ASN | 2 | 2.912 | 2.957 | −22.147 | 1.00 | 0.00 | H |
| ATOM | 40 | 2HD2 | ASN | 2 | 2.376 | 4.408 | −21.323 | 1.00 | 0.00 | H |
| ATOM | 41 | N | CYS | 3 | 5.015 | 4.019 | −19.260 | 1.00 | 0.00 | N |
| ATOM | 42 | CA | CYS | 3 | 4.420 | 2.986 | −18.419 | 1.00 | 0.00 | C |
| ATOM | 43 | C | CYS | 3 | 3.982 | 3.500 | −17.051 | 1.00 | 0.00 | C |
| ATOM | 44 | O | CYS | 3 | 2.868 | 3.218 | −16.624 | 1.00 | 0.00 | O |
| ATOM | 45 | CB | CYS | 3 | 5.389 | 1.810 | −18.264 | 1.00 | 0.00 | C |
| ATOM | 46 | SG | CYS | 3 | 5.740 | 0.927 | −19.807 | 1.00 | 0.00 | S |
| ATOM | 47 | H | CYS | 3 | 5.786 | 3.732 | −19.845 | 1.00 | 0.00 | H |
| ATOM | 48 | HA | CYS | 3 | 3.533 | 2.615 | −18.932 | 1.00 | 0.00 | H |
| ATOM | 49 | 1HB | CYS | 3 | 6.329 | 2.151 | −17.829 | 1.00 | 0.00 | H |
| ATOM | 50 | 2HB | CYS | 3 | 4.937 | 1.097 | −17.575 | 1.00 | 0.00 | H |
| ATOM | 51 | N | PHE | 4 | 4.839 | 4.271 | −16.376 | 1.00 | 0.00 | N |
| ATOM | 52 | CA | PHE | 4 | 4.620 | 4.668 | −14.991 | 1.00 | 0.00 | C |
| ATOM | 53 | C | PHE | 4 | 3.808 | 5.963 | −14.883 | 1.00 | 0.00 | C |
| ATOM | 54 | O | PHE | 4 | 3.418 | 6.342 | −13.781 | 1.00 | 0.00 | O |
| ATOM | 55 | CB | PHE | 4 | 5.979 | 4.775 | −14.291 | 1.00 | 0.00 | C |
| ATOM | 56 | CG | PHE | 4 | 6.802 | 3.507 | −14.430 | 1.00 | 0.00 | C |
| ATOM | 57 | CD1 | PHE | 4 | 6.472 | 2.370 | −13.668 | 1.00 | 0.00 | C |
| ATOM | 58 | CD2 | PHE | 4 | 7.860 | 3.443 | −15.357 | 1.00 | 0.00 | C |
| ATOM | 59 | CE1 | PHE | 4 | 7.157 | 1.160 | −13.872 | 1.00 | 0.00 | C |
| ATOM | 60 | CE2 | PHE | 4 | 8.549 | 2.234 | −15.557 | 1.00 | 0.00 | C |
| ATOM | 61 | CZ | PHE | 4 | 8.192 | 1.090 | −14.821 | 1.00 | 0.00 | C |
| ATOM | 62 | H | PHE | 4 | 5.729 | 4.495 | −16.796 | 1.00 | 0.00 | H |
| ATOM | 63 | HA | PHE | 4 | 4.058 | 3.890 | −14.476 | 1.00 | 0.00 | H |
| ATOM | 64 | 1HB | PHE | 4 | 6.529 | 5.618 | −14.712 | 1.00 | 0.00 | H |
| ATOM | 65 | 2HB | PHE | 4 | 5.817 | 4.977 | −13.231 | 1.00 | 0.00 | H |
| ATOM | 66 | HD1 | PHE | 4 | 5.675 | 2.417 | −12.941 | 1.00 | 0.00 | H |
| ATOM | 67 | HD2 | PHE | 4 | 8.131 | 4.312 | −15.938 | 1.00 | 0.00 | H |
| ATOM | 68 | HE1 | PHE | 4 | 6.888 | 0.284 | −13.301 | 1.00 | 0.00 | H |
| ATOM | 69 | HE2 | PHE | 4 | 9.351 | 2.182 | −16.279 | 1.00 | 0.00 | H |
| ATOM | 70 | HZ | PHE | 4 | 8.717 | 0.159 | −14.980 | 1.00 | 0.00 | H |
| ATOM | 71 | N | GLU | 5 | 3.517 | 6.612 | −16.018 | 1.00 | 0.00 | N |
| ATOM | 72 | CA | GLU | 5 | 2.586 | 7.725 | −16.118 | 1.00 | 0.00 | C |
| ATOM | 73 | C | GLU | 5 | 1.192 | 7.161 | −16.410 | 1.00 | 0.00 | C |
| ATOM | 74 | O | GLU | 5 | 0.253 | 7.395 | −15.652 | 1.00 | 0.00 | O |
| ATOM | 75 | CB | GLU | 5 | 3.048 | 8.689 | −17.220 | 1.00 | 0.00 | C |
| ATOM | 76 | CG | GLU | 5 | 4.445 | 9.252 | −16.928 | 1.00 | 0.00 | C |
| ATOM | 77 | CD | GLU | 5 | 4.950 | 10.091 | −18.096 | 1.00 | 0.00 | C |
| ATOM | 78 | OE1 | GLU | 5 | 5.644 | 9.505 | −18.955 | 1.00 | 0.00 | O |
| ATOM | 79 | OE2 | GLU | 5 | 4.644 | 11.303 | −18.107 | 1.00 | 0.00 | O1− |
| ATOM | 80 | H | GLU | 5 | 3.862 | 6.243 | −16.894 | 1.00 | 0.00 | H |
| ATOM | 81 | HA | GLU | 5 | 2.556 | 8.277 | −15.177 | 1.00 | 0.00 | H |
| ATOM | 82 | 1HB | GLU | 5 | 3.068 | 8.176 | −18.181 | 1.00 | 0.00 | H |
| ATOM | 83 | 2HB | GLU | 5 | 2.340 | 9.517 | −17.287 | 1.00 | 0.00 | H |
| ATOM | 84 | 1HG | GLU | 5 | 5.155 | 8.440 | −16.766 | 1.00 | 0.00 | H |
| ATOM | 85 | 2HG | GLU | 5 | 4.407 | 9.865 | −16.027 | 1.00 | 0.00 | H |
| ATOM | 86 | N | SER | 6 | 1.070 | 6.406 | −17.510 | 1.00 | 0.00 | N |
| ATOM | 87 | CA | SER | 6 | −0.159 | 5.760 | −17.938 | 1.00 | 0.00 | C |
| ATOM | 88 | C | SER | 6 | −0.348 | 4.451 | −17.166 | 1.00 | 0.00 | C |
| ATOM | 89 | O | SER | 6 | 0.164 | 3.409 | −17.575 | 1.00 | 0.00 | O |
| ATOM | 90 | CB | SER | 6 | −0.111 | 5.533 | −19.456 | 1.00 | 0.00 | C |
| ATOM | 91 | OG | SER | 6 | 1.085 | 4.881 | −19.830 | 1.00 | 0.00 | O |
| ATOM | 92 | H | SER | 6 | 1.892 | 6.238 | −18.076 | 1.00 | 0.00 | H |
| ATOM | 93 | HA | SER | 6 | −1.008 | 6.416 | −17.739 | 1.00 | 0.00 | H |

TABLE 7-continued

Atomic coordinates of the minimized mean structure of IGF-F1-1
REMARK 4 1IGF COMPLIES WITH FORMAT V. 2.0, Jan. 31, 2001

| ATOM | 94 | 1HB | SER | 6 | −0.966 | 4.929 | −19.763 | 1.00 | 0.00 | H |
|---|---|---|---|---|---|---|---|---|---|---|
| ATOM | 95 | 2HB | SER | 6 | −0.156 | 6.494 | −19.969 | 1.00 | 0.00 | H |
| ATOM | 96 | HG | SER | 6 | 1.246 | 4.174 | −19.198 | 1.00 | 0.00 | H |
| ATOM | 97 | N | VAL | 7 | −1.099 | 4.521 | −16.059 | 1.00 | 0.00 | N |
| ATOM | 98 | CA | VAL | 7 | −1.390 | 3.409 | −15.156 | 1.00 | 0.00 | C |
| ATOM | 99 | C | VAL | 7 | −1.852 | 2.163 | −15.922 | 1.00 | 0.00 | C |
| ATOM | 100 | O | VAL | 7 | −1.406 | 1.058 | −15.622 | 1.00 | 0.00 | O |
| ATOM | 101 | CB | VAL | 7 | −2.428 | 3.844 | −14.104 | 1.00 | 0.00 | C |
| ATOM | 102 | CG1 | VAL | 7 | −1.886 | 4.995 | −13.243 | 1.00 | 0.00 | C |
| ATOM | 103 | CG2 | VAL | 7 | −2.804 | 2.681 | −13.174 | 1.00 | 0.00 | C |
| ATOM | 104 | H | VAL | 7 | −1.468 | 5.426 | −15.805 | 1.00 | 0.00 | H |
| ATOM | 105 | HA | VAL | 7 | −0.470 | 3.161 | −14.627 | 1.00 | 0.00 | H |
| ATOM | 106 | HB | VAL | 7 | −3.334 | 4.185 | −14.610 | 1.00 | 0.00 | H |
| ATOM | 107 | 1HG1 | VAL | 7 | −0.965 | 4.688 | −12.747 | 1.00 | 0.00 | H |
| ATOM | 108 | 2HG1 | VAL | 7 | −1.687 | 5.877 | −13.850 | 1.00 | 0.00 | H |
| ATOM | 109 | 3HG1 | VAL | 7 | −2.622 | 5.265 | −12.485 | 1.00 | 0.00 | H |
| ATOM | 110 | 1HG2 | VAL | 7 | −3.480 | 3.035 | −12.395 | 1.00 | 0.00 | H |
| ATOM | 111 | 2HG2 | VAL | 7 | −3.311 | 1.892 | −13.729 | 1.00 | 0.00 | H |
| ATOM | 112 | 3HG2 | VAL | 7 | −1.907 | 2.272 | −12.706 | 1.00 | 0.00 | H |
| ATOM | 113 | N | ALA | 8 | −2.737 | 2.343 | −16.910 | 1.00 | 0.00 | N |
| ATOM | 114 | CA | ALA | 8 | −3.245 | 1.267 | −17.752 | 1.00 | 0.00 | C |
| ATOM | 115 | C | ALA | 8 | −2.110 | 0.454 | −18.383 | 1.00 | 0.00 | C |
| ATOM | 116 | O | ALA | 8 | −2.138 | −0.775 | −18.339 | 1.00 | 0.00 | O |
| ATOM | 117 | CB | ALA | 8 | −4.159 | 1.854 | −18.830 | 1.00 | 0.00 | C |
| ATOM | 118 | H | ALA | 8 | −3.065 | 3.279 | −17.099 | 1.00 | 0.00 | H |
| ATOM | 119 | HA | ALA | 8 | −3.844 | 0.601 | −17.129 | 1.00 | 0.00 | H |
| ATOM | 120 | 1HB | ALA | 8 | −4.562 | 1.050 | −19.447 | 1.00 | 0.00 | H |
| ATOM | 121 | 2HB | ALA | 8 | −4.986 | 2.389 | −18.361 | 1.00 | 0.00 | H |
| ATOM | 122 | 3HB | ALA | 8 | −3.600 | 2.544 | −19.463 | 1.00 | 0.00 | H |
| ATOM | 123 | N | ALA | 9 | −1.110 | 1.137 | −18.956 | 1.00 | 0.00 | N |
| ATOM | 124 | CA | ALA | 9 | 0.041 | 0.493 | −19.573 | 1.00 | 0.00 | C |
| ATOM | 125 | C | ALA | 9 | 0.921 | −0.183 | −18.521 | 1.00 | 0.00 | C |
| ATOM | 126 | O | ALA | 9 | 1.383 | −1.297 | −18.755 | 1.00 | 0.00 | O |
| ATOM | 127 | CB | ALA | 9 | 0.846 | 1.510 | −20.383 | 1.00 | 0.00 | C |
| ATOM | 128 | H | ALA | 9 | −1.117 | 2.146 | −18.913 | 1.00 | 0.00 | H |
| ATOM | 129 | HA | ALA | 9 | −0.321 | −0.267 | −20.268 | 1.00 | 0.00 | H |
| ATOM | 130 | 1HB | ALA | 9 | 1.641 | 0.997 | −20.925 | 1.00 | 0.00 | H |
| ATOM | 131 | 2HB | ALA | 9 | 0.198 | 2.019 | −21.097 | 1.00 | 0.00 | H |
| ATOM | 132 | 3HB | ALA | 9 | 1.294 | 2.241 | −19.714 | 1.00 | 0.00 | H |
| ATOM | 133 | N | LEU | 10 | 1.138 | 0.487 | −17.377 | 1.00 | 0.00 | N |
| ATOM | 134 | CA | LEU | 10 | 1.939 | 0.017 | −16.244 | 1.00 | 0.00 | C |
| ATOM | 135 | C | LEU | 10 | 1.692 | −1.468 | −15.959 | 1.00 | 0.00 | C |
| ATOM | 136 | O | LEU | 10 | 2.636 | −2.251 | −15.870 | 1.00 | 0.00 | O |
| ATOM | 137 | CB | LEU | 10 | 1.618 | 0.868 | −15.001 | 1.00 | 0.00 | C |
| ATOM | 138 | CG | LEU | 10 | 2.813 | 1.119 | −14.068 | 1.00 | 0.00 | C |
| ATOM | 139 | CD1 | LEU | 10 | 2.377 | 2.089 | −12.963 | 1.00 | 0.00 | C |
| ATOM | 140 | CD2 | LEU | 10 | 3.346 | −0.165 | −13.427 | 1.00 | 0.00 | C |
| ATOM | 141 | H | LEU | 10 | 0.724 | 1.407 | −17.290 | 1.00 | 0.00 | H |
| ATOM | 142 | HA | LEU | 10 | 2.986 | 0.165 | −16.507 | 1.00 | 0.00 | H |
| ATOM | 143 | 1HB | LEU | 10 | 1.267 | 1.843 | −15.331 | 1.00 | 0.00 | H |
| ATOM | 144 | 2HB | LEU | 10 | 0.812 | 0.410 | −14.427 | 1.00 | 0.00 | H |
| ATOM | 145 | HG | LEU | 10 | 3.623 | 1.579 | −14.634 | 1.00 | 0.00 | H |
| ATOM | 146 | 1HD1 | LEU | 10 | 3.221 | 2.317 | −12.311 | 1.00 | 0.00 | H |
| ATOM | 147 | 2HD1 | LEU | 10 | 2.014 | 3.019 | −13.402 | 1.00 | 0.00 | H |
| ATOM | 148 | 3HD1 | LEU | 10 | 1.580 | 1.643 | −12.368 | 1.00 | 0.00 | H |
| ATOM | 149 | 1HD2 | LEU | 10 | 2.531 | −0.720 | −12.963 | 1.00 | 0.00 | H |
| ATOM | 150 | 2HD2 | LEU | 10 | 4.088 | 0.082 | −12.668 | 1.00 | 0.00 | H |
| ATOM | 151 | 3HD2 | LEU | 10 | 3.828 | −0.779 | −14.184 | 1.00 | 0.00 | H |
| ATOM | 152 | N | ARG | 11 | 0.411 | −1.838 | −15.843 | 1.00 | 0.00 | N |
| ATOM | 153 | CA | ARG | 11 | −0.061 | −3.183 | −15.534 | 1.00 | 0.00 | C |
| ATOM | 154 | C | ARG | 11 | 0.635 | −4.232 | −16.405 | 1.00 | 0.00 | C |
| ATOM | 155 | O | ARG | 11 | 1.279 | −5.138 | −15.881 | 1.00 | 0.00 | O |
| ATOM | 156 | CB | ARG | 11 | −1.584 | −3.244 | −15.715 | 1.00 | 0.00 | C |
| ATOM | 157 | CG | ARG | 11 | −2.312 | −2.303 | −14.745 | 1.00 | 0.00 | C |
| ATOM | 158 | CD | ARG | 11 | −3.799 | −2.197 | −15.096 | 1.00 | 0.00 | C |
| ATOM | 159 | NE | ARG | 11 | −4.441 | −1.098 | −14.363 | 1.00 | 0.00 | N1+ |
| ATOM | 160 | CZ | ARG | 11 | −4.800 | −1.128 | −13.069 | 1.00 | 0.00 | C |
| ATOM | 161 | NH1 | ARG | 11 | −4.608 | −2.225 | −12.323 | 1.00 | 0.00 | N |
| ATOM | 162 | NH2 | ARG | 11 | −5.357 | −0.043 | −12.515 | 1.00 | 0.00 | N |
| ATOM | 163 | H | ARG | 11 | −0.290 | −1.121 | −15.970 | 1.00 | 0.00 | H |
| ATOM | 164 | HA | ARG | 11 | 0.170 | −3.395 | −14.488 | 1.00 | 0.00 | H |
| ATOM | 165 | 1HB | ARG | 11 | −1.828 | −2.967 | −16.742 | 1.00 | 0.00 | H |
| ATOM | 166 | 2HB | ARG | 11 | −1.929 | −4.264 | −15.539 | 1.00 | 0.00 | H |
| ATOM | 167 | 1HG | ARG | 11 | −1.890 | −1.303 | −14.801 | 1.00 | 0.00 | H |
| ATOM | 168 | 2HG | ARG | 11 | −2.191 | −2.670 | −13.726 | 1.00 | 0.00 | H |
| ATOM | 169 | 1HD | ARG | 11 | −4.303 | −3.144 | −14.896 | 1.00 | 0.00 | H |

TABLE 7-continued

Atomic coordinates of the minimized mean structure of IGF-F1-1
REMARK 4 1IGF COMPLIES WITH FORMAT V. 2.0, Jan. 31, 2001

| ATOM | 170 | 2HD | ARG | 11 | −3.896 | −1.977 | −16.160 | 1.00 | 0.00 | H |
|---|---|---|---|---|---|---|---|---|---|---|
| ATOM | 171 | HE | ARG | 11 | −4.603 | −0.248 | −14.884 | 1.00 | 0.00 | H |
| ATOM | 172 | 2HH1 | ARG | 11 | −4.184 | −3.045 | −12.731 | 1.00 | 0.00 | H |
| ATOM | 173 | 1HH1 | ARG | 11 | −4.882 | −2.234 | −11.351 | 1.00 | 0.00 | H |
| ATOM | 174 | 1HH2 | ARG | 11 | −5.631 | −0.053 | −11.543 | 1.00 | 0.00 | H |
| ATOM | 175 | 2HH2 | ARG | 11 | −5.505 | 0.789 | −13.068 | 1.00 | 0.00 | H |
| ATOM | 176 | N | ARG | 12 | 0.521 | −4.095 | −17.732 | 1.00 | 0.00 | N |
| ATOM | 177 | CA | ARG | 12 | 1.150 | −5.005 | −18.679 | 1.00 | 0.00 | C |
| ATOM | 178 | C | ARG | 12 | 2.668 | −4.836 | −18.713 | 1.00 | 0.00 | C |
| ATOM | 179 | O | ARG | 12 | 3.387 | −5.828 | −18.801 | 1.00 | 0.00 | O |
| ATOM | 180 | CB | ARG | 12 | 0.576 | −4.808 | −20.086 | 1.00 | 0.00 | C |
| ATOM | 181 | CG | ARG | 12 | −0.805 | −5.459 | −20.231 | 1.00 | 0.00 | C |
| ATOM | 182 | CD | ARG | 12 | −1.215 | −5.535 | −21.705 | 1.00 | 0.00 | C |
| ATOM | 183 | NE | ARG | 12 | −0.296 | −6.395 | −22.465 | 1.00 | 0.00 | N1+ |
| ATOM | 184 | CZ | ARG | 12 | −0.331 | −6.587 | −23.792 | 1.00 | 0.00 | C |
| ATOM | 185 | NH1 | ARG | 12 | −1.292 | −6.032 | −24.544 | 1.00 | 0.00 | N |
| ATOM | 186 | NH2 | ARG | 12 | 0.613 | −7.344 | −24.367 | 1.00 | 0.00 | N |
| ATOM | 187 | H | ARG | 12 | 0.007 | −3.307 | −18.101 | 1.00 | 0.00 | H |
| ATOM | 188 | HA | ARG | 12 | 0.942 | −6.025 | −18.370 | 1.00 | 0.00 | H |
| ATOM | 189 | 1HB | ARG | 12 | 0.523 | −3.747 | −20.333 | 1.00 | 0.00 | H |
| ATOM | 190 | 2HB | ARG | 12 | 1.262 | −5.284 | −20.783 | 1.00 | 0.00 | H |
| ATOM | 191 | 1HG | ARG | 12 | −0.778 | −6.473 | −19.832 | 1.00 | 0.00 | H |
| ATOM | 192 | 2HG | ARG | 12 | −1.541 | −4.879 | −19.673 | 1.00 | 0.00 | H |
| ATOM | 193 | 1HD | ARG | 12 | −2.223 | −5.949 | −21.769 | 1.00 | 0.00 | H |
| ATOM | 194 | 2HD | ARG | 12 | −1.216 | −4.530 | −22.129 | 1.00 | 0.00 | H |
| ATOM | 195 | HE | ARG | 12 | 0.445 | −6.844 | −21.942 | 1.00 | 0.00 | H |
| ATOM | 196 | 2HH1 | ARG | 12 | −2.004 | −5.462 | −24.111 | 1.00 | 0.00 | H |
| ATOM | 197 | 1HH1 | ARG | 12 | −1.307 | −6.182 | −25.542 | 1.00 | 0.00 | H |
| ATOM | 198 | 1HH2 | ARG | 12 | 1.348 | −7.745 | −23.800 | 1.00 | 0.00 | H |
| ATOM | 199 | 2HH2 | ARG | 12 | 0.603 | −7.503 | −25.364 | 1.00 | 0.00 | H |
| ATOM | 200 | N | CYS | 13 | 3.142 | −3.586 | −18.683 | 1.00 | 0.00 | N |
| ATOM | 201 | CA | CYS | 13 | 4.531 | −3.206 | −18.914 | 1.00 | 0.00 | C |
| ATOM | 202 | C | CYS | 13 | 5.525 | −3.948 | −18.013 | 1.00 | 0.00 | C |
| ATOM | 203 | O | CYS | 13 | 6.661 | −4.171 | −18.428 | 1.00 | 0.00 | O |
| ATOM | 204 | CB | CYS | 13 | 4.649 | −1.684 | −18.783 | 1.00 | 0.00 | C |
| ATOM | 205 | SG | CYS | 13 | 6.253 | −0.953 | −19.202 | 1.00 | 0.00 | S |
| ATOM | 206 | H | CYS | 13 | 2.476 | −2.833 | −18.584 | 1.00 | 0.00 | H |
| ATOM | 207 | HA | CYS | 13 | 4.770 | −3.463 | −19.947 | 1.00 | 0.00 | H |
| ATOM | 208 | 1HB | CYS | 13 | 3.918 | −1.242 | −19.461 | 1.00 | 0.00 | H |
| ATOM | 209 | 2HB | CYS | 13 | 4.396 | −1.389 | −17.766 | 1.00 | 0.00 | H |
| ATOM | 210 | N | MET | 14 | 5.105 | −4.380 | −16.816 | 1.00 | 0.00 | N |
| ATOM | 211 | CA | MET | 14 | 5.942 | −5.147 | −15.894 | 1.00 | 0.00 | C |
| ATOM | 212 | C | MET | 14 | 6.053 | −6.635 | −16.274 | 1.00 | 0.00 | C |
| ATOM | 213 | O | MET | 14 | 6.252 | −7.476 | −15.399 | 1.00 | 0.00 | O |
| ATOM | 214 | CB | MET | 14 | 5.406 | −4.976 | −14.464 | 1.00 | 0.00 | C |
| ATOM | 215 | CG | MET | 14 | 5.447 | −3.513 | −14.009 | 1.00 | 0.00 | C |
| ATOM | 216 | SD | MET | 14 | 4.877 | −3.219 | −12.313 | 1.00 | 0.00 | S |
| ATOM | 217 | CE | MET | 14 | 3.147 | −3.748 | −12.439 | 1.00 | 0.00 | C |
| ATOM | 218 | H | MET | 14 | 4.157 | −4.176 | −16.530 | 1.00 | 0.00 | H |
| ATOM | 219 | HA | MET | 14 | 6.954 | −4.744 | −15.928 | 1.00 | 0.00 | H |
| ATOM | 220 | 1HB | MET | 14 | 4.382 | −5.349 | −14.430 | 1.00 | 0.00 | H |
| ATOM | 221 | 2HB | MET | 14 | 6.016 | −5.556 | −13.770 | 1.00 | 0.00 | H |
| ATOM | 222 | 1HG | MET | 14 | 4.841 | −2.904 | −14.676 | 1.00 | 0.00 | H |
| ATOM | 223 | 2HG | MET | 14 | 6.478 | −3.163 | −14.074 | 1.00 | 0.00 | H |
| ATOM | 224 | 1HE | MET | 14 | 3.096 | −4.826 | −12.584 | 1.00 | 0.00 | H |
| ATOM | 225 | 2HE | MET | 14 | 2.627 | −3.490 | −11.517 | 1.00 | 0.00 | H |
| ATOM | 226 | 3HE | MET | 14 | 2.665 | −3.245 | −13.277 | 1.00 | 0.00 | H |
| ATOM | 227 | N | TYR | 15 | 5.966 | −6.955 | −17.571 | 1.00 | 0.00 | N |
| ATOM | 228 | CA | TYR | 15 | 6.208 | −8.276 | −18.144 | 1.00 | 0.00 | C |
| ATOM | 229 | C | TYR | 15 | 6.195 | −8.190 | −19.673 | 1.00 | 0.00 | C |
| ATOM | 230 | O | TYR | 15 | 7.091 | −8.715 | −20.332 | 1.00 | 0.00 | O |
| ATOM | 231 | CB | TYR | 15 | 5.219 | −9.338 | −17.628 | 1.00 | 0.00 | C |
| ATOM | 232 | CG | TYR | 15 | 3.737 | −9.035 | −17.779 | 1.00 | 0.00 | C |
| ATOM | 233 | CD1 | TYR | 15 | 3.054 | −9.396 | −18.956 | 1.00 | 0.00 | C |
| ATOM | 234 | CD2 | TYR | 15 | 3.028 | −8.436 | −16.720 | 1.00 | 0.00 | C |
| ATOM | 235 | CE1 | TYR | 15 | 1.667 | −9.198 | −19.058 | 1.00 | 0.00 | C |
| ATOM | 236 | CE2 | TYR | 15 | 1.635 | −8.274 | −16.808 | 1.00 | 0.00 | C |
| ATOM | 237 | CZ | TYR | 15 | 0.952 | −8.664 | −17.972 | 1.00 | 0.00 | C |
| ATOM | 238 | OH | TYR | 15 | −0.402 | −8.517 | −18.047 | 1.00 | 0.00 | O |
| ATOM | 239 | H | TYR | 15 | 5.831 | −6.199 | −18.224 | 1.00 | 0.00 | H |
| ATOM | 240 | HA | TYR | 15 | 7.209 | −8.590 | −17.845 | 1.00 | 0.00 | H |
| ATOM | 241 | 1HB | TYR | 15 | 5.430 | −10.269 | −18.157 | 1.00 | 0.00 | H |
| ATOM | 242 | 2HB | TYR | 15 | 5.422 | −9.532 | −16.576 | 1.00 | 0.00 | H |
| ATOM | 243 | HD1 | TYR | 15 | 3.587 | −9.844 | −19.782 | 1.00 | 0.00 | H |
| ATOM | 244 | HD2 | TYR | 15 | 3.541 | −8.135 | −15.819 | 1.00 | 0.00 | H |
| ATOM | 245 | HE1 | TYR | 15 | 1.151 | −9.477 | −19.966 | 1.00 | 0.00 | H |

TABLE 7-continued

Atomic coordinates of the minimized mean structure of IGF-F1-1
REMARK 4 1IGF COMPLIES WITH FORMAT V. 2.0, Jan. 31, 2001

| ATOM | 246 | HE2 | TYR | 15 | 1.089  | −7.854 | −15.976 | 1.00 | 0.00 | H   |
|------|-----|-----|-----|----|--------|--------|---------|------|------|-----|
| ATOM | 247 | HH  | TYR | 15 | −0.771 | −8.820 | −18.879 | 1.00 | 0.00 | H   |
| ATOM | 248 | N   | GLY | 16 | 5.175  | −7.530 | −20.233 | 1.00 | 0.00 | N   |
| ATOM | 249 | CA  | GLY | 16 | 4.972  | −7.394 | −21.664 | 1.00 | 0.00 | C   |
| ATOM | 250 | C   | GLY | 16 | 3.630  | −6.713 | −21.920 | 1.00 | 0.00 | C   |
| ATOM | 251 | O   | GLY | 16 | 2.619  | −7.446 | −21.996 | 1.00 | 0.00 | O   |
| ATOM | 252 | OXT | GLY | 16 | 3.636  | −5.467 | −22.024 | 1.00 | 0.00 | O1− |
| ATOM | 253 | H   | GLY | 16 | 4.476  | −7.124 | −19.626 | 1.00 | 0.00 | H   |
| ATOM | 254 | 1HA | GLY | 16 | 5.777  | −6.795 | −22.091 | 1.00 | 0.00 | H   |
| ATOM | 255 | 2HA | GLY | 16 | 4.974  | −8.380 | −22.131 | 1.00 | 0.00 | H   |
| TER  |     |     |     |    |        |        |         |      |      |     |

The present invention has of necessity been discussed herein by reference to certain specific methods and materials. It is to be understood that the discussion of these specific methods and materials in no way constitutes any limitation on the scope of the present invention, which extends to any and all alternative materials and methods suitable for accomplishing the objectives of the present invention.

---

What is claimed is:

1. A peptide comprising the sequence RNCFESVAALRRCMYG (SEQ ID NO:2), MDCLASVEALKWCMYG (SEQ ID NO:3), or FECLTSVEALRGCMYG (SEQ ID NO:4).

2. The peptide of claim 1 that comprises the sequence RNCFESVAALRRCMYG (SEQ ID NO:2) or MDCLASVEALKWCMYG (SEQ ID NO:3).

3. The peptide of claim 1 or claim 2 that is conjugated to a cytotoxic agent or polyethylene glycol.

* * * * *